US012234501B2

(12) United States Patent
Seelig et al.

(10) Patent No.: US 12,234,501 B2
(45) Date of Patent: *Feb. 25, 2025

(54) IN SITU COMBINATORIAL LABELING OF CELLULAR MOLECULES

(71) Applicant: UNIVERSITY OF WASHINGTON, Seattle, WA (US)

(72) Inventors: Georg Seelig, Seattle, WA (US); Alexander B. Rosenberg, Seattle, WA (US); Charles Roco, Seattle, WA (US)

(73) Assignee: UNIVERSTY OF WASHINGTON, Seattle, WA (US)

(*) Notice: Subject to any disclaimer, the term of this patent is extended or adjusted under 35 U.S.C. 154(b) by 0 days.

This patent is subject to a terminal disclaimer.

(21) Appl. No.: 18/389,901

(22) Filed: Dec. 20, 2023

(65) Prior Publication Data

US 2024/0240233 A1 Jul. 18, 2024

Related U.S. Application Data

(63) Continuation of application No. 18/304,695, filed on Apr. 21, 2023, which is a continuation of application No. 16/649,601, filed as application No. PCT/US2018/052283 on Sep. 21, 2018, now Pat. No. 11,680,283.

(60) Provisional application No. 62/561,806, filed on Sep. 22, 2017.

(51) Int. Cl.
C12Q 1/6806 (2018.01)

(52) U.S. Cl.
CPC ..... *C12Q 1/6806* (2013.01); *C12Q 2521/107* (2013.01); *C12Q 2525/161* (2013.01); *C12Q 2543/101* (2013.01); *C12Q 2563/179* (2013.01); *C12Q 2563/185* (2013.01); *C12Q 2565/514* (2013.01)

(58) Field of Classification Search
CPC ............................ C12Q 1/68; C12Q 2521/107
See application file for complete search history.

(56) References Cited

U.S. PATENT DOCUMENTS

| | | | |
|---|---|---|---|
| 1,002,316 A | 9/1911 | Richardson | |
| 5,962,272 A | 10/1999 | Chenchik | |
| 6,197,554 B1 | 3/2001 | Lin et al. | |
| 6,673,562 B2 | 1/2004 | Shi | |
| 8,673,562 B2 | 3/2014 | Drmanac | |
| 8,771,957 B2 | 7/2014 | Drmanac | |
| 8,835,358 B2 | 9/2014 | Fodor et al. | |
| 8,871,686 B2 | 10/2014 | Ghadessy | |
| 9,074,204 B2 | 7/2015 | Anderson | |
| 9,290,808 B2 | 3/2016 | Fodor et al. | |
| 9,315,857 B2 | 4/2016 | Fu et al. | |
| 9,506,918 B2 | 11/2016 | Fischer | |
| 9,555,137 B2 | 1/2017 | Chiosis et al. | |
| 9,637,784 B2 | 5/2017 | Drmanac | |
| 9,708,659 B2 | 7/2017 | Fodor et al. | |
| 9,727,810 B2 | 8/2017 | Fodor | |
| 9,816,137 B2 | 11/2017 | Fodor et al. | |
| 9,845,502 B2 | 12/2017 | Fodor et al. | |
| 10,002,316 B2 | 6/2018 | Fodor | |
| 10,144,950 B2 | 12/2018 | Nolan | |
| 10,155,981 B2 | 12/2018 | Brenner et al. | |
| 10,240,197 B1 | 3/2019 | Brenner et al. | |
| 10,280,459 B1 | 5/2019 | Brenner et al. | |
| 10,626,442 B2 | 4/2020 | Nolan | |
| 10,697,013 B1 | 6/2020 | Brenner et al. | |
| 10,900,065 B2 * | 1/2021 | Seelig | C12Q 1/6806 |
| 10,982,256 B2 | 4/2021 | Nolan | |
| 10,982,271 B2 | 4/2021 | Bava et al. | |
| 10,995,362 B2 | 5/2021 | Dallett et al. | |
| 11,168,355 B2 * | 11/2021 | Seelig | C12Q 1/6855 |
| 11,214,794 B2 | 1/2022 | Nolan | |
| 11,390,852 B2 | 7/2022 | Ghaedi et al. | |
| 11,512,341 B1 | 11/2022 | Nolan | |
| 11,555,216 B2 | 1/2023 | Seelig et al. | |
| 11,560,585 B2 | 1/2023 | Nolan | |
| 11,566,278 B2 | 1/2023 | Nolan | |
| 11,634,752 B2 | 4/2023 | Nolan | |
| 11,667,956 B2 | 6/2023 | Nolan | |
| 11,680,283 B2 * | 6/2023 | Seelig | C12Q 1/6806 435/6.1 |
| 11,692,214 B2 | 7/2023 | Nolan | |
| 11,708,599 B2 | 7/2023 | Nolan | |

(Continued)

FOREIGN PATENT DOCUMENTS

EP 3234602 10/2017
JP 2014-527620 A 10/2014

(Continued)

OTHER PUBLICATIONS

Lake et al. Neuronal subtypes and diversity revealed by single-nucleus RNA sequencing of the human brain. Science 352 (6293) : p. 1586-1590 (Year: 2016).*

Steiner et al., Cell-type-specific nuclei purification from whole animals for genome-wide expression and chromatin profiling. Genome Research 22 : pp. 766-777 (Year: 2012).*

Lee, M-C. W. et al., "Single-cell analyses of transcriptional heterogeneity during drug tolerance transition in cancer cells by RNA sequencing," PNAS; published online Oct. 22, 2014; E4726-E4735.

(Continued)

*Primary Examiner* — Ethan C Whisenant
(74) *Attorney, Agent, or Firm* — Christensen O'Connor Johnson Kindness

(57) ABSTRACT

Methods of uniquely labeling or barcoding molecules within a nucleus, a plurality of nuclei, a cell, a plurality of cells, and/or a tissue are provided. Kits for uniquely labeling or barcoding molecules within a nucleus, a plurality of nuclei, a cell, a plurality of cells, and/or a tissue are also provided. The molecules to be labeled may include, but are not limited to, RNAs and/or cDNAs.

30 Claims, 25 Drawing Sheets
Specification includes a Sequence Listing.

(56) References Cited

U.S. PATENT DOCUMENTS

| | | | |
|---|---|---|---|
| 11,732,290 | B2 | 8/2023 | Nolan |
| 11,781,171 | B1 | 10/2023 | Nolan |
| 2001/0049094 | A1 | 12/2001 | Alland et al. |
| 2004/0137417 | A1 | 7/2004 | Ryan |
| 2005/0176068 | A1 | 8/2005 | Emmert-Buck |
| 2006/0034826 | A1 | 2/2006 | Carreno |
| 2011/0257031 | A1 | 10/2011 | Bodeau et al. |
| 2012/0220494 | A1 | 8/2012 | Samuels |
| 2013/0274117 | A1 | 10/2013 | Church |
| 2014/0087378 | A1 | 3/2014 | Chatre et al. |
| 2014/0099637 | A1 | 4/2014 | Nolan et al. |
| 2014/0256597 | A1 | 9/2014 | He |
| 2014/0309118 | A1 | 10/2014 | Bang |
| 2014/0309119 | A1 | 10/2014 | Jacobson |
| 2015/0018236 | A1 | 1/2015 | Green et al. |
| 2015/0072869 | A1 | 3/2015 | Vilfan et al. |
| 2015/0298091 | A1 | 10/2015 | Weitz et al. |
| 2015/0299784 | A1* | 10/2015 | Fan .................... C12N 15/1075 506/4 |
| 2015/0329852 | A1 | 11/2015 | Nolan |
| 2016/0001248 | A1 | 1/2016 | Fan |
| 2016/0108458 | A1 | 4/2016 | Frei et al. |
| 2016/0115471 | A1 | 4/2016 | Kim |
| 2016/0122753 | A1 | 5/2016 | Mikkelsen et al. |
| 2016/0138086 | A1* | 5/2016 | Seelig .................. C12Q 1/6806 506/26 |
| 2016/0194699 | A1 | 7/2016 | Borodina |
| 2016/0251697 | A1 | 9/2016 | Nolan |
| 2016/0312276 | A1* | 10/2016 | Fu ........................ C12Q 1/6855 |
| 2016/0378916 | A1 | 12/2016 | Drmanac |
| 2017/0009274 | A1 | 1/2017 | Abate |
| 2017/0204151 | A1* | 7/2017 | Prockop ............... C12Q 1/6886 |
| 2017/0233722 | A1 | 8/2017 | Seelig |
| 2017/0321251 | A1 | 11/2017 | Nolan |
| 2017/0335369 | A1 | 11/2017 | Fields et al. |
| 2017/0362642 | A1 | 12/2017 | Nolan |
| 2018/0135042 | A1 | 5/2018 | Rokhsar |
| 2018/0320241 | A1 | 11/2018 | Nolan |
| 2020/0157603 | A1 | 5/2020 | O'Huallachain et al. |
| 2020/0208197 | A1 | 7/2020 | Nolan |
| 2021/0002733 | A1 | 1/2021 | Nolan |
| 2021/0040538 | A1 | 2/2021 | Nolan |
| 2022/0049286 | A1 | 2/2022 | Dallett et al. |
| 2022/0056515 | A1 | 2/2022 | Bava et al. |
| 2022/0333158 | A1 | 10/2022 | Seelig et al. |
| 2023/0049314 | A1 | 2/2023 | Nolan |
| 2023/0081326 | A1 | 3/2023 | Nolan |
| 2023/0167484 | A1 | 6/2023 | Nolan |
| 2023/0304073 | A1 | 9/2023 | Seelig |
| 2023/0306593 | A1 | 9/2023 | Li |
| 2023/0332215 | A1 | 10/2023 | Chee et al. |
| 2023/0340567 | A1 | 10/2023 | Georg |
| 2024/0240232 | A1 | 7/2024 | Seelig |

FOREIGN PATENT DOCUMENTS

| | | |
|---|---|---|
| JP | 2017-506883 A | 3/2017 |
| WO | 2012129363 | 9/2012 |
| WO | 2014026032 A2 | 2/2014 |
| WO | 2014/144495 A1 | 9/2014 |
| WO | 2014/152397 A1 | 9/2014 |
| WO | 2014137193 | 9/2014 |
| WO | 2014182528 | 11/2014 |
| WO | 2016/100976 A2 | 6/2016 |
| WO | 2016100976 | 6/2016 |
| WO | 2016154177 A | 9/2016 |
| WO | 2016/161023 A1 | 10/2016 |
| WO | 2017044893 | 3/2017 |
| WO | 2017137830 A1 | 8/2017 |
| WO | 2019/236599 A2 | 12/2019 |
| WO | 2012/106385 A2 | 8/2021 |

OTHER PUBLICATIONS

Schlosser, K. and Y. Li, "Tracing Sequence Diversity Change of RNA-Cleaving Deoxyribozymes under Increasing Selection Pressure during in Vitro Selection," Biochemistry 2004, 43, 9695-9707.

Cushman, J. C., "Chapter 9 Isolation of Nuclei Suitable for in Vitro Transcriptional Studies," Science Direct: Methods in Cell Biology, vol. 50, 1995, pp. 113-128.

Kapetyn, J. et al., "Incorporation of non-natural nucleotides into template—switching oligonucleotides reduces background and improves cDNA synthesis from very small RNA samples," BMC Genomics 2010, 11:413, pp. 1-9. <http://www.biomedcentral.com/1471-2164/11/413>.

Wang, E. et al., "High-fidelity mRNA amplification for gene profiling," Nature Biotechnology, vol. 18, Apr. 2000, pp. 457-459. < http:llbiotech.nature.com>.

Zhu, Y. Y. et al., "Reverse Transcriptase Template Switching: A SMART™ Approach for Full-Length cDNA Library Construction," BioTechniques, 30. 892-897 (Apr. 2001).

English translation of the Third Chinese Office Action mailed on Dec. 22, 2023, issued in the corresponding Chinese Application No. 2018800748150, filed on Sep. 21, 2018, 15 pages.

Canadian Requisition by the Examiner mailed on Jan. 29, 2024, issued in the corresponding Canadian Application No. 3,076,367, filed on Sep. 21, 2018, 4 pages.

Eberwine, J. et al., "Analysis of gene expression in single live neurons," Proc. Natl. Acad. Sci. USA, vol. 89. pp. 3010-3014. Apr. 1992, Neurobiology.

Hrvatin, S. et al., "MARIS: Method for Analyzing RNA following Intracellular Sorting," PLoS ONE 9(3): e89459. doi:10.1371/journal.pone.0089459.

O'dell, et al., "Amplification of mRNAs from Single, Fixed, TUNEL-Positive Cells," Oct. 1998, BioTechniques 25: 566-570 (1998).

Sasagawa, Y. et al., "Quartz-Seq: a highly reproducible and sensitive single-cell RNA sequencing method, reveals nongenetic gene-expression heterogeneity," Genome Biology 2013, 14:R31. <http://genomebiology.com/2013/14/4/R31>.

Corrales, J.D. et al., "The level of sonic hedgehog signaling regulates the complexity of cerebellar foliation," Development, 133(9):1811-1821, 2006.

Salero, E. and Hatten, M.E., "Differentiation of ES cells into cerebellar neurons," Proc. Natl. Acad. Sci. USA, 104 (8):2997-3002, Feb. 20, 2007.

D'souza, C.A. et al., "Identification of a set of genes showing regionally enriched expression in the mouse brain," S, MC Neuroscience, 9:66, 14 pages, Jul. 14, 2008.

Tritsch, N.S. et al., "Dopaminergic neurons inhibit striatal output through non-canonical release of GABA," Nature, 190:262-266, Oct. 11, 2012.

Moriyama, M. et al., "Complement Receptor 2 is Expressed in Neural Progenitor Cells and Regulates Adult Hippocampal Neurogenesis," The Journal of Neuroscience, 31 (11):3981-3989, Mar. 16, 2011.

Nielsen, J.V. et al., "Zbtb20-Induced CA1 Pyramidal Neuron Development and Area Enlargement in the Cerebral Midline Cortex of Mice," Cerebral Cortex, 20:1904-1914, Aug. 2010.

Cembrowski, M.S. et al., "Hipposeq: a comprehensive RNA-seq database of gene expression in hippocampal principal neurons," elite, 5:e14997, 22 pages, Apr. 26, 2016.

Thompson, C.L. et al., "A High-Resolution Spatiotemporal Atlas of Gene Expression of the Developing Mouse Brain," Neuron, 83:309-323, Jul. 16, 2014.

Xie, Z. et al., "Zbtb20 is essential for the specification of CA1 field identity in the developing hippocampus," Proc. Natl. Acad. Sci. USA, 107(14):6510-6515, Apr. 6, 2010.

Knight, H.M. et al., "GRIK4/KA1 Protein Expression in Human Brain and Correlation with Bipolar Disorder Risk Variant Status," American Journal of Medical Genetics Part B, Neuropsychiatric Genetics, 159B:21-29, 2012.

Shah, s. et al., "In Situ Transcription Profiling of Single Cells Reveals Spatial Organization of Cells in the Mouse Hippocampus," Neuron, 92:342-357, Oct. 19, 2016.

(56) References Cited

OTHER PUBLICATIONS

Seal, R.P. et al., "Injury-induced mechanical hypersensitivity requires C-low threshold mechanoreceptors," Nature, 462:651-655, Dec. 3, 2009.
Alifragis, P. et al., "Lhx6 Regulates the Migration of Cortical Interneurons from the Ventral Telencephalon But Does Not Specify their GABA Phenotype," The Journal of Neuroscience, 24(24): 5643-5648, Jun. 16, 2004.
Sanchez-Mendoza, E. et al., "Review: Could neurotransmitters influence neurogenesis and neurorepair after stroke?" Neuropathology and Applied Neurobiology, 39:722-735, 2013.
Abraham, H. et al., "p73 and Reelin in Cajal-Retzius Cells of the Developing Human Hippocampal Formation," Cerebral Cortex, 14(5):484-495, May 2004.
Cheung, K-K. et al., "Dynamic expression of Dab2 in the mouse embryonic central nervous system," BMC Developmental Biology, 8:76, 11 pages, Aug. 4, 2008.
Butovsky, O. et al., "Identification of a unique TGF-b-dependent molecular and functional signature in microglia," Nature Neuroscience, 17(1):131-143, Jan. 2014.
Ehmsen, J.T. et al., "The astrocytic transporter SLC7A10 (Asc-1) mediates glycinergic inhibition of spinal cord motor neurons," Scientific Reports, 6:35592, 13 pages, Oct. 19, 2016.
Chuikov, s. et al., "Prdm16 promotes stem cell maintenance in multiple tissues, partly by regulating oxidative stress," Nature Cell Biology, 12(10):999-1006, Oct. 2010.
Afsari, Z.H. et al., "Alteration of Glial Fibrillary Acidic Proteins Immunoreactivity in Astrocytes of the Spinal Cord Diabetic Rats," Anat. Rec. Adv. Integr. Anat. Evol. Biol., 291:390-399, 2008.
Saab, A.S. et al., "Bergmann Glial AMPA Receptors Are Required for Fine Motor Coordination," Science, ~37:749-753, Aug. 10, 2012.
Honore, A. et al., "Isolation, Characterization, and Genetic Profiling of Subpopulations of Olfactory Ensheathing Cells from the Olfactory Bulb," Glia, 60:404-413, 2012.
Murthy, M. et al., "Transcription factor Runx1 inhibits proliferation and promotes developmental maturation in a selected population of inner olfactory nerve layer olfactory ensheathing cells," Gene, 540:191-200, 2014.
Cahoy, J.D. et al., "A Transcriptome Database for Astrocytes, Neurons, and Oligodendrocytes: A New Resource for Understanding Brain Development and Function," The Journal of Neuroscience, 28(1):264-278, Jan. 2, 2008.
Erlander, M.G. and Tobin, AJ., "The Structural and Functional heterogeneity of Glutamic Acid Decarboxylase: A Review," Neurochemical Research, 16(3):215-226, 1991.
Brumovsky, P.R., "VGLUTs in Peripheral Neurons and the Spinal Cord: Time for a Review," ISRN Neurology, 213:829753, 28 pages, 2013.
Fan, H.C. et al., "Combinatorial labeling of single cells for gene expression cytometry," Science, 347(6222):1258367-11258367-8, 628, Feb. 6, 2015.
Lubeck, E. and Cai, L, "Single-cell systems biology by super-resolution imaging and combinatorial labeling," Nature Methods, 9(7):743-748, Jul. 2012.
Japanese Decision for Rejection mailed on Mar. 22, 2023, issued in corresponding Japanese Application No. 2020-516630, filed on Sep. 21, 2018, and English Translation thereof.
Transcriptor One-Step RT-PCR Kit, Roche, Mar. 2009.
European Summons to Oral Proceedings mailed on Mar. 15, 2023, issued in corresponding European Application No. 18858002.1, filed on Sep. 21, 2018, 5 pages.
Islam et al., 2011, "Characterization of the single-cell transcriptional landscape by highly multiplex RNA-seq," 21(7) Genome Research 1160 (May 4, 2011).
Zhong et al., 2011, "High-Throughput Illumina Strand-Specific RNA Sequencing Library Preparation," Cold Spring Harbor Protocols 940 (Aug. 2011).
Zhang et al., 2012, "Strand-specific libraries for high throughput RNA sequencing (RNA-Seq) prepared without poly(A) selection," 3(9) Silence (2012).
Yozwiak et al., 2010, "Human Enterovirus 109: a Novel Interspecies Recombinant Enterovirus Isolated from a Case of Acute Pediatric Respiratory Illness in Nicaragua," 84(18) J. Virology 9047 (Sep. 2010).
Ying et al., 1999, "Generation of Full-Length cDNA Library from Single Human Prostate Cancer Cells," 27(3) Biotechniques 410-14 (published Sep. 1999).
Wuest et al., 2013, "Cell-specific expression profiling of rare cell types as exemplified by its impact on our understanding of female gametophyte development," 16(1) Current Opinion in Plant Biology 41 (2013).
Vo & Jedlicka, 2014, "Protocols for metagenomic DNA extraction and Illumina amplicon library preparation for fecal and swab samples," Molecular Ecology Resources (Apr. 2014).
Vivancos, et al., 2010, "Strand-specific deep sequencing of the transcriptome," 20 Genome Research 989 (Jun. 2, 2010).
Treutlein et al., 2014, Reconstruction lineage hierarchies of the distal lung epithelium using single-cell RNA-seq, 509 Nature 371 (May 15, 2014).
Tang et al., 2009, "mRNA-Seq whole-transcriptome analysis of a single cell," 6(5) Nature Methods 377 (Apr. 6, 2009).
Swaroop & Xu, 1993, cDNA libraries from human tissues and cell lines, 64 Cytogenetic Cell Genetics 292 (1993).
Shimizu et al., 2014, "Qualitative De Novo Analysis of Full Length cDNA and Quantitative Analysis of Gene Expression for Common Marmoset (*Callithrix jacchus*) Transcriptomes Using Parallel Long-Read Technology and Short-Read Sequencing," 9(6) PLoS One e100936 (Jun. 2014).
Schmid et al., 2012, "A Powerful Method for Transcriptional Profiling of Specific Cell Types in Eukaryotes: Laser-Assisted Microdissection and RNA Sequencing," 7(1) PLoS ONE e29685 (Jan. 26, 2012).
Politz & Singer, 1999, "In situ reverse transcription for detection of hybridization between oligonucleotides and their intracellular targets," Methods Jul. 1999;18(3):281-5.
Plessy et al., 2012, "Population transcriptomics with single-cell resolution: A new field made possible by microfluidics," 35(2) Bioessays 131 (2012).
Picelli et al., 2014, "Full-length RNA-seq from single cells using Smart-seq2," Nature Protocols 171 (Jan. 2, 2014).
Miller et al., 2009, "TU-tagging: cell type specific RNA isolation from intact complex tissues," 6(6) Nature Methods 439 (Jun. 2009).
McDavid et al., 2012, "Data exploration, quality control and testing in single-cell qPCR," 29(4) Bioinformatics 461 (Dec. 24, 2012).
Mamanova et al., 2010, "FRT-seq: Amplification-free, strand-specific, transcriptome sequencing," 7(2) Nature Methods 130 (Feb. 2010).
Office Action (Non-Final Rejection) dated Mar. 18, 2024 for U.S. Appl. No. 18/304,670 (pp. 1-7).
Office Action (Notice of Allowance and Fees Due (PTOL-85)) dated Aug. 13, 2024 for U.S. Appl. No. 18/304,670 (pp. 1-8).
Office Action (Notice of Allowance and Fees Due (PTOL-85)) dated Aug. 26, 2024 for U.S. Appl. No. 18/304,670 (pp. 1-3).
Office Action (Notice of Allowance and Fees Due (PTOL-85)) dated Sep. 30, 2024 for U.S. Appl. No. 18/304,670 (pp. 1-3).
Office Action (Notice of Allowance and Fees Due (PTOL-85)) dated Sep. 25, 2024 for U.S. Appl. No. 18/304,695 (pp. 1-3).
Japanese Notice of Reasons for Refusal mailed on Aug. 6, 2024 in the corresponding Japanese Application No. 2023-118356, filed on Sep. 21, 2018; 10 pages.
Cao, Junyue et al., "Comprehensive single cell transcriptional profiling of a multicellular organism by combinatorial indexing," bioRxiv, Cold Spring Harbor Laboratory; Feb. 2, 2017; doi: <hllps://doi.org/10.1101/104844>.
First Chinese Office Action mailed on Nov. 7, 2022, issued in corresponding Chinese Application No. 201880074815.0, filed on Sep. 21, 2018, and English translation thereof, 19 pages.
Adey, el al., In vitro, long-range sequence information for de novo genome assembly via transposase contiguity, Genome Res. 24, 2041-2049, 2014.

(56) References Cited

OTHER PUBLICATIONS

Adey, el al., Rapid, low-input, low-bias construction of shotgun fragment libraries by high-density in vitro transposition Genome Biol. 11, R119, 2010.

Amini, et al., Haplotype-resolved whole-genome sequencing by contiguity-preserving transposition and combinatorial indexing, Nat. Genet. 46, 1343-1349, Dec. 2014.

Boyle, et al., High-Resolution Mapping and Characterization of Open Chromatin Across the Genome, Cell 132, 6110-322, Jan. 25, 2008.

Buenrostro, et al., Transposition of native chromatin for fast and sensitive epigenomic profiling of open chromatin, DNA-binding proteins and nucleosome position, Nat Methods 10, 1213-1218, Dec. 2013.

Casanovich, et al., Multiplex singe-cell profiling of chromatin accessibilty by combinatorial cellular indexing, Science, vol. 348, Issue 6237, pp. 910-914, May 22, 2015.

Deng, et al., Single-Cell RNA-Seq Reveals Dynamic, Random Monoallelic Gene Expression in Mammalian Cells, Science, 343, 193-196, Jan. 10, 2014.

Fu, et al., Counting individual DNA Molecules by the stochastic attachment of diverse labels, Proc Natl Acad Sci. May 31, 2011; 108(22): 9026-31.

Fu, et al., Molecular Indexing Enables quantitative targeted RNA sequencing and reveals poor efficiencies in standard library preparations, Proc Natl Acad Sci. Feb. 4, 2014; 111(5); 1891-1896.

Gole, et al., Massively Parallel Polymerase Cloning and Genome Sequencing of Single Cells Using Nanoliter Microwells, Nat Biotechnol. 31, 1126-1132, Dec. 2013.

Kivioja, et al., Counting absolute numbers of molecules using unique molecular identifiers, Nature Methods, Jan. 2012, vol. 9, No. 1, 72-74.

Matsuda et al. (2011) "Comparison of Fixation Methods for Preservation of Morphology, RNAs, and Proteins From Paraffin-Embedded Human Cancer Cell-Implanted Mouse Models" Journal of Histochemistry & Cytochemistry 59(1) 68-75.

Mortazavi, et al., Mapping and quantifying mammalian transcriptomes by RNA-Seq, Nat Methods 5(7): 621-628, May 30, 2008.

Nagano, et al., "Single-Cell Hi-C Reveals Cell-to-Cell Variability in Chromosome Structure", Nature 502, 59-64, Oct. 3, 2013.

Navin, et al., "Tumour evolution inferred by single-cell sequencing", Nature 472, 90-94, Apr. 7, 2011.

Regev, et al., "The Human Cell Atlas", www.genome.gov/Multimedia/slides/GSPFuture2014/10_Regev.pdf.

Saliba, et al.,"Single-cell RNA-seq: advances and future challenges", Nucleic Acids Res. 42, 8845-8860, Jul. 22, 2014.

Shiroguchi, et al., "Digital RNA sequencing minimizes sequence-dependent bias and amplification noise with optimized single-molecule barcodes", Pree Natl Acad Sci. Jan. 24, 2012; 109(4): 1347-52.

Smallwood, et al., "Single-Cell Genome-Wide Bisulfite Sequencing for Assessing Epigenetic Heterogeneity", Nat. Methods 11, 817-820, Aug. 2014.

Stergachis, et al., "Developmental Fate and Cellular Maturity Encoded in Human Regulatory DNA Landscapes", Cell 154, 888-903 Aug. 15, 2013.

The Encode Project Consortium, et al., "An Integrated encyclopedia of DNA elements in the human genome", Nature 489, 57-74, 2012.

Thurman, et al., "The Accessible Chromatin Landscape of the Human Genome," Nature 489, 75-82, Sep. 6, 2012.

Wu, et al., "Quantitative Assessment of Single-Cell RNA-sequencing methods", Nat. Methods 11, 41-46, Jan. 2014.

Yang, et al., "Global survey of escape from X inactivation by RNA-sequencing in mouse", Genome Res. 20, 614-622, 2010.

Pan, et al., "Single Cell Analysis: from Technology to Biology and Medicine", Single Cell Biol. 3, 106, 2014.

Rotem, et al., "High-Throughput Single-Cell Labeling {Hi-SCL} for RNA-Seq Using Drop-Based Microfluidics", PLoS PNE 10(5): e0116328, May 22, 2015.

Japanese Office Action mailed on Sep. 20, 2022, issued in corresponding Japanese Patent Application No. 2020-516630, filed on Sep. 21, 2018, and English translation thereof, 12 pages.

Rosenberg, A.B. et al., "Single-cell profiling of the developing mouse brain and spinal cord with split-pool barcoding supplementary materials," retrieved from the Internet at https://science.sciencemag.org/contenUsci/suppl/2018/03/14/science.aam8999.DC1/aam8999_Rosenberg_SM.pdf, Apr. 13, 2018, 55 pages.

Extended European Search Report dated May 20, 2021, in corresponding European Patent Application No. 18858002.1, 7 pages.

International Search Report and Written Opinion mailed Mar. 27, 2019, for PCT International Patent Application No. PCT/US2018/052283, filed Sep. 21, 2018, 17 pages.

Cao, J. et al., "Comprehensive single-cell transcriptional profiling of a multicellular organism," Science, 357 6352):661-667, Aug. 18, 2017.

Deangelis, M.M. et al., "Solid-phase reversible immobilization for the isolation of PCR Products," Nucleic Acids Research, 23{22}:4742-4743, 1995.

Picelli, S. et al., "Smart-seq2 for sensitive full-length transcriptome profiling in single cells," Nature Methods, 10:1096-1098, 2013.

Rosenberg, A.B. et al., "Scaling single cell transcriptomics through split pool barcoding," BioRxiv, 2017, available at: https://doi.org/10.1101/105163.

Rosenberg, A.B. et al., "Single-cell profiling of the developing mouse brain and spinal cord with split-pool barcoding," Science, 360{6385):176-182, 2018.

Hashimshony, T. et al., "CEL-Seq: Single-Cell RNA-Seq by Multiplexed Linear Amplification," Cell Reports, 2:666-673, Sep. 27, 2012.

Jaitin, D.A., et al., "Massively Parallel Single-Cell RNA-Seq for Marker-Free Decomposition of Tissues into Cell Types," Science, 343:776-779, Feb. 2014.

Jaitin, et al., Supplementary Material for "Massively Parallel Single-Cell RNA-Seq for Marker-Free Decomposition of Tissues into Cell Types", Published in Science 343, 776-779, Feb. 14, 2014; <www.sciencemag.org/content/343/6172/776/suppIDC1>, including Tables S1-S6 and Supplemental Figures; 399 pages.

Klein, A.M. et al., "Droplet Barcoding for Single-Cell Transcriptomics Applied to Embryonic Stem Cells," Cell, 161:1187-1201, May 21, 2015.

Macosko, E.Z. et al., "Highly Parallel Genome-wide Expression of Profiling of Individual Cells Using Nanoliter Droplets," Cell, 161:1202-1214, May 21, 2015.

Zheng, G.X.Y. et al., "Massively parallel digital transcriptional profiling of single cells," Nature Communications, B:14049 (12 pages), published Jan. 16, 2017.

Tasic, B. et al., "Adult mouse cortical cell taxonomy revealed by single cell transcriptomics," Nature Neuroscience, 19 2):335-346, Feb. 2016.

Zeisel, A. et al., "Cell types in the mouse cortex and hippocampus revealed by single-cell RNA-seq," Science, 347 (6226):1138-1142, Mar. 6, 2015.

Marques, S. et al., "Oligodendrocyte heterogeneity in the mouse juvenile and adult central nervous system," Science, 352(6291):1326-1329, Jun. 10, 2016.

Darmanis, S. et al., "A survey of human brain transcriptome diversity at the single cell level," Proc. Natl. Acad. Sci. USA, 112(23):7285-7290, Jun. 9, 2015.

Lake, B.B. et al., "Neuronal subtypes and diversity revealed by single-nucleus RNA sequencing of the human brain," Science, 352(6293):1586-1590, Jun. 24, 2016.

Shalek, A.K. et al., "Single-cell transcriptomics reveals bimodality in expression and splicing in immune cells," Nature, 498:236-240, Jun. 13, 2013.

Grün, D. et al., "Single-cell messenger RNA sequencing reveals rare intestinal cell types," Nature, 525:251-255, Sep. 10, 2015.

Hesse, K. et al., "AP-25 is a Crucial Transcriptional Regulator of the Posterior Midbrain," PLoS One, 6(8):e23483, 12 pages, Aug. 2011.

Moignard, V. et al., "Decoding the regulatory network of early blood development from single-cell gene expression measurements," Nature Biotechnology, 33(3):269-276, Mar. 2015.

(56) References Cited

OTHER PUBLICATIONS

Venteicher, A.S. et al., "Decoupling genetics, lineages, and microenvironment in IDH-mutant gliomas by single-cell RNA-seq," Science, 335:eaai8478, 1391, Mar. 31, 2017.
Tirosh, I. et al., "Dissecting the multicellular ecosystem of metastatic melanoma by single-cell RNA-seq," Science, 352(6282):189-196, Apr. 8, 2016, corrected Feb. 1, 2019.
Sang, L. et al., "Control of the Reversibility of Cellular Quiescence by the Transcriptional Repressor HES1 ," Science, B21:1095-1100, Aug. 22, 2008.
Zheng, C. et al., "Landscape of Infiltrating T Cells in Liver Cancer Revealed by Single-Cell Sequencing," Cell, 169:1342-1356, Jun. 15, 2017.
Hickman, S.E. et al., "The microglial sensome revealed by direct RNA sequencing," Nature Neuroscience, 16 (12):1896-1905, Dec. 2013.
Matcovitch-Natan, O. et al., "Microglia development follows a stepwise program to regulate brain homeostasis," Science, 353(6301):aad8670-1-aad8670-12, 789, Aug. 19, 2016.
Trapnell, C. et al., "The dynamics and regulators of cell fate decisions are revealed by pseudotemporal ordering of single cells," Nature Biotechnology, 32(4):381-386, Apr. 2014.
Levison, S.W. and Goldman, J.E., "Both Oligodendrocytes and Astrocytes Develop from Progenitors in the Subventricular Zone of Postnatal Rat Forebrain," Neuron, 10:201-212, Feb. 1993.
Lein, E.S. et al., "Genome-wide atlas of gene expression in the adult mouse brain," Nature, 445: 168-176, Jan. 11, 2007.
Iwano, T. et al., "Prox1 postmitotically defines dentate gyrus cells by specifying granule cell identity over CA3 pyramidal cell fate in the hippocampus," Development, 139(16):3051-3062, 2012.
Zhao, C. et al., "Mechanisms and Functional Implications of Adult Neurogenesis," Cell, 132:645-660, Feb. 22, 2008.
Lavado, A. et al., "Prox1 Is Required for Granule Cell Maturation and Intermediate Progenitor Maintenance During Brain Neurogenesis," PLoS Biology, 8(8):e1000460, Aug. 2010.
Bonnet, F. et al., "Structure and Cellular Distribution of Mouse Brain Testican," The Journal of Biological Chemistry, 271(8):4373-4380, Feb. 23, 1996.
Herculano-Houzel, S., "The human brain in Nos. a linearly scaled-up primate brain," Frontiers in Human Neuroscience, 3:31, 11 pages, Nov. 9, 2009.
Nakashima, K. et al., "Cerebellar Granule Cells Are Predominantly Generated by Terminal Symmetric Divisions of Granule Cell Precursors," Developmental Dynamics, 244:748-758, 2015.
Sudarov, A. and Joyner, A.L., "Cerebellum morphogenesis: the foliation pattern is orchestrated by multi-cellular anchoring centers," Neural Development, 2:26, 21 pages, Dec. 3, 2007.
Chang, J.C. et al., "Mitotic Events in Cerebellar Granule Progenitor Cells That Expand Cerebellar Surface Area Are Critical for Normal Cerebellar Cortical Lamination in Mice," J. Neuropathol. Exp. Neural., 74(3):261-272, Mar. 2015.
Schilling, K. et al., "Besides purkinje cells and granule neurons: an appraisal of the cell biology of the interneurons of the cerebellar cortex," Histochem. Cell Biol., 130:601-615, 2008.
Altman, J. and Bayer, SA, "Development of the Precerebellar Nuclei in the Rat: I. The Precerebellar Neuroepithelium of the Rhombencephalon," The Journal of Comparative Neurology, 257:477-489, 1987.
Maricich, S.M. and Herrup, K., "Pax-2 Expression Defines a Subset of GABAergic Interneurons and Their Precursors in the Developing Murine Cerebellum," J. Neurobiol., 41:281-294, 1999.
Weisheit, G. et al., "Postnatal development of the murine cerebellar cortex: formation and early dispersal of basket, Mellate and Golgi neurons," European Journal of Neuroscience, 24:466-478, 2006.
Lalancette-Hebert, M. et al., "Gamma motor neurons survive and exacerbate alpha motor neuron degeneration n ALS," Proc. Natl. Acad. Sci. USA, 113:E8316-E8325, published online Dec. 7, 2016.
Petracca, Y.L. et al., "The late and dual origin of cerebrospinal fluid-contacting neurons in the mouse spinal cord," Development, 143:880-891, 2016.

Enjin, A. et al., "Identification of Novel Spinal Cholinergic Genetic Subtypes Disclose Chodl and Pitx2 as Markers for Fast Motor Neurons and Partition Cells," The Journal of Comparative Neurology, 518:2284-2304, 2010.
Lacar, B. et al., "Nuclear RNA-seq of single neurons reveals molecular signatures of activation," Nature Communications, 7:11022, 13 pages, 2016.
Thomsen, E.R. et al., "Fixed single-cell transcriptomic characterization of human radial glial diversity," Nature Methods, 13(1):87-93, Jan. 2016.
Dobin, A. et al., "STAR: ultrafast universal RNA-seq aligner," Bioinformatics, 29(1):15-21, 2013.
Zorita, E. et al., "Starcode: sequence clustering based on all-pairs search," Bioinformatics, 31(12):1913-1919, 2015.
Yao, Z. et al., "A Single-Cell Roadmap of Lineage Bifurcation in Human ESC Models of Embryonic Brain Development," Cell Stem Cell, 20:120-134, Jan. 15, 2017.
Shekhar, K. et al. "Comprehensive Classification of Retinal Bipolar Neurons by Single-Cell Transcriptomics," Cell, 166:1308-1323, Aug. 25, 2016.
Habib, N. et al., "Div-Seq: Single-nucleus RNA-Seq reveals dynamics of rare adult newborn neurons," Science, 353 (6302):925-928, Aug. 26, 2016.
Pedregosa, F. et al., "Scikit-learn: Machine Learning in Python," Journal of Machine Learning Research, 12:2825-2830, published Oct. 2011.
Van Der Maaten, L., "Accelerating t-SNE using Tree-Based Algorithms," Journal of Machine Learning Research, 15:3221-3245, published Oct. 2014.
Ester, M. et al., "A Density-Based Algorithm for Discovering Clusters -A Density-Based Algorithm for Discovering 3 Clusters in Large Spatial Databases with Noise," Proc. Second Int. Cont. Knowl. Discov. Data Min., pp. 226-231, 1996.
Qiu, X. et al., "Reversed graph embedding resolves complex single-cell trajectories," Nature Methods, 14(10):979-982, Oct. 2017.
Yang, M.J. e t al., "Mitral and Tufted Cells Are Potential Cellular Targets of Nitration in the Olfactory Bulb of Aged Mice," PLoS One, 8(3): e59673, 11 pages, Mar. 2013.
Kawasawa, Y.I. et al., "RNA-seq analysis of developing olfactory bulb projection neurons," Molecular and Cellular Neuroscience, 74:78-86, 2016.
Doyle, J.P. et al., "Application of a Translational Profiling Approach for the Comparative Analysis of CNS Cell Types," Cell, 135:749-762, Nov. 14, 2008.
Alcamo, E.A. et al., "Satb2 Regulates Callosal Projection Neuron Identity in the Developing Cerebral Cortex," Neuron, 57:364-377, Feb. 7, 2008.
Hesse, K. et al., "AP-26 is a Crucial Transcriptional Regulator of the Posterior Midbrain," PLoS One, 6(8):e23483, 12 pages, Aug. 2011.
Valcanis, H. and Tan, S-S., "Layer Specification of Transplanted Interneurons in Developing Mouse Neocortex," Irhe Journal of Neuroscience, 23(12):5113-5122, Jun. 15, 2003.
Ogawa, M. et al., "The reeler Gene-Associated Antigen on Cajal-Retzius Neurons Is a Crucial Molecule for Laminar Organization of Cortical Neurons," Neuron, 14:899-912, May 1995.
He, L. et al., "Analysis of the brain mural cell transcriptome," Scientific Reports, 6:35108, 13 pages, 2016.
Chiu, Y-C. et al., "Foxp2 Regulates Neuronal Differentiation and Neuronal Subtype Specification," Developmental Neurobiology, 74:723-738, 2014.
Miyashita, T. et al., "Neurotrophin-3 Is Involved in the Formation of Apical Dendritic Bundles in Cortical Layer 2 of the Rat," Cerebral Cortex, 20:229-240, Jan. 2010.
Belgard, T .G. et al., "A Transcriptomic Atlas of Mouse Neocortical Layers," Neuron, 71 :605-616, Aug. 25, 2011.
Nagalski, A. et al., "Molecular anatomy of the thalamic complex and the underlying transcription factors," Brain Struct. Funct, 221:2493-2510, 2016.
Wisniewska, M.B. et al., "LEF1/beta-Catenin Complex Regulates Transcription of the Cav3.1 Calcium Channel Gene (Cacna1g) in Thalamic Neurons of the Adult Brain," The Journal of Neuroscience, 30(14): 4957-4969, Apr. 7, 2010.

(56) References Cited

OTHER PUBLICATIONS

Song, H. et al., "Ascl1 and Helt act combinatorially to specify thalamic neuronal identity by repressing Dlxs activation," Developmental Biology, 398:280-291, 2015.

Chinese Decision of Rejection mailed on May 28, 2024, issued in the corresponding Chinese Application No. 201880074815.0, filed on May 19, 2020; 19 pages.

Burton, et al., 2013, "Chromosome-scale scaffolding of de novo genome assemblies based on chromatin interactions," 31(12) Nature Biotechnology 1119 (Nov. 3, 2013).

Cao, et al., 2017, "Comprehensive single cell transcriptional profiling of a multicellular organism by combinatorial indexing," bioRxiv, Cold Spring Harbor Laboratory; Feb. 2, 2017; doi: https://doi.org/10.1101/104844.

Croucher, et al., 2009, "A simple method for directional transcriptome sequencing using Illumina technology," 37(22) Nucleic Acids Research e148 (Oct. 8, 2009).

Eberwine, et al., 2014, "The promise of single-cell sequencing," 11(1) Nat. Methods 25 (Jan. 2014).

Gertz, et al., 2011, "Transposase mediated construction of RNA-seq libraries," 22 Genome Research 134-141 (published Nov. 29, 2011).

Gomez-Lozano, et al., 2012, "Genome-wide identification of novel small RNAs in Pseudomonas aeruginosa," 14(8) Env't Microbiology 2006 (Apr. 2012).

Gupta and Gupta, 2014, "Next Generation Sequencing and Its Applications," Animal Biotechnology. Models in Discovery and Translation (Ashish S. Verma and Anchal Singh, eds., Academic Press, Oxford) (2014).

Islam et al., 2013, "Quantitative single-cell RNA-seq with unique molecular identifiers," Nature Methods (Dec. 22, 2013).

Lee et al., 2014, "Highly Multiplexed Subcellular RNA Sequencing in Situ," 343 Science 1360-1363 (published Feb. 27, 2014).

Ligasova and Koberna, 2010, "In situ reverse transcription: the magic of strength and anonymity," 38(16) Nucleic Acids Research e167 (published Jul. 13, 2010).

Second Chinese Office Action mailed on Jul. 22, 2023, issued in the corresponding Chinese Application No. 201880074815.0, filed on Sep. 21, 2018, and its English translation thereof (21 pages).

U.S. Appl. No. 62/561,806, filed Sep. 22, 2017; Seelig et al.

First Australian Examination Report mailed on Nov. 29, 2023, issued in the corresponding Australian Application No. 2018335876, filed on Sep. 21, 2018, 2 pages.

Extended European Search Report (EESR) mailed on Oct. 28, 2024, issued in the corresponding European U.S. Appl. No. 24/170,361, filed Sep. 21, 2018; 7 pages.

* cited by examiner

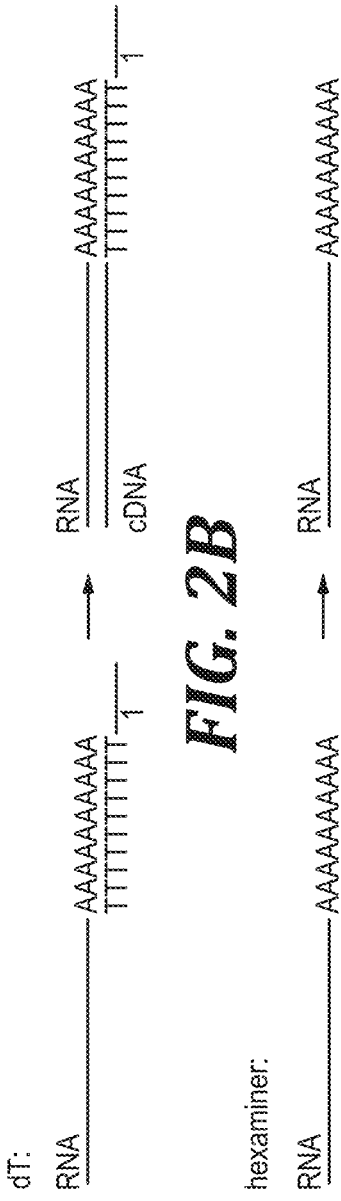
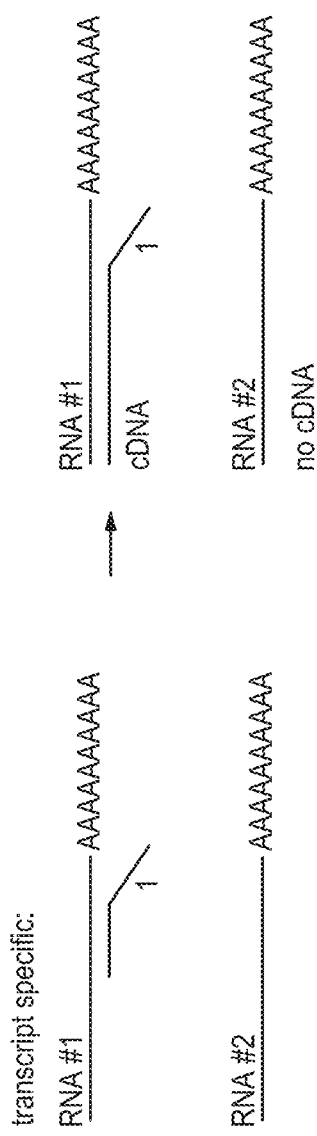
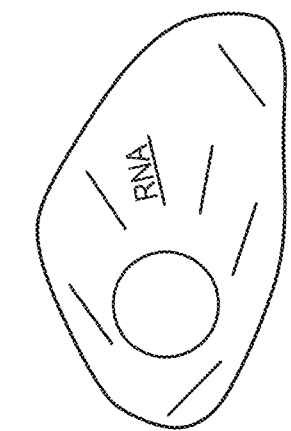
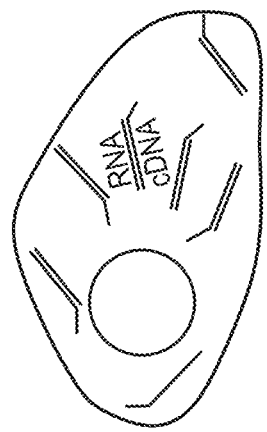
FIG. 2A  FIG. 2B  FIG. 2C  FIG. 2D  FIG. 2E

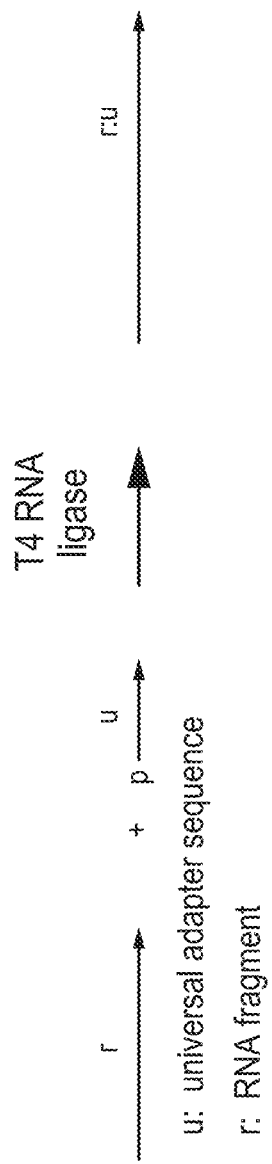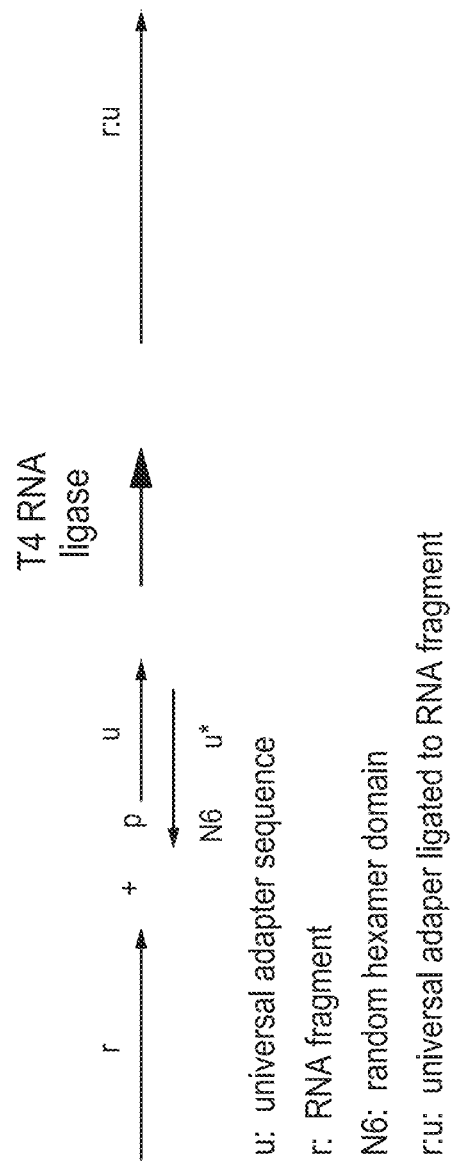
FIG. 3A
FIG. 3B

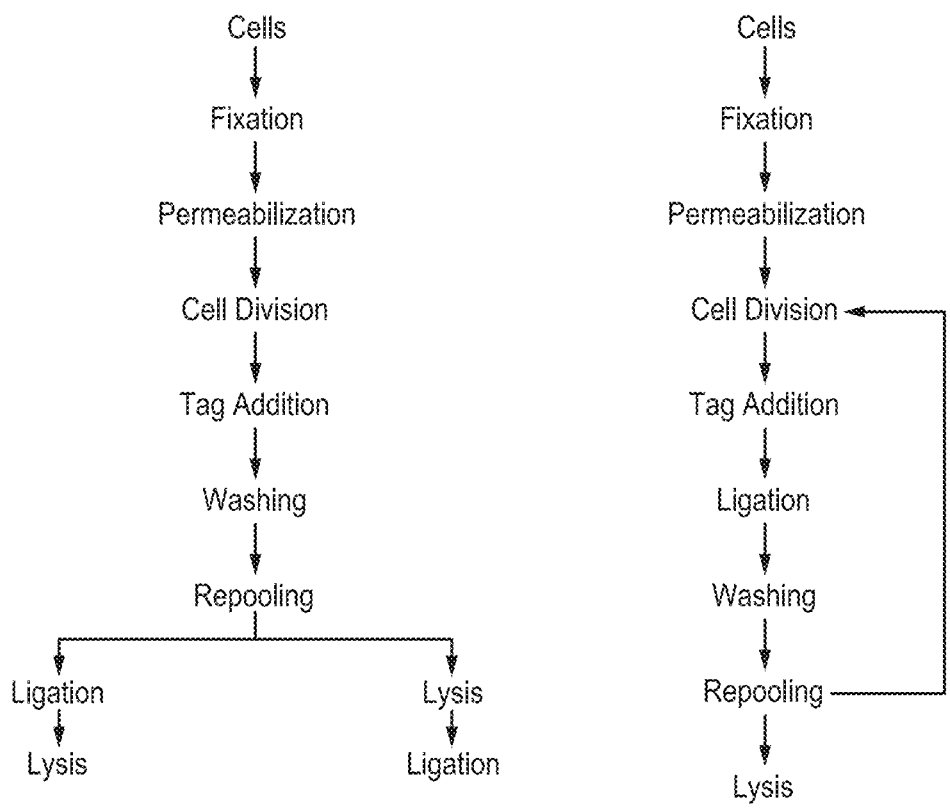
FIG. 9A    FIG. 9B
NBAAAAAAAAAAAAAAAACGAATGCTCTGGCCT (SEQ ID NO:1)
NVTTTTTTTTTTTTTTTGCTTACGAGACCGGA (SEQ ID NO:2)
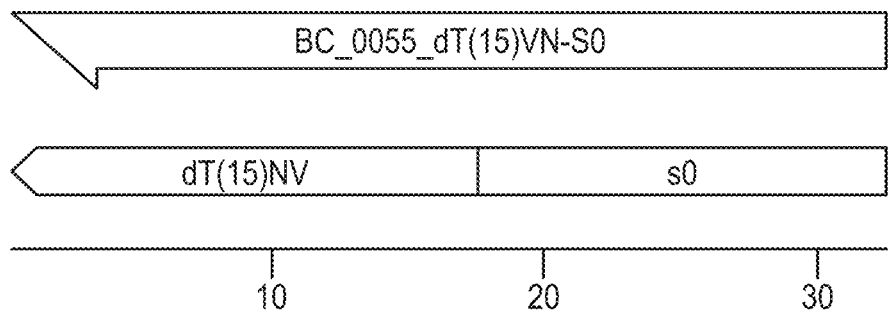
FIG. 10

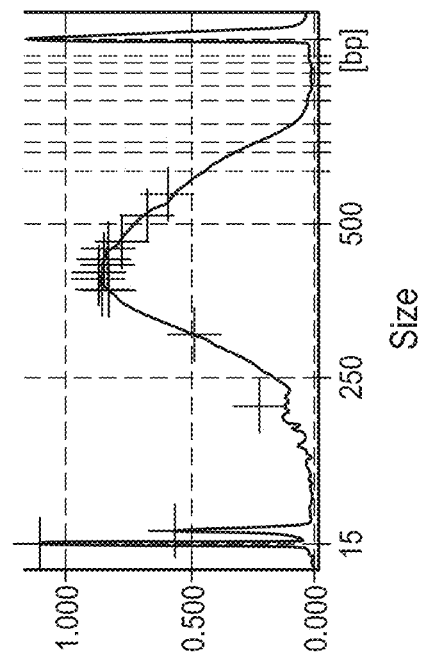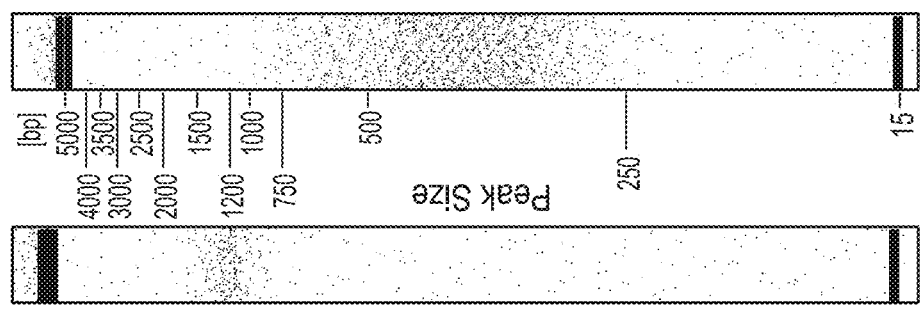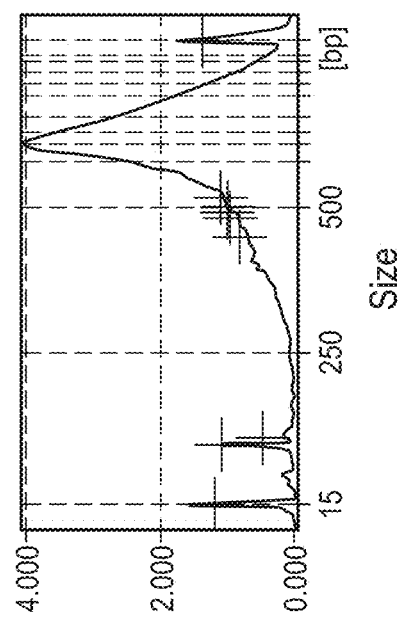
FIG. 19

IN SITU COMBINATORIAL LABELING OF CELLULAR MOLECULES

CROSS-REFERENCE TO RELATED APPLICATIONS

This application is a Track 1 continuation of U.S. application Ser. No. 18/304,695, filed on Apr. 21, 2023, which is a Track 1 continuation of U.S. application Ser. No. 16/649,601, filed Mar. 20, 2020, now issued U.S. Pat. No. 11,680,283, issued on Jun. 20, 2023, which is a national stage entry of International Patent Application No. PCT/US2018/052283, filed Sep. 21, 2018, which claims the benefit of U.S. Provisional Application No. 62/561,806, filed Sep. 22, 2017, which are hereby incorporated by reference in their entirety.

STATEMENT AS TO FEDERALLY SPONSORED RESEARCH

This invention was made with government support under Grant No. R01 CA207029, awarded by the National Institutes of Health. The government has certain rights in the invention.

STATEMENT REGARDING SEQUENCE LISTING

The sequence listing associated with this application is provided in XML format in lieu of a paper copy and is hereby incorporated by reference into the specification. The name of the XML file containing the sequence listing is 3915-P1047USCON4UW_Seq_List_20240408xml. The XML file is 56,755 bytes; was created on Apr. 8, 2024; and is being submitted via Patent Center.

TECHNICAL FIELD

The present disclosure relates generally to methods of uniquely labeling or barcoding molecules within a nucleus, a plurality of nuclei, a cell, a plurality of cells, and/or a tissue. The present disclosure also relates to kits for uniquely labeling molecules within a nucleus, a plurality of nuclei, a cell, a plurality of cells, and/or a tissue. In particular, the methods and kits may relate to the labeling of RNAs and/or cDNAs.

BACKGROUND

Next Generation Sequencing (NGS) can be used to identify and/or quantify individual transcripts from a sample of cells. However, such techniques may be too complicated to perform on individual cells in large samples. In such methods, RNA transcripts are generally purified from lysed cells (i.e., cells that have been broken apart), followed by conversion of the RNA transcripts into complementary DNA (cDNA) using reverse transcription. The cDNA sequences can then be sequenced using NGS. In such a procedure, all of the cDNA sequences are mixed together before sequencing, such that RNA expression is measured for a whole sample and individual sequences cannot be linked back to an individual cell.

Methods for uniquely labeling or barcoding transcripts from individual cells can involve the manual separation of individual cells into separate reaction vessels and can require specialized equipment. An alternative approach to sequencing individual transcripts in cells is to use microscopy to identify individual fluorescent bases. However, this technique can be difficult to implement and limited to sequencing a low number of cells.

BRIEF DESCRIPTION OF THE DRAWINGS

The embodiments disclosed herein will become more fully apparent from the following description and appended claims, taken in conjunction with the accompanying drawings.

FIGS. 2A-2E provide a schematic representation of the formation of cDNA by in situ reverse transcription. FIG. 2A depicts a cell that is fixed and permeabilized. FIG. 2B depicts addition of a poly(T) primer, which can template the reverse transcription of polyadenylated transcripts. FIG. 2C depicts addition of a random hexamer, which can template the reverse transcription of substantially any transcript. FIG. 2D depicts the addition of a primer that is designed to target a specific transcript such that only a subset of transcripts may be amplified. FIG. 2E depicts the cell of FIG. 2A after reverse transcription, illustrating a cDNA hybridized to an RNA.

FIG. 3A depicts non-templated ligation of a single-stranded adapter to an RNA fragment.

FIG. 3B depicts ligation of a single-stranded adapter using a partial duplex with random hexamer primers.

FIG. 9A depicts an exemplary workflow, according to an embodiment of the present disclosure.

FIG. 9B depicts an exemplary workflow, according to another embodiment of the present disclosure.

FIG. 10 depicts a reverse transcription primer (BC_0055), according to an embodiment of the present disclosure.

FIG. 17 also illustrates a region for a sample index, which is GATCTG in this embodiment.

FIG. 19 illustrates the size of cDNA prior to and after tagmentation.

DETAILED DESCRIPTION

Figure 1:
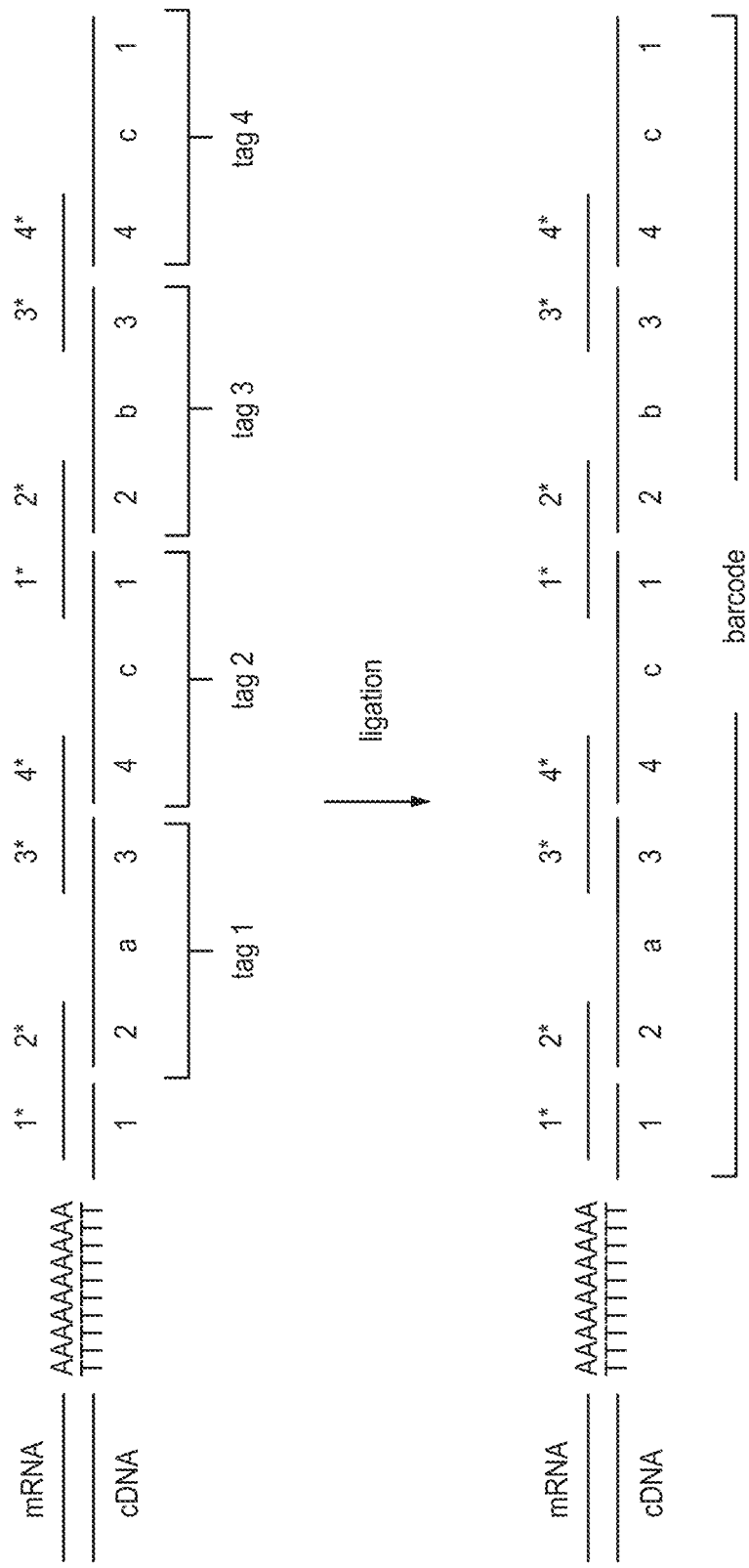
FIG. 1 depicts ligation of nucleic acid tags to form a label or barcode.

The present disclosure relates generally to methods of uniquely labeling or barcoding molecules within a nucleus, a plurality of nuclei, a cell, a plurality of cells, and/or a tissue. The present disclosure also relates to kits for uniquely labeling or barcoding molecules within a nucleus, a plurality of nuclei, a cell, a plurality of cells, and/or a tissue. The molecules to be labeled may include, but are not limited to, RNAs, CDNAs, DNAs, proteins, peptides, and/or antigens.

It will be readily understood that the embodiments, as generally described herein, are exemplary. The following more detailed description of various embodiments is not intended to limit the scope of the present disclosure, but is merely representative of various embodiments. Moreover, the order of the steps or actions of the methods disclosed herein may be changed by those skilled in the art without departing from the scope of the present disclosure. In other words, unless a specific order of steps or actions is required for proper operation of the embodiment, the order or use of specific steps or actions may be modified.

The term "binding" is used broadly throughout this disclosure to refer to any form of attaching or coupling two or more components, entities, or objects. For example, two or more components may be bound to each other via chemical bonds, covalent bonds, ionic bonds, hydrogen bonds, electrostatic forces, Watson-Crick hybridization, etc.

One aspect of the disclosure relates to methods of labeling nucleic acids. In some embodiments, the methods may comprise labeling nucleic acids in a first cell. The methods may comprise: (a) generating complementary DNAs (cDNAs) within a plurality of cells comprising the first cell by reverse transcribing RNAs using a reverse transcription primer comprising a 5' overhang sequence; (b) dividing the plurality of cells into a number (n) of aliquots; (c) providing a plurality of nucleic acid tags to each of the n aliquots, wherein each labeling sequence of the plurality of nucleic acid tags provided into a given aliquot is the same, and wherein a different labeling sequence is provided into each of the n aliquots; (d) binding at least one of the cDNAs in each of the n aliquots to the nucleic acid tags; (e) combining the n aliquots; and (f) repeating steps (b), (c), (d), and (e) with the combined aliquot. In various embodiments, the plurality of cells may be selected from eukaryotic cells and prokaryotic cells. In various other embodiments, the plurality of cells may be selected from, but not limited to, at least one of mammalian cells, yeast cells, and/or bacterial cells.

In certain embodiments, each nucleic acid tag may comprise a first strand including a 3' hybridization sequence extending from a 3' end of a labeling sequence and a 5' hybridization sequence extending from a 5' end of the labeling sequence. Each nucleic acid tag may also comprise a second strand including an overhang sequence. The overhang sequence may include (i) a first portion complementary to at least one of the 5' hybridization sequence and the 5' overhang sequence and (ii) a second portion complementary to the 3' hybridization sequence. In some embodiments, the nucleic acid tag (e.g., the final nucleic acid tag) may comprise a capture agent such as, but not limited to, a 5' biotin. A cDNA labeled with a 5' biotin-comprising nucleic acid tag may allow or permit the attachment or coupling of the cDNA to a streptavidin-coated magnetic bead. In some other embodiments, a plurality of beads may be coated with a capture strand (i.e., a nucleic acid sequence) that is configured to hybridize to a final sequence overhang of a barcode. In yet some other embodiments, cDNA may be purified or isolated by use of a commercially available kit (e.g., an RNEASY™ kit).

In various embodiments, step (f) (i.e., steps (b), (c), (d), and (e)) may be repeated a number of times sufficient to generate a unique series of labeling sequences for the cDNAs in the first cell. Stated another way, step (f) may be repeated a number of times such that the cDNAs in the first cell may have a first unique series of labeling sequences, the cDNAs in a second cell may have a second unique series of labeling sequences, the cDNAs in a third cell may have a third unique series of labeling sequences, and so on. The methods of the present disclosure may provide for the labeling of cDNA sequences from single cells with unique barcodes, wherein the unique barcodes may identify or aid in identifying the cell from which the cDNA originated. In other words, a portion, a majority, or substantially all of the cDNA from a single cell may have the same barcode, and that barcode may not be repeated in cDNA originating from one or more other cells in a sample (e.g., from a second cell, a third cell, a fourth cell, etc.).

In some embodiments, barcoded cDNA can be mixed together and sequenced (e.g., using NGS), such that data can be gathered regarding RNA expression at the level of a single cell. For example, certain embodiments of the methods of the present disclosure may be useful in assessing, analyzing, or studying the transcriptome (i.e., the different RNA species transcribed from the genome of a given cell) of one or more individual cells.

As discussed above, an aliquot or group of cells can be separated into different reaction vessels or containers and a first set of nucleic acid tags can be added to the plurality of cDNA transcripts. Vessels or containers can also be referred to herein as receptacles, samples, and wells. Accordingly, the terms vessel, container, receptacle, sample, and well may be used interchangeably herein. The aliquots of cells can then be regrouped, mixed, and separated again and a second set of nucleic acid tags can be added to the first set of nucleic acid tags. In various embodiments, the same nucleic acid tag may be added to more than one aliquot of cells in a single or given round of labeling. However, after repeated rounds of separating, tagging, and repooling, the cDNAs of each cell may be bound to a unique combination or sequence of nucleic acid tags that form a barcode. In some embodiments, cells in a single sample may be separated into a number of different reaction vessels. For example, the number of reaction vessels may include four 1.5 ml microcentrifuge tubes, a plurality of wells of a 96-well plate, or another suitable number and type of reaction vessels.

In certain embodiments, step (f) (i.e., steps (b), (c), (d), and (e)) may be repeated a number of times wherein the number of times is selected from 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, etc. In certain other embodiments, step (f) may be repeated a sufficient number of times such that the cDNAs of each cell would be likely to be bound to a unique barcode. The number of times may be selected to provide a greater than 50% likelihood, greater than 90% likelihood, greater than 95% likelihood, greater than 99% likelihood, or some other probability that the cDNAs in each cell are bound to a unique barcode. In yet other embodiments, step (f) may be repeated some other suitable number of times.

In some embodiments, the methods of labeling nucleic acids in the first cell may comprise fixing the plurality of cells prior to step (a). For example, components of a cell may be fixed or cross-linked such that the components are immobilized or held in place. The plurality of cells may be fixed using formaldehyde in phosphate buffered saline (PBS). The plurality of cells may be fixed, for example, in about 1-4% formaldehyde in PBS. In various embodiments, the plurality of cells may be fixed using methanol (e.g., 100% methanol) at about −20° C. or at about 25° C. In various other embodiments, the plurality of cells may be fixed using methanol (e.g., 100% methanol), at between about −20° C. and about 25° C. In yet various other embodiments, the plurality of cells may be fixed using ethanol (e.g., about 70-100% ethanol) at about −20° C. or at room temperature. In yet various other embodiments, the plurality of cells may be fixed using ethanol (e.g., about 70-100% ethanol) at between about −20° C. and room temperature. In still various other embodiments, the plurality of cells may be fixed using acetic acid, for example, at about −20° C. In still various other embodiments, the plurality of cells may be fixed using acetone, for example, at about −20° C. Other suitable methods of fixing the plurality of cells are also within the scope of this disclosure.

In certain embodiments, the methods of labeling nucleic acids in the first cell may comprise permeabilizing the plurality of cells prior to step (a). For example, holes or openings may be formed in outer membranes of the plurality of cells. TRITON™ X-100 may be added to the plurality of cells, followed by the optional addition of HCl to form the one or more holes. About 0.2% TRITON™ X-100 may be added to the plurality of cells, for example, followed by the addition of about 0.1 N HCl. In certain other embodiments, the plurality of cells may be permeabilized using ethanol (e.g., about 70% ethanol), methanol (e.g., about 100% methanol), Tween 20 (e.g., about 0.2% Tween 20), and/or NP-40 (e.g., about 0.1% NP-40). In various embodiments, the methods of labeling nucleic acids in the first cell may comprise fixing and permeabilizing the plurality of cells prior to step (a).

In some embodiments, the cells may be adherent cells (e.g., adherent mammalian cells). Fixing, permeabilizing, and/or reverse transcription may be conducted or performed on adherent cells (e.g., on cells that are adhered to a plate). For example, adherent cells may be fixed, permeabilized, and/or undergo reverse transcription followed by trypsinization to detach the cells from a surface. Alternatively, the adherent cells may be detached prior to the separation and/or tagging steps. In some other embodiments, the adherent cells may be trypsinized prior to the fixing and/or permeabilizing steps.

In some embodiments, the methods of labeling nucleic acids in the first cell may comprise ligating at least two of the nucleic acid tags that are bound to the cDNAs. Ligation may be conducted before or after the lysing and/or the cDNA purification steps. Ligation can comprise covalently linking the 5' phosphate sequences on the nucleic acid tags to the 3' end of an adjacent strand or nucleic acid tag such that individual tags are formed into a continuous, or substantially continuous, barcode sequence that is bound to the 3' end of the cDNA sequence. In various embodiments, a double-stranded DNA or RNA ligase may be used with an additional linker strand that is configured to hold a nucleic acid tag together with an adjacent nucleic acid in a "nicked" double-stranded conformation. The double-stranded DNA or RNA ligase can then be used to seal the "nick." In various other embodiments, a single-stranded DNA or RNA ligase may be used without an additional linker. In certain embodiments, the ligation may be performed within the plurality of cells FIG. 1 illustrates ligation of a plurality of nucleic acid tags to form a substantially continuous label or barcode. For example, after a plurality of nucleic acid tag additions, each cDNA transcript may be bound or linked to a series of nucleic acid tags. Use of a ligase may ligate or covalently link a portion of the nucleic acid tags to form a substantially continuous label or barcode that is bound or attached to a cDNA transcript.

In certain other embodiments, the methods may comprise lysing the plurality of cells (i.e., breaking down the cell structure) to release the cDNAs from within the plurality of cells, for example, after step (f). In some embodiments, the plurality of cells may be lysed in a lysis solution (e.g., 10 mM Tris-HCl (pH 7.9), 50 mM EDTA (pH 7.9), 0.2 M NaCl, 2.2% SDS, 0.5 mg/ml ANTI-RNase (a protein ribonuclease inhibitor; AMBION®) and 1000 mg/ml proteinase K (AMBION®)), for example, at about 55° C. for about 1-3 hours with shaking (e.g., vigorous shaking). In some other embodiments, the plurality of cells may be lysed using ultrasonication and/or by being passed through an 18-25 gauge syringe needle at least once. In yet some other embodiments, the plurality of cells may be lysed by being heated to about 70-90° C. For example, the plurality of cells may be lysed by being heated to about 70-90° C. for about one or more hours. The cDNAs may then be isolated from the lysed cells. In some embodiments, RNase H may be added to the cDNA to remove RNA. The methods may further comprise ligating at least two of the nucleic acid tags that are bound to the released cDNAs. In some other embodiments, the methods of labeling nucleic acids in the first cell may comprise ligating at least 3, 4, 5, 6, 7, 8, 9, 10, 11, 12, 13, 14, 15, 16, 17, 18, 19, 20, 21, 22, 23, 24, 25, 30, 35, 40, 45, 50, etc. of the nucleic acid tags that are bound to the cDNAs.

In various embodiments, the methods of labeling nucleic acids in the first cell may comprise removing one or more unbound nucleic acid tags (e.g., washing the plurality of cells). For example, the methods may comprise removing a portion, a majority, or substantially all of the unbound nucleic acid tags. Unbound nucleic acid tags may be removed such that further rounds of the disclosed methods are not contaminated with one or more unbound nucleic acid tags from a previous round of a given method. In some embodiments, unbound nucleic acid tags may be removed via centrifugation. For example, the plurality of cells can be centrifuged such that a pellet of cells is formed at the bottom of a centrifuge tube. The supernatant (i.e., liquid containing the unbound nucleic acid tags) can be removed from the centrifuged cells. The cells may then be resuspended in a buffer (e.g., a fresh buffer that is free or substantially free of unbound nucleic acid tags). In another example, the plurality of cells may be coupled or linked to magnetic beads that are coated with an antibody that is configured to bind the cell or nuclear membrane. The plurality of cells can then be pelleted using a magnet to draw them to one side of the reaction vessel. In some other embodiments, the plurality of cells may be placed in a cell strainer (e.g., a PLURISTRAINER® cell strainer) and washed with a wash buffer. For example, the plurality of cells may remain in the cell strainer while the wash buffer passes through the cell strainer. Wash buffer may include a surfactant, a detergent, and/or about 5-60% formamide.

As discussed above, the plurality of cells can be repooled and the method can be repeated any number of times, adding more tags to the cDNAs creating a set of nucleic acid tags that can act as a barcode. As more and more rounds are added, the number of paths that a cell can take increases and consequently the number of possible barcodes that can be created also increases. Given enough rounds and divisions, the number of possible barcodes will be much higher than the number of cells, resulting in each cell likely having a unique barcode. For example, if the division took place in a 96-well plate, after 4 divisions there would be $96^4=84,934,656$ possible barcodes.

In some embodiments, the reverse transcription primer may be configured to reverse transcribe all, or substantially all, RNA in a cell (e.g., a random hexamer with a 5' overhang). In some other embodiments, the reverse transcription primer may be configured to reverse transcribe RNA having a poly(A) tail (e.g., a poly(dT) primer, such as a dT(15) primer, with a 5' overhang). In yet some other embodiments, the reverse transcription primer may be configured to reverse transcribe predetermined RNAs (e.g., a transcript-specific primer). For example, the reverse transcription primer may be configured to barcode specific transcripts such that fewer transcripts may be profiled per cell, but such that each of the transcripts may be profiled over a greater number of cells.

FIGS. 2A-2E illustrate the formation of cDNA by in situ reverse transcription. FIG. 2A depicts a cell that is fixed and permeabilized. FIG. 2B depicts addition of a poly(T) primer, as discussed above, which can template the reverse transcription of polyadenylated transcripts. FIG. 2C depicts addition of a random hexamer, as discussed above, which can template the reverse transcription of substantially any transcript. FIG. 2D depicts the addition of a primer that is designed to target a specific transcript, as discussed above, such that only a subset of transcripts may be amplified. FIG. 2E depicts the cell of FIG. 2A after reverse transcription, illustrating a cDNA hybridized to an RNA.

Reverse transcription may be conducted or performed on the plurality of cells. In certain embodiments, reverse transcription may be conducted on a fixed and/or permeabilized plurality of cells. In some embodiments, variants of M-MuLV reverse transcriptase may be used in the reverse transcription. Any suitable method of reverse transcription is within the scope of this disclosure. For example, a reverse transcription mix may include a reverse transcription primer including a 5' overhang and the reverse transcription primer may be configured to initiate reverse transcription and/or to act as a binding sequence for nucleic acid tags. In some other embodiments, a portion of a reverse transcription primer that is configured to bind to RNA and/or initiate reverse transcription may comprise one or more of the following: a random hexamer, a septamer, an octomer, a nonamer, a decamer, a poly(T) stretch of nucleotides, and/or one or more gene specific primers.

Another aspect of the disclosure relates to methods of uniquely labeling molecules within a cell or within a plurality of cells. In some embodiments, the method may comprise: (a) binding an adapter sequence, or universal adapter, to molecules within the plurality of cells; (b) dividing the plurality of cells into at least two primary aliquots, wherein the at least two primary aliquots comprise at least a first primary aliquot and a second primary aliquot; (c) providing primary nucleic acid tags to the at least two primary aliquots, wherein the primary nucleic acid tags provided to the first primary aliquot are different from the primary nucleic acid tags provided to the second primary aliquot; (d) binding the adapter sequences within each of the at least two primary aliquots with the provided primary nucleic acid tags; (e) combining the at least two primary aliquots; (f) dividing the combined primary aliquots into at least two secondary aliquots, the at least two secondary aliquots comprising at least a first secondary aliquot and a second secondary aliquot; (g) providing secondary nucleic acid tags to the at least two secondary aliquots, wherein the secondary nucleic acid tags provided to the first secondary aliquot are different from the secondary nucleic acid tags provided to the second secondary aliquot; and (h) binding the molecules within each of the at least two secondary aliquots with the provided secondary nucleic acid tags.

In certain embodiments, the method may further comprise step (i), i.e., repeating steps (e), (f), (g), and (h) with subsequent aliquots. Step (i) can be repeated a number of times sufficient to generate a unique series of nucleic acid tags for the molecules in a single cell. In various embodiments, the number of times may be selected from 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, etc. In certain other embodiments, step (i) may be repeated another suitable number of times.

In some embodiments, the molecules may be disposed within the cell or within the plurality of cells. In some other embodiments, the molecules may be coupled to the cell or to the plurality of cells. For example, the molecules may be cell-surface molecules. In yet some other embodiments, the molecules may be disposed within and/or coupled to the cell or the plurality of cells.

As discussed above, the method may comprise fixing and/or permeabilizing the plurality of cells prior to step (a). In various embodiments, each of the nucleic acid tags may comprise a first strand. The first strand may comprise a barcode sequence including a 3' end and a 5' end. The first strand may further comprise a 3' hybridization sequence and a 5' hybridization sequence flanking the 3' end and the 5' end of the barcode sequence, respectively. In some embodiments, each of the nucleic acid tags may comprise a second strand. The second strand may comprise a first portion complementary to at least one of the 5' hybridization sequence and the adapter sequence and a second portion complementary to the 3' hybridization sequence.

In certain embodiments, the molecules are macromolecules. In various embodiments, the molecules are selected from at least one of RNA, cDNA, DNA, protein, peptides, and/or antigens.

In some embodiments, the molecules are RNA and the adapter sequence may be single-stranded. Furthermore, step (a) may comprise one of ligating a 5' end of the single-stranded adapter sequence to a 3' end of the RNA and/or ligating a 3' end of the single-stranded adapter sequence to a 5' end of the RNA. In some other embodiments, the molecules are RNA and step (a) may comprise hybridizing the adapter sequence to the RNA.

Methods related to binding or coupling an adapter sequence to an RNA can be used, for example, in RNA transcriptome sequencing, ribosome profiling, small RNA sequencing, non-coding RNA sequencing, and/or RNA structure profiling. In some embodiments, the plurality of cells may be fixed and/or permeabilized. The 5' end of a single-stranded adapter sequence may be ligated to the 3' end of an RNA (see FIGS. 3A and 3B). In certain embodiments, the ligation may be conducted or performed by T4 RNA Ligase 1. In certain other embodiments, the ligation may be conducted by T4 RNA Ligase 1 with a single-stranded adapter sequence including a 5' phosphate. In various embodiments, the ligation may be conducted by THERMOSTABLE 5' APPDNA/RNA LIGASE™ (NEW ENGLAND BIOLABS®). In various other embodiments, the ligation may be conducted by THERMOSTABLE 5' APPDNA/RNA LIGASE™ with a 5' pre-adenylated single-stranded adapter sequence. Other suitable ligases and adapter sequences are also within the scope of this disclosure.

Figure 4:
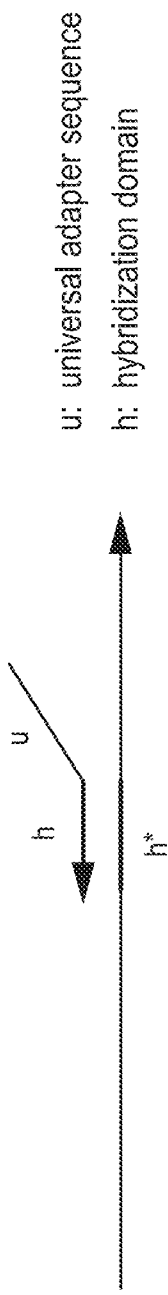
FIG. 4 depicts primer binding.
Figure 5:
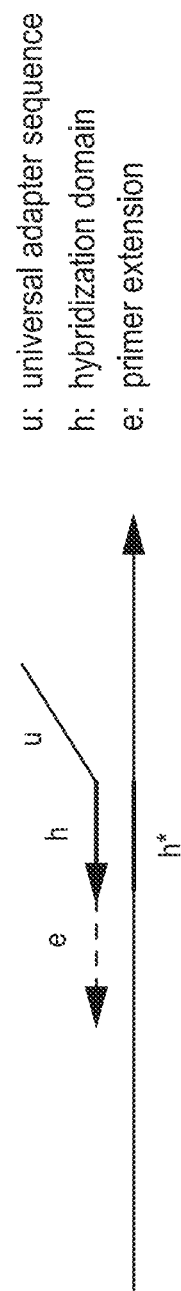
FIG. 5 depicts primer binding followed by reverse transcription.

In some embodiments, the RNA can be labeled with adapter sequence using hybridization, for example, via Watson-Crick base-pairing (see FIG. 4). After the labeling steps and/or cell lysis, as discussed above, the adapter sequence may be configured to prime reverse transcription to form or generate cDNA (see FIG. 5).

The 3' end of a single-stranded adapter sequence may be ligated to the 5' end of an RNA. In certain embodiments, the ligation may be conducted or performed by T4 RNA Ligase 1. In certain other embodiments, the ligation may be conducted by T4 RNA Ligase 1 with an RNA including a 5' phosphate. In various embodiments, the ligation may be conducted by THERMOSTABLE 5' APPDNA/RNA LIGASE™ (NEW ENGLAND BIOLABS®). In various other embodiments, the ligation may be conducted by THERMOSTABLE 5' APPDNA/RNA LIGASE™ with a 5' pre-adenylated RNA. As stated above, other suitable ligases and adapter sequences are also within the scope of this disclosure.

In some embodiments, the molecules may be cDNA. Methods related to binding or coupling an adapter sequence to a cDNA can be used, for example, in RNA transcriptome sequencing. In certain embodiments, the plurality of cells may be fixed and/or permeabilized. Reverse transcription may be performed on the plurality of fixed and/or permeabilized cells with a primer that includes the adapter sequence on the 5' end. As discussed above, the 3' end of the primer may be gene-specific, a random hexamer, or a poly(T) sequence. The resulting cDNA may include the adapter sequence on its 5' end (see FIG. 5).

In some embodiments, wherein the molecules are DNA (e.g., genomic DNA), the method may further comprise digesting the DNA with a restriction enzyme prior to step (a). Furthermore, step (a) may comprise ligating the adapter sequence to the digested DNA.

Methods related to binding or coupling an adapter sequence to a DNA may be used, for example, in whole genome sequencing, targeted genome sequencing, DNase-Seq, ChIP-sequencing, and/or ATAC-seq. In certain embodiments, one or more restriction enzymes may be used to digest DNA into at least one of blunt end fragments and/or fragments having overhang sequences. A partial double-stranded sequence with the single-stranded universal adapter or adapter sequence protruding on one end can be ligated to the digested genomic DNA. For example, a partial double-stranded sequence with the single-stranded adapter sequence having an overhang, wherein the overhang is compatible with the overhang generated by the one or more restriction enzymes, may be ligated to the digested genomic DNA.

In various embodiments, adapter sequences can be integrated (e.g., directly integrated) into genomic DNA using Tn5 transposase and the transposase can be released to expose the adapter sequences by addition of sodium dodecyl sulfate (SDS). Other transposases and methods of integrating the adapter sequences into genomic DNA are also within the scope of this disclosure.

In certain embodiments, the molecules are protein, peptide, and/or antigen, and the adapter sequence may be bound to a unique identifier sequence (e.g., comprising nucleic acids) that is coupled to an antibody. The unique identifier sequence may be configured to uniquely identify the antibody to which the unique identifier sequence is bound. Furthermore, step (a) may comprise binding the antibodies, which comprise each of the adapter sequence and the unique identifier sequence, to the protein, peptide, and/or antigen. In certain other embodiments, the molecules are protein, peptide, and/or antigen, and the adapter sequence may be integrated in an aptamer. Furthermore, step (a) may comprise binding the aptamer to the protein, peptide, and/or antigen.

Figure 6:
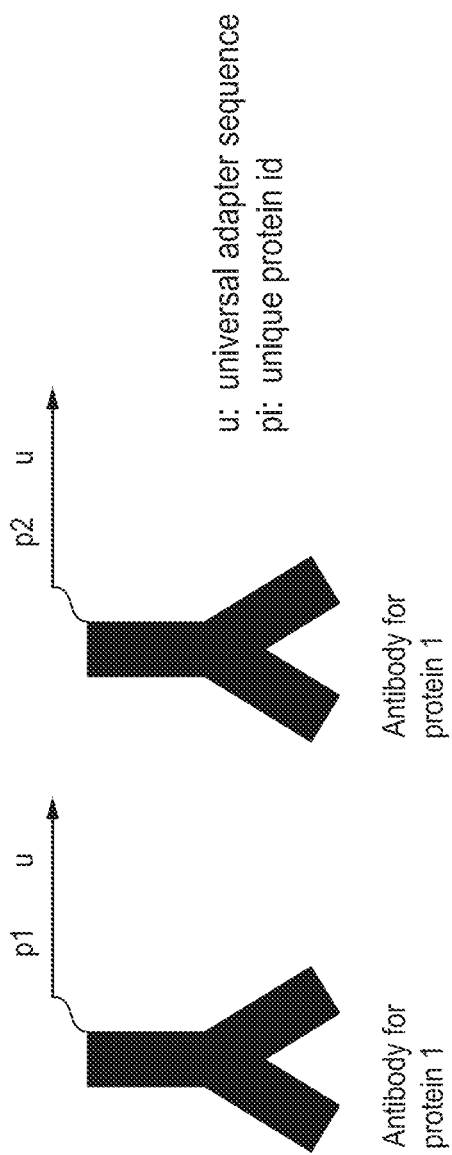
FIG. 6 depicts DNA-tagged antibodies for use in labeling cellular proteins.

Methods related to binding or coupling an adapter sequence to a protein, a peptide, and/or an antigen may be used, for example, in protein quantification, peptide quantification, and/or antigen quantification. In various embodiments, the adapter sequence can be attached (e.g., chemically attached) to an antibody. For example, the adapter sequence can be attached to an antibody using chemistry known to the skilled artisan for mediating DNA-protein bonds. Antibodies for different proteins can be labeled with nucleic acid sequences or strands that include a unique identifier sequence in addition to the adapter sequence. The antibody, or set of antibodies, may then be used in an immunostaining experiment to label a protein, or set of proteins, in fixed and/or permeabilized cells or tissue (see FIG. 6). Subsequently, the cells may undergo a labeling or barcoding procedure as disclosed herein.

In some embodiments, the nucleic acid sequences (e.g., the DNA molecules) attached or bound to the antibodies can be released from the antibodies and/or adapter sequences. A sequencing reaction can reveal a unique identifier sequence associated with a given protein as well as the label or barcode associated with a unique cell or cells. In certain embodiments, such a method may reveal or identify the number and/or type of proteins present in one or more cells.

Figure 7:
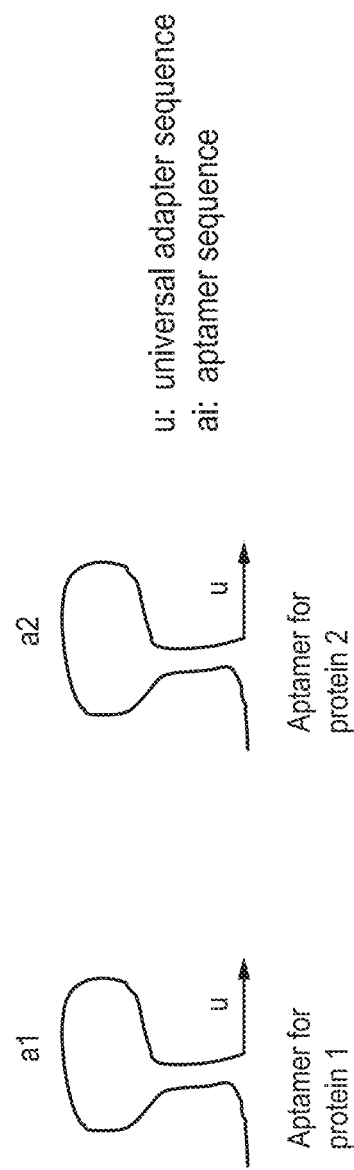
FIG. 7 depicts aptamers for use in labeling cellular proteins.

In various embodiments, a DNA aptamer and/or an RNA aptamer can be used instead of, or in addition to, a nucleic acid-modified (or DNA-modified) antibody as described above (see FIG. 7). The adapter sequence (and target protein-specific antibody) may be integrated (e.g., directly integrated) into the sequence of a given aptamer.

Another aspect of the disclosure relates to methods of barcoding nucleic acids within a cell. In some embodiments, the methods of barcoding nucleic acids within a cell may comprise: (a) generating cDNAs within a plurality of cells by reverse transcribing RNAs using a reverse transcription primer comprising a 5' overhang sequence; (b) dividing the plurality of cells into at least two aliquots; (c) providing a plurality of nucleic acid tags to each of the at least two aliquots, wherein each barcode sequence of the plurality of nucleic acid tags introduced into a given aliquot is the same, and wherein a different barcode sequence is introduced into each aliquot; (d) binding at least one of the cDNAs in each of the at least two aliquots to the nucleic acid tags; (e) combining the at least two aliquots; and (f) repeating steps (b), (c), (d), and (e) at least once with the combined aliquot.

In certain embodiments, each nucleic acid tag may comprise a first strand comprising a 3' hybridization sequence extending from a 3' end of a barcode sequence and a 5' hybridization sequence extending from a 5' end of the barcode sequence. Each nucleic acid tag may also comprise a second strand comprising an overhang sequence, wherein the overhang sequence comprises (i) a first portion complementary to at least one of the 5' hybridization sequence and the 5' overhang sequence and (ii) a second portion complementary to the 3' hybridization sequence.

Figure 8:
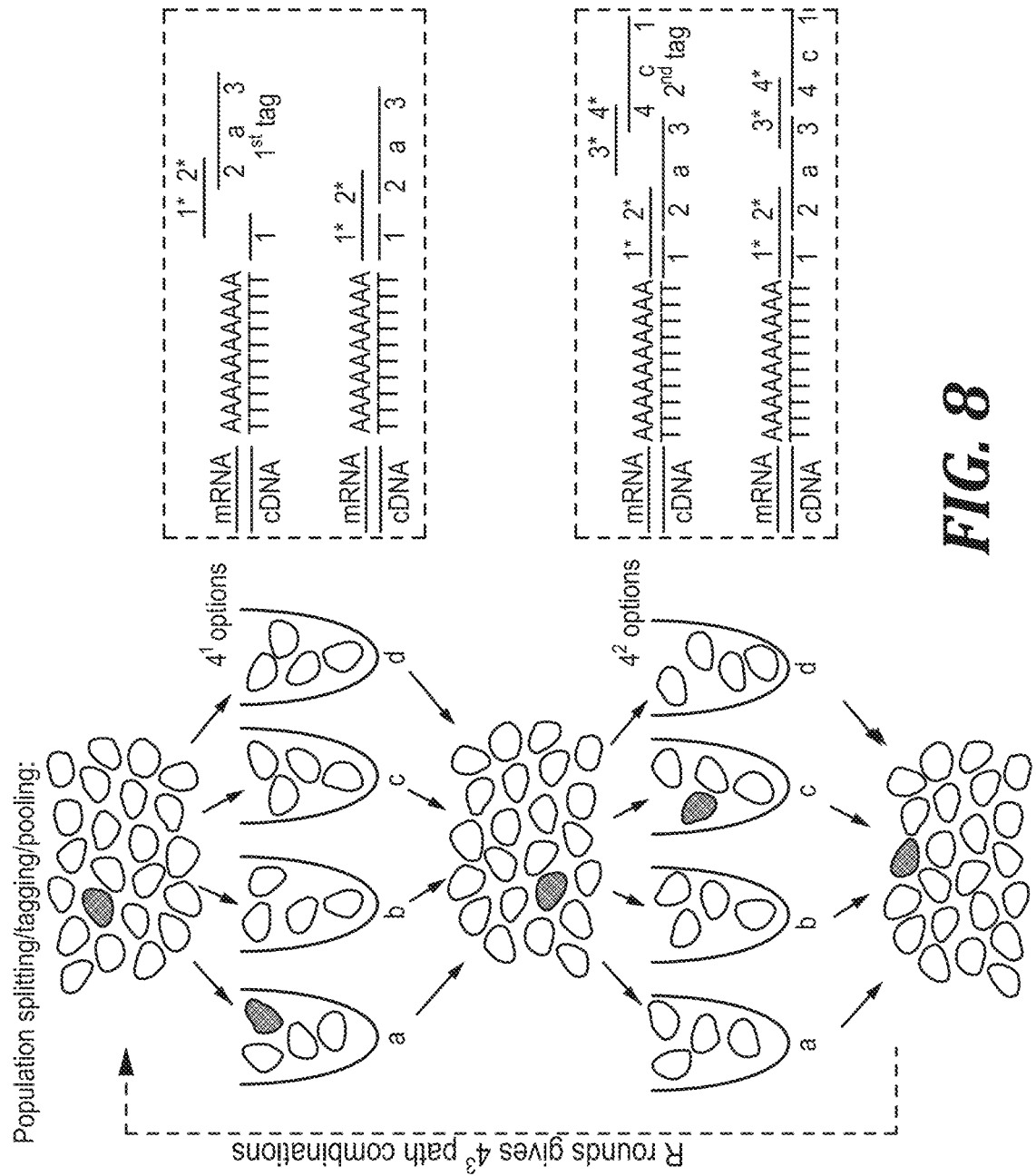
FIG. 8 is a schematic representation of the dividing, tagging, and pooling of cells, according to an embodiment of the present disclosure. As depicted, cells can be divided between a plurality of reaction vessels. One cell is highlighted to show its path through the illustrated process.

FIG. 8 depicts dividing, tagging, and pooling of cells, according to an embodiment of the present disclosure. Cells that have been reverse transcribed can be divided between reaction vessels or wells. In FIG. 8, 4 wells are shown. As discussed above, however, any suitable number of reaction vessels or wells may be used. One cell is highlighted to show its path through the process. As depicted, the highlighted cell first ends up in well 'a', wherein it is the 1$^{st}$ tag added to it that hybridizes to the overhang of all the cDNA transcripts (shown in the box). The tag carries a unique barcode region 'a', identifying the well that the cell was in. After hybridization, all cells are washed to remove excess tags, regrouped, and then split again between the same number of wells. The highlighted cell then ends up in well 'c' and has a 2$^{nd}$ tag added to it identifying the well it was in. After the second round, the cells could have taken $4^2=16$ possible paths through the tubes. The process can be repeated, adding more tags to the cDNA transcripts and increasing the number of possible paths the cells can take. FIGS. 9A and 9B depict two exemplary workflows, according to embodiments of the present disclosure.

Another aspect of the disclosure relates to kits for labeling nucleic acids within at least a first cell. In some embodiments, the kit may comprise at least one reverse transcription primer comprising a 5' overhang sequence. The kit may also comprise a plurality of first nucleic acid tags. Each first nucleic acid tag may comprise a first strand. The first strand may include a 3' hybridization sequence extending from a 3' end of a first labeling sequence and a 5' hybridization sequence extending from a 5' end of the first labeling sequence. Each first nucleic acid tag may further comprise a second strand. The second strand may include an overhang sequence, wherein the overhang sequence may comprise (i) a first portion complementary to at least one of the 5' hybridization sequence and the 5' overhang sequence of the reverse transcription primer and (ii) a second portion complementary to the 3' hybridization sequence.

The kit may further comprise a plurality of second nucleic acid tags. Each second nucleic acid tag may comprise a first strand. The first strand may include a 3' hybridization sequence extending from a 3' end of a second labeling sequence and a 5' hybridization sequence extending from a 5' end of the second labeling sequence. Each second nucleic acid tag may further comprise a second strand. The second strand may comprise an overhang sequence, wherein the overhang sequence may comprise (i) a first portion complementary to at least one of the 5' hybridization sequence and the 5' overhang sequence of the reverse transcription primer and (ii) a second portion complementary to the 3' hybridization sequence. In some embodiments, the first labeling sequence may be different from the second labeling sequence.

In some embodiments, the kit may also comprise one or more additional pluralities of nucleic acid tags. Each nucleic acid tag of the one or more additional pluralities of nucleic acid tags may comprise a first strand. The first strand may include a 3' hybridization sequence extending from a 3' end of a labeling sequence and a 5' hybridization sequence extending from a 5' end of the labeling sequence. Each nucleic acid tag of the one or more additional pluralities of nucleic acid tags may also comprise a second strand. The second strand may include an overhang sequence, wherein the overhang sequence comprises (i) a first portion complementary to at least one of the 5' hybridization sequence and the 5' overhang sequence of the reverse transcription primer and (ii) a second portion complementary to the 3' hybridization sequence. In some embodiments, the labeling sequence may be different in each given additional plurality of nucleic acid tags.

In various embodiments, the kit may further comprise at least one of a reverse transcriptase, a fixation agent, a permeabilization agent, a ligation agent, and/or a lysis agent.

Another aspect of the disclosure relates to kits for labeling molecules within at least a first cell. For example, the kits as disclosed above may be adapted to label one or more of RNA, cDNA, DNA, protein, peptides, or antigens within at least a first cell.

Another aspect of the disclosure relates to methods of uniquely labeling RNA molecules within a plurality of cells. The methods may include: (a) fixing and permeabilizing a first plurality of cells prior to step (b), wherein the first plurality of cells are fixed and permeabilized at below about 8° C.; (b) reverse transcribing the RNA molecules within the first plurality of cells to form complementary DNA (cDNA) molecules within the first plurality of cells, wherein reverse transcribing the RNA molecules includes coupling primers to the RNA molecules, wherein the primers include at least one of a poly(T) sequence or a random sequence; (c) dividing the first plurality of cells including cDNA molecules into at least two primary aliquots, the at least two primary aliquots including a first primary aliquot and a second primary aliquot; (d) providing primary nucleic acid tags to the at least two primary aliquots, wherein the primary nucleic acid tags provided to the first primary aliquot are different from the primary nucleic acid tags provided to the second primary aliquot; (e) coupling the cDNA molecules within each of the at least two primary aliquots with the provided primary nucleic acid tags; (f) combining the at least two primary aliquots; (g) dividing the combined primary aliquots into at least two secondary aliquots, the at least two secondary aliquots including a first secondary aliquot and a second secondary aliquot; (h) providing secondary nucleic acid tags to the at least two secondary aliquots, wherein the secondary nucleic acid tags provided to the first secondary aliquot are different from the secondary nucleic acid tags provided to the second secondary aliquot; (i) coupling the cDNA molecules within each of the at least two secondary aliquots with the provided secondary nucleic acid tags; (j) repeating steps (f), (g), (h), and (i) with subsequent aliquots, wherein the final nucleic acid tags include a capture agent; (k) combining final aliquots; (l)

lysing the first plurality of cells to release the cDNA molecules from within the first plurality of cells to form a lysate; and/or (m) adding a protease inhibitor and/or a binding agent to the lysate such that the cDNA molecules bind the binding agent.

The method may further include dividing the combined final aliquots into at least two final aliquots, the at least two final aliquots including a first final aliquot and a second final aliquot. In some embodiments, the first plurality of cells may be fixed and permeabilized at below about 8° C., below about 7° C., below about 6° C., below about 5° C., at about 4° C., below about 4° C., below about 3° C., below about 2° C., below about 1° C., or at another suitable temperature. In certain embodiments, the methods may include splitting the cells. For example, following the last or final round of barcoding (via ligation), the cells can be pooled before lysis and then the cells can be split into different lysate aliquots. Each lysate aliquot may include a predetermined number of cells.

With reference, for example, to step (m), the protease inhibitor may include phenylmethanesulfonyl fluoride (PMSF), 4-(2-aminoethyl)benzenesulfonyl fluoride hydrochloride (AEBSF), a combination thereof, and/or another suitable protease inhibitor. With reference, for example, to steps (j), (k), (l), and/or (m), the capture agent may include biotin or another suitable capture agent. Furthermore, the binding agent may include avidin (e.g., streptavidin) or another suitable binding agent.

In certain embodiments, the methods of uniquely labeling RNA molecules within a plurality of cells may further include (e.g., after step (m)): (n) conducting a template switch of the cDNA molecules bound to the binding agent using a template switch oligonucleotide; (o) amplifying the cDNA molecules to form an amplified cDNA molecule solution; and/or (p) introducing a solid phase reversible immobilization (SPRI) bead solution to the amplified cDNA molecule solution to remove polynucleotides of less than about 200 base pairs, less than about 175 base pairs, or less than about 150 base pairs (see DeAngelis, M M, et al. Nucleic Acids Research (1995) 23(22):4742). In other words, the cDNA molecules can be bound to streptavidin beads within a lysate. Template switching of the cDNA molecules attached to the beads can be performed (e.g., to add an adapter to the 3'-end of the cDNA molecules). PCR amplification of the cDNA molecules can then be performed, followed by the addition of SPRI beads to remove polynucleotides of less than about 200 base pairs. The ratio of SPRI bead solution to amplified cDNA molecule solution may be between about 0.9:1 and about 0.7:1, between about 0.875:1 and about 0.775:1, between about 0.85:1 and about 0.75:1, between about 0.825:1 and about 0.725:1, about 0.8:1, or another suitable ratio. Furthermore, the SPRI bead solution may include between about 1 M and 4 M NaCl, between about 2 M and 3 M NaCl, between about 2.25 M and 2.75 M NaCl, about 2.5 M NaCl, or another suitable amount of NaCl. The SPRI bead solution may also include between about 15% w/v and 25% w/v polyethylene glycol (PEG), wherein the molecular weight of the PEG is between about 7,000 g/mol and 9,000 g/mol (PEG 8000). In various embodiments, the SPRI bead solution may include between about 17% w/v and 23% w/v PEG 8000, between about 18% w/v and 22% w/v PEG 8000, between about 19% w/v and 21% w/v PEG 8000, about 20% w/v PEG 8000, or another suitable % w/v PEG 8000.

The methods of uniquely labeling RNA molecules within a plurality of cells may further include adding a common adapter sequence to the 3'-end of the released cDNA molecules. The common adapter sequence can be an adapter sequence that is the same, or substantially the same, for each of the cDNA molecules (i.e., within a given experiment). The addition of the common adapter may be conducted or performed in a solution including up to about 10% w/v of PEG, wherein the molecular weight of the PEG is between about 7,000 g/mol and 9,000 g/mol. In certain embodiments, the common adapter sequence may be added to the 3'-end of the released cDNA molecules by template switching (see Picelli, S, et al. Nature Methods 10, 1096-1098 (2013)).

The step (j) may be repeated a number of times sufficient to generate a unique series of nucleic acid tags for the nucleic acids in a single cell. For example, the number of times can be selected from 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, and 100.

In various embodiments, the primers of step (b) may further include a first specific barcode. Stated another way, the first barcode added to the cDNA molecules in a specific container, mixture, reaction, receptacle, sample, well, or vessel may be predetermined (e.g., specific to the given container, mixture, reaction, receptacle, sample, well, or vessel). For example, 48 sets of different well-specific RT primers may be used (e.g., in a 48-well plate). Accordingly, if there are 48 samples (e.g., cells, tissues, etc.), each sample can get a unique well-specific barcode. However, if there are only four samples, each sample can have 12 different sets of well-specific RT primers. A user can know which 12 correspond to each sample, so the user can recover sample identities. Other numbers of first specific barcodes (or well-specific RT primers) are also within the scope of this disclosure. Such a configuration may allow or provide for the multiplexing of the method as explained further in Example 16.

The methods may further include: (q) reverse transcribing RNA molecules within a second plurality of cells to form cDNA molecules within the second plurality of cells, wherein reverse transcribing the RNA molecules includes coupling specific primers to the RNA molecules, wherein the primers include a second specific barcode and at least one of a poly(T) sequence or a random sequence, wherein the first specific barcode is different from the second specific barcode such that the cDNA molecules from the first plurality of cells can be identified in comparison to the cDNA molecules from the second plurality of cells; (r) dividing the second plurality of cells including cDNA molecules into at least two primary aliquots, the at least two primary aliquots including a first primary aliquot and a second primary aliquot; (s) providing primary nucleic acid tags to the at least two primary aliquots, wherein the primary nucleic acid tags provided to the first primary aliquot are different from the primary nucleic acid tags provided to the second primary aliquot; (t) coupling the cDNA molecules within each of the at least two primary aliquots with the provided primary nucleic acid tags; (u) combining the at least two primary aliquots; (v) dividing the combined primary aliquots into at least two secondary aliquots, the at least two secondary aliquots including a first secondary aliquot and a second secondary aliquot; (w) providing secondary nucleic acid tags to the at least two secondary aliquots, wherein the secondary nucleic acid tags provided to the first secondary aliquot are different from the secondary nucleic acid tags provided to the second secondary aliquot; (x) coupling the cDNA molecules within each of the at least two secondary aliquots with the provided secondary nucleic acid tags; and/or (y) repeating steps (u), (v), (w), and (x) with subsequent aliquots, wherein the final nucleic acid tags include a capture agent.

The steps above (e.g., steps (k), (l), and (m)) as used with the first plurality of cells can also be adapted for use with the second plurality of cells.

In various embodiments, each of the nucleic acid tags may include a first strand, wherein the first strand includes (i) a barcode sequence including a 3' end and a 5' end and (ii) a 3' hybridization sequence and a 5' hybridization sequence flanking the 3' end and the 5' end of the barcode sequence, respectively. Each of the nucleic acid tags may also include a second strand, wherein the second strand includes (i) a first portion complementary to at least one of the 5' hybridization sequence and the adapter sequence and (ii) a second portion complementary to the 3' hybridization sequence.

The methods of uniquely labeling RNA molecules within a plurality of cells may further include ligating at least two (or more) of the nucleic acid tags that are bound to the cDNA molecules. The ligation may be performed within the first plurality of cells.

The methods may further include removing unbound nucleic acid tags. In some embodiments, the methods may include ligating at least two of the nucleic acid tags that are bound to the released cDNA molecules. The majority of the nucleic acid tag-bound cDNA molecules from a single cell may include the same series of bound nucleic acid tags. In various embodiments, the pluralities of cells (e.g., the first and second pluralities of cells) may be selected from at least one of mammalian cells, yeast cells, and bacterial cells.

Another aspect of the disclosure is directed to methods of labeling nucleic acids within a first cell. In certain embodiments, the methods may include: (a) generating cDNA molecules within a plurality of cells including the first cell by reverse transcribing RNAs using at least one of (i) a first reverse transcription primer including a 5' overhang sequence, wherein the first reverse transcription primer is configured to reverse transcribe RNA having a poly(A) tail and/or (ii) a second reverse transcription primer including a 5' overhang sequence and at least one of a random hexamer, a random septamer, a random octomer, a random nonamer, and a random decamer; (b) dividing the plurality of cells into a number (n) of aliquots; (c) providing a plurality of nucleic acid tags to each of the n aliquots; (d) binding at least one of the cDNA molecules in each of the n aliquots to the nucleic acid tags; (e) combining the n aliquots; (f) repeating steps (b), (c), (d), and (e) with the combined aliquot; (g) combining final aliquots; (h) lysing the plurality of cells including the first cell to release the cDNA molecules from within the plurality of cells including the first cell to form a lysate; and/or (i) adding a protease inhibitor and/or a binding agent to the lysate such that the cDNA molecules bind the binding agent.

With reference, for example, to step (c), each nucleic acid tag may include a first strand including (i) a 3' hybridization sequence extending from a 3' end of a labeling sequence and (ii) a 5' hybridization sequence extending from a 5' end of the labeling sequence. Each nucleic acid tag may also include a second strand including an overhang sequence, the overhang sequence including (i) a first portion complementary to at least one of the 5' hybridization sequence and the 5' overhang sequence and (ii) a second portion complementary to the 3' hybridization sequence. In some embodiments, the labeling sequence of the plurality of nucleic acid tags provided into a given aliquot may be the same and a different labeling sequence may be provided into each of the n aliquots.

In certain embodiments, step (f) may be repeated a number of times sufficient to generate a unique series of labeling sequences for the cDNA molecules in the first cell. For example, the number of times may be selected from 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, and 100.

The cDNA molecules may be formed or generated in an aliquot (e.g., a reaction mixture). The concentration of the first reverse transcription primer in the aliquot may be between about 0.5 µM and about 10 µM, between about 1 µM and about 7 µM, between about 1.5 µM and about 4 µM, between about 2 µM and about 3 µM, about 2.5 µM, or another suitable concentration. The concentration of the second reverse transcription primer in the aliquot may be between about 0.5 µM and about 10 µM, between about 1 µM and about 7 µM, between about 1.5 µM and about 4 µM, between about 2 µM and about 3 µM, about 2.5 µM, or another suitable concentration.

In some embodiments, the methods may include fixing the plurality of cells prior to step (a). The plurality of cells may be fixed at below about 8° C., below about 7° C., below about 6° C., below about 5° C., at about 4° C., below about 4° C., below about 3° C., below about 2° C., below about 1° C., or at another suitable temperature. In certain embodiments, the methods may include permeabilizing the plurality of cells prior to step (a). The plurality of cells may be permeabilized at below about 8° C., below about 7° C., below about 6° C., below about 5° C., at about 4° C., below about 4° C., below about 3° C., below about 2° C., below about 1° C., or at another suitable temperature.

The methods of labeling nucleic acids within a first cell may also include ligating at least two of the nucleic acid tags that are bound to the cDNA molecules. In various embodiments, the ligation may be performed within the plurality of cells. The methods may include removing unbound nucleic acid tags. Furthermore, at least one of the first and second reverse transcription primers may reverse transcribe predetermined RNAs or be configured to reverse transcribe predetermined RNAs.

In various embodiments, the final nucleic acid tags may include a capture agent. Furthermore, the methods may include lysing the plurality of cells to release the cDNA molecules from within the plurality of cells after step (f) to form a lysate. The methods may also include adding a protease inhibitor and/or a binding agent to the lysate to isolate the cDNA molecules. As discussed above, the protease inhibitor may include PMSF, AEBSF, a combination thereof, and/or another suitable protease inhibitor. The capture agent may include biotin or another suitable capture agent and the binding agent may include avidin (e.g. streptavidin) or another suitable binding agent.

The methods of labeling nucleic acids within a first cell may also include: (j) conducting a template switch of the cDNA molecules bound to the binding agent; (k) amplifying the cDNA molecules to form an amplified cDNA molecule solution; and (l) introducing an SPRI bead solution to the amplified cDNA molecule solution to remove polynucleotides of less than about 200 base pairs, less than about 175 base pairs, or less than about 150 base pairs. The ratio of SPRI bead solution to amplified cDNA molecule solution may be between about 0.9:1 and about 0.7:1, between about 0.875:1 and about 0.775:1, between about 0.85:1 and about 0.75:1, between about 0.825:1 and about 0.725:1, about 0.8:1, or another suitable ratio.

Furthermore, the SPRI bead solution may include between about 1 M and 4 M NaCl, between about 2 M and 3 M NaCl, between about 2.25 M and 2.75 M NaCl, about 2.5 M NaCl, or another suitable amount of NaCl. The SPRI bead solution may also include between about 15% w/v and 25% w/v PEG, wherein the molecular weight of the PEG is between about 7,000 g/mol and 9,000 g/mol. In various embodiments, the SPRI bead solution may include between about 17% w/v and 23% w/v PEG 8000, between about 18% w/v and 22% w/v PEG 8000, between about 19% w/v and 21% w/v PEG 8000, about 20% w/v PEG 8000, or another suitable % w/v PEG 8000.

The methods of uniquely labeling RNA molecules within a plurality of cells may further include adding a common adapter sequence to the 3'-end of the released cDNA molecules. As discussed above, the addition of the common adapter may be conducted or performed in a solution comprising up to about 10% w/v of PEG, wherein the molecular weight of the PEG is between about 7,000 g/mol and 9,000 g/mol. In certain embodiments, the common adapter sequence may be added to the 3'-end of the released cDNA molecules by template switching.

In certain embodiments, any of the methods described above can be adapted for labeling nucleic acid molecules within a nucleus or plurality of nuclei. For example, the methods may include uniquely labeling RNA molecules within a plurality of nuclei or labeling nucleic acids within a first nucleus.

Another aspect of the disclosure is directed to kits for labeling nucleic acids within a first cell. The kit may include a first reverse transcription primer including a 5' overhang sequence and may be configured to reverse transcribe RNA having a poly(A) tail. The kit may also include a second reverse transcription primer including a 5' overhang sequence and at least one of a random hexamer, a random septamer, a random octomer, a random nonamer, and/or a random decamer.

In some embodiments, the kit can include a plurality of first nucleic acid tags. As discussed above, each first nucleic acid tag may include a first strand including (i) a 3' hybridization sequence extending from a 3' end of a first labeling sequence and (ii) a 5' hybridization sequence extending from a 5' end of the first labeling sequence. Each first nucleic acid tag may also include a second strand including an overhang sequence. The overhang sequence may include (i) a first portion complementary to at least one of the 5' hybridization sequence and the 5' overhang sequence of the first and second reverse transcription primers and (ii) a second portion complementary to the 3' hybridization sequence.

In certain embodiments, the kit can also include a plurality of second nucleic acid tags Each second nucleic acid tag may include a first strand including (i) a 3' hybridization sequence extending from a 3' end of a second labeling sequence and (ii) a 5' hybridization sequence extending from a 5' end of the second labeling sequence. Each second nucleic acid tag may also include a second strand including an overhang sequence. The overhang sequence may include (i) a first portion complementary to at least one of the 5' hybridization sequence and the 5' overhang sequence of the first and second reverse transcription primers and (ii) a second portion complementary to the 3' hybridization sequence. Furthermore, the first labeling sequence may be different from the second labeling sequence.

In various embodiments, the kit can also include a plurality of final nucleic acid tags. Each final nucleic acid tag may include a first strand including (i) a 3' hybridization sequence extending from a 3' end of a final labeling sequence and (ii) a 5' hybridization sequence extending from a 5' end of the final labeling sequence. Each final nucleic acid tag may also include a second strand including an overhang sequence. The overhang sequence may include (i) a first portion complementary to at least one of the 5' hybridization sequence and the 5' overhang sequence of the first and second reverse transcription primers and (ii) a second portion complementary to the 3' hybridization sequence. Each final nucleic acid tag may also include a capture agent. Furthermore, the final labeling sequence may be different from the first and second labeling sequences (and/or any other labeling sequences). In some embodiments, the kit may also include at least one of a reverse transcriptase, a fixation agent, a permeabilization agent, a ligation agent, a lysis agent, a protease inhibitor, and/or any other suitable component.

As will be understood by one of ordinary skill in the art, each embodiment disclosed herein can comprise, consist essentially of, or consist of its particular stated element, step, ingredient, or component. As used herein, the transition term "comprise" or "comprises" means includes, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components, and to those that do not materially affect the embodiment.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e., denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the disclosure (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the disclosure and does not pose a limitation on the scope of the disclosure otherwise claimed. No language in the specification should be construed as indicating any non-claimed element essential to the practice of the disclosure.

Groupings of alternative elements or embodiments of the disclosure disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Definitions and explanations used in the present disclosure are meant and intended to be controlling in any future construction unless clearly and unambiguously modified in the following examples or when application of the meaning renders any construction meaningless or essentially meaningless in cases where the construction of the term would render it meaningless or essentially meaningless, the definition should be taken from Webster's Dictionary, 3rd Edition or a dictionary known to those of ordinary skill in the art, such as the Oxford Dictionary of Biochemistry and Molecular Biology (Ed. Anthony Smith, Oxford University Press, Oxford, 2004).

EXAMPLES

The following examples are illustrative of disclosed methods and compositions. In light of this disclosure, those of skill in the art will recognize that variations of these examples and other examples of the disclosed methods and compositions would be possible without undue experimentation.

Example 1—Fixation and Reverse Transcription

NIH/3T3 (mouse) and Hela-S3 (human) cells can be grown to confluence on two separate 10 cm cell culture plates. The cells can be rinsed twice with 10 ml 1× phosphate buffered saline (PBS), 1 ml of 0.05% trypsin can be added to each plate, and the plates can be incubated at 37° C. for 5 minutes. The cells can be detached by tilting each plate at a 45° angle while pipetting trypsin across the plates, which can be continued until all, or substantially all, of the cells are detached. Each cell line can be transferred into its own 15 ml conical centrifuge tube (FALCON™). 2 ml of Dulbecco's Modified Eagle Medium (DMEM) with 10% fetal bovine serum (FBS) can be added to each tube. The number of cells in each tube can be calculated (e.g., with a hemocytometer or on a flow cytometer). For example, 200 µl of the sample can be transferred from each tube into separate 1.7 ml microcentrifuge tubes (EPPENDORF®) and 100 µl of the sample can be run on an ACCURI™ Flow Cytometer to calculate the cell concentration.

The same number of cells from each tube can be combined into a new single 15 ml conical centrifuge tube (FALCON™), using as many cells as possible. A 5 minute spin can be conducted at 500×g in a 15 ml conical centrifuge tube (FALCON™). It may be helpful to use a bucket centrifuge so that the cells are pelleted at the bottom of the tube rather than on the side of the tube. The liquid can be aspirated without disturbing the cell pellet and the cells can be resuspended in 500 µl of 4% formaldehyde. The cells can then be left at room temperature (i.e., 20-25° C.) for 10 minutes. 1.5 ml of 0.5% TRITON™ X-100 can be added to the tube and mixed gently with a pipette. The tube can them be spun at 500×g for 5 minutes. Again, the liquid can be aspirated without disturbing the pellet and the pellet can be washed twice with 1 ml PBS without resuspending the pellet. If washing disturbs the pellet, the second wash can be skipped. The pellet can then be resuspended in 1 ml 0.1 N HCl and incubated at room temperature for 5 minutes.

2 ml of Tris-HCl (pH 8.0) can be added to a new 15 ml conical centrifuge tube (FALCON™). The fixed cells in HCl, from above, can be transferred to the tube with Tris-HCl so as to neutralize the HCl. The number of cells in the tube can then be calculated as discussed above (e.g., with a hemocytometer or on a flow cytometer). The fixed cells in Tris-HCl can be spun down at 500×g for 5 minutes and the liquid can be aspirated without disturbing the pellet. The pellet can be washed twice with 1 ml RNase-free molecular grade water, without disturbing the pellet. The cells can then be resuspended to a concentration of 2.5 million cells/ml (to do this, the concentration calculated before the last spin step can be used).

A reverse transcription mix can be made (55 µl M-MuLV reverse transcriptase buffer (ENZYMATICS®), 55 µl M-MuLV reverse transcriptase (ENZYMATICS®), 5.5 µl dNTPs (25 mM per base), 3.44 µl RNase inhibitor (ENZYMATICS®, 40 units/µl), 210.4 µl nuclease-free water, and 2.75 µl RT Primer (BC_0055, 100 µM)). In a well of a 24-well cell culture plate, 300 µl of the reverse transcription mix can be combined with 200 µl of the fixed cells (~500,000 cells) and mixed gently by pipetting. The mixture can then be incubated at room temperature for 10 minutes to allow the reverse transcription primer to anneal and the mixture can then be incubated at 37° C. in a humidified incubator overnight (i.e., ~16 hours).

A primer that can be used for reverse transcription (BC_0055) is depicted in FIG. 10. This is an anchored primer, designed to bind the start of a poly(A) tail of a messenger RNA. The primer may be synthesized with all 4 bases at the 3' end (N) and every base except T at the second-most 3' position (V). The primer can also include 15 consecutive dTs. In some embodiments, the primer may include more than 15 dTs. In some other embodiments, the primer may include fewer than 15 dTs. In embodiments wherein the primer includes fewer than 15 dTs, the melting temperature of the primer may be lowered. The domain s0 may not hybridize to messenger RNAs, but may instead provide an accessible binding domain for a linker oligo. The primer also includes a 5' phosphate that can allow ligation of the primer to another oligo by T4 DNA ligase.

Example 2—Preparation of Barcodes

The barcodes were ordered in 96-well plates at 100 µM concentrations. Each barcode was annealed with its corresponding linker oligo (see FIGS. 10-12).

Figure 11:
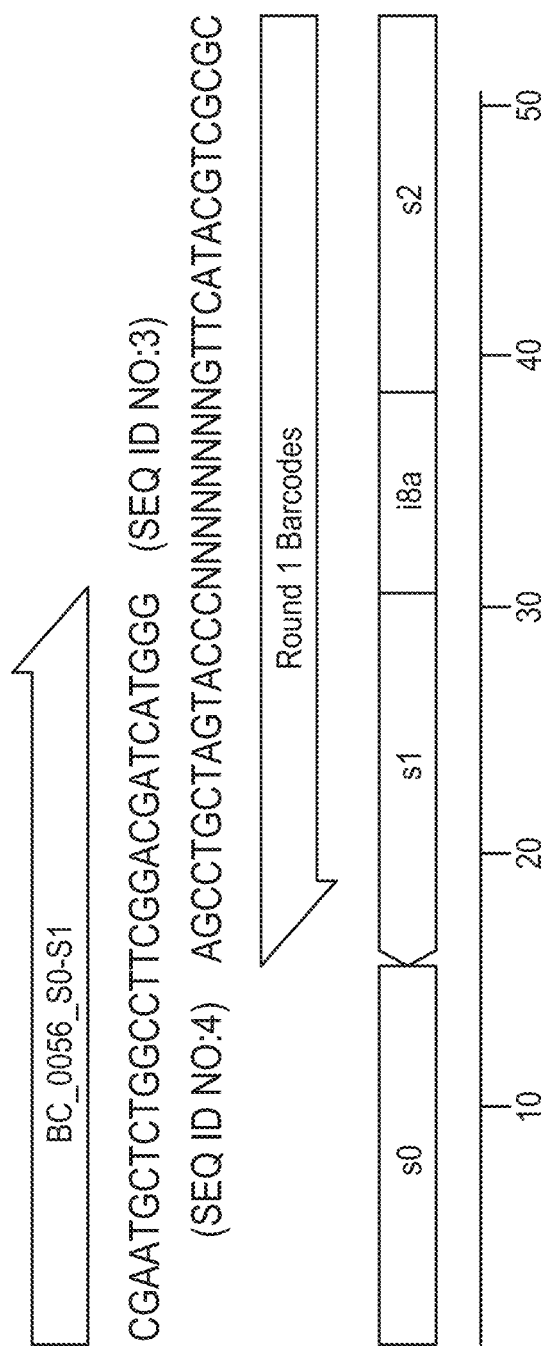
FIG. 11 depicts an annealed, first-round barcode oligo, according to an embodiment of the present disclosure.

FIG. 11 depicts an annealed, first-round barcode oligo. 96 first-round barcode oligos with unique sequences in domain i8a were used. In the first round, the unique sequence in domain i8a is the region of the sequence that is used as a barcode. By varying 8 nucleotides, there are 65,536 possible unique sequences. In some embodiments, more than 8 nucleotides may be present in domain i8a. In some other embodiments, fewer than 8 nucleotides may be present in domain i8a. The first-round barcodes were preannealed to a linker strand (BC_0056) through complementary sequences in domain s1. The linker strand can include complementary sequence to part of the reverse transcription primer (domain s0) that can allow it to hybridize and bring the 3' end of the first-round barcodes in close proximity to the 5' end of the reverse transcription primer. The phosphate of the reverse transcription primer can then be ligated to the 3' end of the first-round barcodes by T4 DNA ligase. The domain s2 can provide an accessible binding domain for a linker oligo to be used in another round of barcoding. The first-round barcode oligos can include a 5' phosphate that can allow ligation to the 3' end of another oligo by T4 DNA ligase.

Figure 12:
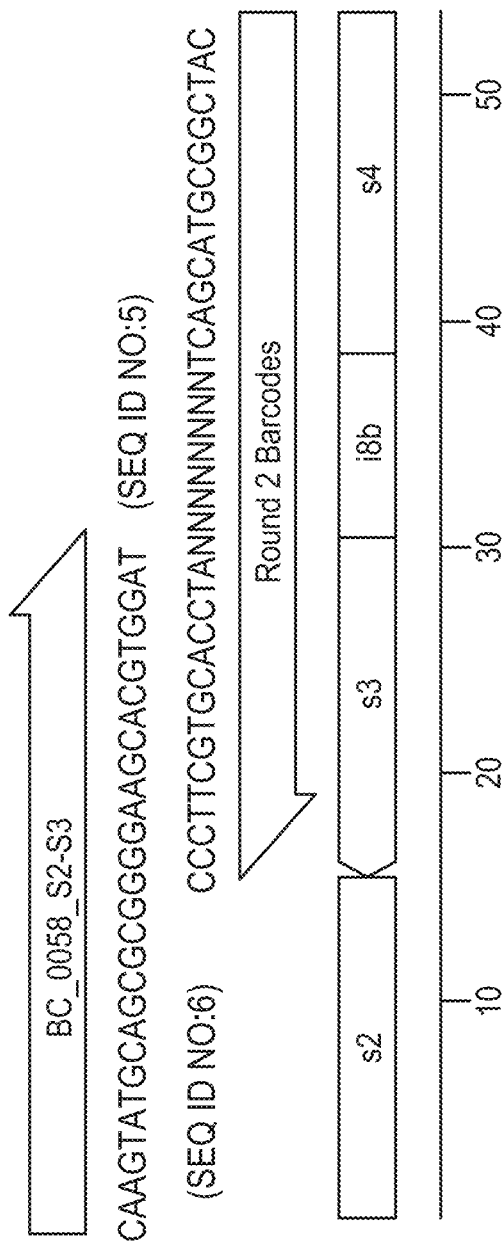
FIG. 12 depicts an annealed, second-round barcode oligo, according to an embodiment of the present disclosure.

FIG. 12 depicts an annealed, second-round barcode oligo. 96 second-round barcode oligos with unique sequences in domain i8b were used. In the second round, the unique sequence in domain i8b is the region of the sequence that is used as a barcode. By varying 8 nucleotides, there are 65,536 possible unique sequences. In some embodiments, more than 8 nucleotides may be present in domain i8b. In some embodiments, less than 8 nucleotides may be present in domain i8b. The second-round barcodes can be preannealed to a linker strand (BC_0058) through complementary sequences in domain s3. The linker strand can include complementary sequence to part of the first-round barcode oligo (domain s2) that can allow it to hybridize and bring the 3' end of the first-round barcodes in close proximity to the 5' end of the second-round barcode oligo. The phosphate of the first-round barcode oligo can then be ligated to the 3' end of the second-round barcodes by T4 DNA ligase. The domain s4 can provide an accessible binding domain for a linker oligo to be used in another round of barcoding. The second-round barcode oligos can include a 5' phosphate that can allow ligation to the 3' end of another oligo by T4 DNA ligase.

Figure 13:
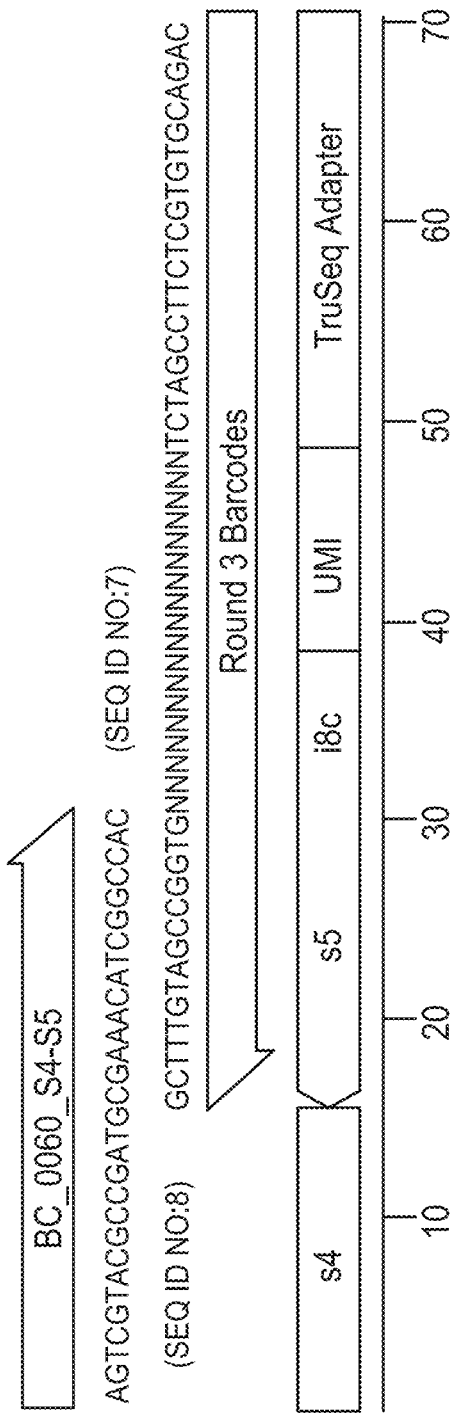
FIG. 13 depicts an annealed, third-round barcode oligo, according to an embodiment of the present disclosure.

FIG. 13 depicts an annealed, third-round barcode oligo. 96 third-round barcode oligos with unique sequences in domain i8c were used. In the third round, the unique sequence in domain i8c is the region of the sequence that is used as a barcode. By varying 8 nucleotides, there are 65,536 possible unique sequences. In some embodiments, more than 8 nucleotides may be present in domain i8c. In some other embodiments, less than 8 nucleotides may be present in domain i8c. The third round of barcodes can be preannealed to a linker strand (BC_0060, SEQ ID NO. 16) through complementary sequences in domain s5. The linker strand can include complementary sequence to part of the second-round barcode oligo (domain s4) that can allow it to hybridize and bring the 3' end of the second-round barcodes in close proximity to the 5' end of the third-round barcode oligo. The phosphate of the second-round barcode oligo can then be ligated to the 3' end of the third-round barcodes by T4 DNA ligase. The third-round barcode oligos can be synthesized with unique molecular identifiers (UMI; see Islam, et. al. Nature Methods, 2014) consisting of 10 random nucleotides (domain UMI: NNNNNNNNNN). Due to PCR amplification bias, multiple sequencing reads can originate from the cDNA. Using a UMI, each cDNA may be counted only once. The third-round barcodes can also include a domain corresponding to part of the ILLUMINA® TruSeq adapter. The third-round barcodes can be synthesized with a biotin molecule at the 5' end so that fully barcoded cDNA can be isolated with streptavidin coated magnetic beads.

Starting from a 100 μM stock of each barcode oligo (i.e., in 96-well plates, one for each round), 11 μl of barcode oligo were transferred to 96-well PCR plates. To the plate with the round 1 barcodes, 9 μl of BC_0056 (100 μM stock) were added to each well. To the plate with the round 2 barcodes, 9 μl of BC_0058 (100 μM stock) were added to each well. To the plate with the round 3 barcodes, 9 μl of BC_0060 (SEQ ID NO. 16) (100 μM stock) were added to each well. Each plate was then placed in a thermocycler, with the following program, to anneal the barcodes with the corresponding linker oligo: heat to 90° C., reduce heat 0.1° C./second, and stop when the temperature reaches 25° C. 2.2 μl were transferred from each well having the round 1 barcodes into a new 96-well plate (referred to as plate L1). 3.8 μl were transferred from each well with the round 2 barcodes into a new 96-well plate (referred to as plate L2). 6.1 μl were transferred from each well with the round 3 barcodes into a new 96-well plate (referred to as plate L3).

Example 3—Preparation of Ligation Stop Oligos

Figure 14:
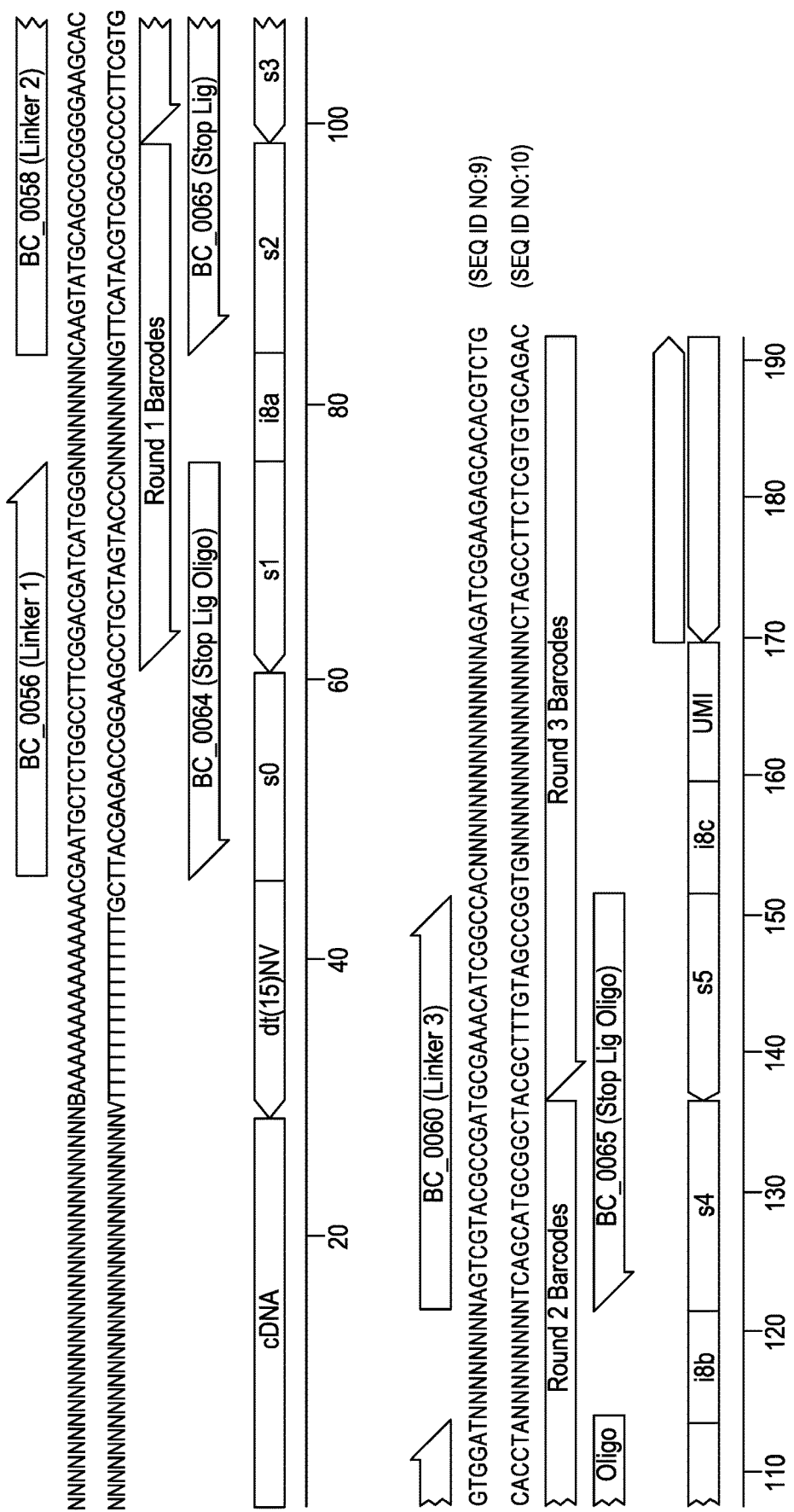
FIG. 14 depicts ligation stop oligos, according to an embodiment of the present disclosure.

After each round of ligation, the ligation can be stopped by adding an excess of oligo that is complementary to the linker strands (see FIG. 14). To stop each barcode ligation, oligo strands that are fully complementary to the linker oligos can be added. These oligos can bind the linker strands attached to unligated barcodes and displace the unligated barcodes through a strand displacement reaction. The unligated barcodes can then be completely single-stranded. As T4 DNA ligase is unable to ligate single-stranded DNA to other single-stranded DNA, the ligation reaction will stop progressing. To ensure that all linker oligos are bound by the complementary oligos, a molar excess of the complementary oligos (relative to the linker oligos) is added. To stop the first-round ligation, BC_0064 (complementary to BC_0056) is added. To stop the second-round ligation, BC_0065 (complementary to BC_0058) is added. To stop the third-round ligation, BC_0066 (SEQ ID NO. 18) (complementary to BC_0060, SEQ ID NO. 16) is added.

Dilutions can be prepared for each stop ligation strand (BC_0064, BC_0065, BC_0066 (SEQ ID NO. 18)) as follows: 264 μl stop ligation strand (BC_0064, BC_0065, BC_0066 (SEQ ID NO. 18)), 300 μl 10× T4 DNA Ligase Buffer, and 636 μl nuclease-free water.

Example 4—Ligation of Barcodes to cDNA

5 μl 10% TRITON™ X-100 can be added to the reverse transcription reaction (to a final concentration of 0.1%) in the above-described 24-well plate. The reverse transcription (RT) reaction with cells can be transferred to a 15 ml conical centrifuge tube (FALCON™). The RT reactions can be spun for 10 minutes at 500×g and resuspended in 2 ml nuclease-free water. The cells can be combined with ligase mix (600 μl 10× T4 ligase buffer, 2040 μl of nuclease-free water, all of the resuspended cells (2000 μl), 100 μl of T4 DNA Ligase (NEW ENGLAND BIOLABS®, 400,000 units/ml), and 60 μl of 10% TRITON™ X-100) in a disposable pipetting reservoir (10 ml)). The cells and ligase mix can be mixed by gently tilting the reservoir back and forth several times. Using a multichannel pipette, 40 μl of the cells in the ligase mix can be added to each well of annealed round 1 barcodes (plate L1). Each well can be mixed by pipetting up and down gently 2-3 times. The cells in the ligase mix can be incubated at 37° C. for 60 minutes.

10 μl of the diluted BC_0064 can be added to each well to stop the ligation. The samples can then be incubated at 37°

C. for 30 minutes. All of the cells can be collected in a new disposable pipetting reservoir (10 ml). The cells can be passed through a 40 µM strainer into a new disposable pipetting reservoir (10 ml) using a 1 ml pipette. 100 µl of T4 DNA ligase (NEW ENGLAND BIOLABS®, 400,000 units/ml) can be added to the cells in reservoir. The cells and ligase mix can be mixed by gently tilting the reservoir back and forth several times and using a multichannel pipette, 40 µl of the cells in the ligase mix can be added to each well of annealed round 2 barcodes (plate L2). Each well can be mixed by pipetting up and down gently 2-3 times and the samples can then be incubated at 37° C. for 60 minutes.

10 µl of the diluted BC_0065 can be added to each well to stop the ligation. The samples can be incubated at 37° C. for 30 minutes and the cells can then be collected in a new disposable pipetting reservoir (10 ml). The cells can be passed through a 40 µM strainer into a new disposable pipetting reservoir (10 ml) using a 1 ml pipette. 100 µl of T4 DNA ligase (NEW ENGLAND BIOLABS®, 400,000 units/ml) can be added to the cells in the reservoir. The cells and ligase mix can be mixed by gently tilting the reservoir back and forth several times. Using a multichannel pipette, 40 µl of the cells in the ligase mix can be added to each well of annealed round 3 barcodes (plate L3). Each well can then be mixed by pipetting up and down gently 2-3 times and the samples can be incubated at 37° C. for 60 minutes.

10 µl of the diluted BC_0066 (SEQ ID NO. 18) can be added to each well to stop the ligation. The samples can be incubated at 37° C. for 30 minutes. All the cells can be collected in a new disposable pipetting reservoir (10 ml). The cells can be transferred to a 15 ml conical centrifuge tube (FALCON™) and the tube can be filled with wash buffer (nuclease-free water, 0.05% Tween 20, and 25% formamide) to 15 ml. The samples can be incubated for 15 minutes at room temperature. The cells can then be pelleted at 500×g for 10 minutes and the liquid can be removed without disturbing the pellet. Each tube of cells can be resuspended in 100 µl PBS and the cells can be counted (e.g., on a hemocytometer or on a flow cytometer). In one example, 57,000 cells were retained. The number of cells to be sequenced can be chosen. In one example, the cells were split into 25 cell, 250 cell, 2,500 cell, and 25,000 cell aliquots. 300 µl of lysis buffer (10 mM NaF, 1 mM $Na_3VO_4$, 0.5% DOC buffer, and 0.5% TRITON™ X-100) can be added to each of the cell aliquots and each of the cell aliquots can be passed through a 25 gauge needle eight times.

Example 5—Binding Barcoded cDNA to Streptavidin Coated Beads

First, DYNABEADS® MYONE™ Streptavidin C1 beads can be resuspended. 20 µl of resuspended DYNABEADS® MYONE™ Streptavidin C1 beads (for each aliquot of cells) can be added to a 1.7 ml microcentrifuge tube (EPPENDORF®). The beads can be washed 3 times with 1× phosphate buffered saline Tween 20 (PBST) and resuspended in 20 µl PBST. 900 µl PBST can be added to the cell aliquot and 20 µl of washed C1 beads can be added to the aliquot of lysed cells. The samples can be placed on a gentle roller for 15 minutes at room temperature and then washed 3 times with 800 µl PBST using a magnetic tube rack (EPPENDORF®). The beads can then be resuspended in 100 µl PBS.

Example 6—RNase Treatment of Beads

A microcentrifuge tube (EPPENDORF®) comprising a sample can be placed against a magnetic tube rack (EPPENDORF®) for 2 minutes and then the liquid can be aspirated. The beads can be resuspended in an RNase reaction (3 µl RNase Mix (ROCHE™), 1 µl RNase H (NEW ENGLAND BIOLABS®), 5 µl RNase H 10× Buffer (NEW ENGLAND BIOLABS®), and 41 µl nuclease-free water). The sample can be incubated at 37° C. for 1 hour, removed from 37° C., and placed against a magnetic tube rack (EPPENDORF®) for 2 minutes. The sample can be washed with 750 µl of nuclease-free water+0.01% Tween 20 ($H_2O$-T), without resuspending the beads and keeping the tube disposed against the magnetic tube rack. The liquid can then be aspirated. The sample can be washed with 750 µl $H_2O$-T without resuspending the beads and while keeping the tube disposed against the magnetic tube rack. Next, the liquid can be aspirated while keeping the tube disposed against the magnetic tube rack. The tube can then be removed from the magnetic tube rack and the sample can be resuspended in 40 µl of nuclease-free water.

Example 7—3' Adapter Ligation

Figure 15:
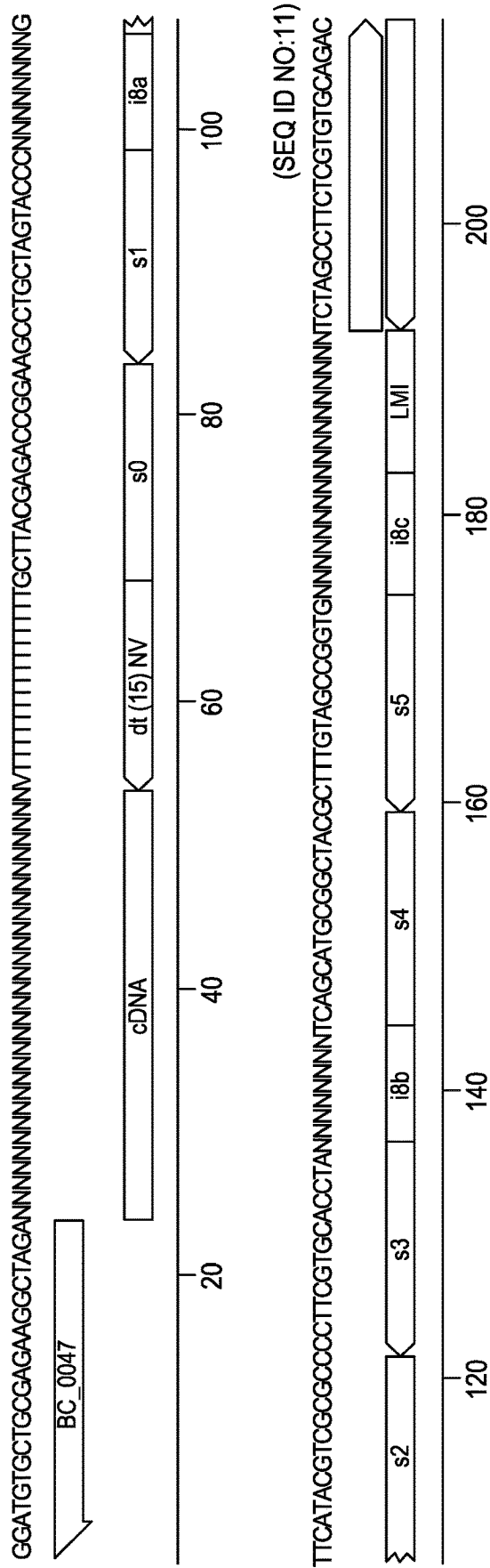
FIG. 15 depicts a single-stranded DNA adapter oligo (BC_0047) ligated to the 3' end of a cDNA, according to an embodiment of the present disclosure.

With reference to FIG. 15, to facilitate PCR amplification, a single-stranded DNA adapter oligo (BC_0047) can be ligated to the 3' end of cDNA. To prevent concatemers of the adapter oligo, dideoxycytidine (ddC) can be included at the 3' end of the adapter oligo. BC_0047 was generated with a phosphate at the 5' end and ddC at the 3' end. Several enzymes are capable of ligating single-stranded oligo to the 3' end of single-stranded DNA. Herein, T4 RNA ligase 1 (NEW ENGLAND BIOLABS®) was used. Thermostable 5' AppDNA/RNA Ligase (NEW ENGLAND BIOLABS®) can also be used with a preadenylated adaptor oligo.

Specifically, 20 µl of the RNase-treated beads can be added to a single PCR tube. 80 µl of ligase mix (5 µl T4 RNA Ligase 1 (NEW ENGLAND BIOLABS®), 10 µl 10× T4 RNA ligase buffer, 5 µl BC_0047 oligo at 50 µM, 50 µl 50% PEG 8000, and 10 µl 10 mM ATP) can be added to the 20 µl of beads in the PCR tube. 50 µl of the ligase mixed with the beads can be transferred into a new PCR tube to prevent too many beads from settling to the bottom of a single tube and the sample can be incubated at 25° C. for 16 hours.

Example 8—Generating ILLUMINA® Compatible Sequencing Products

Figure 16:
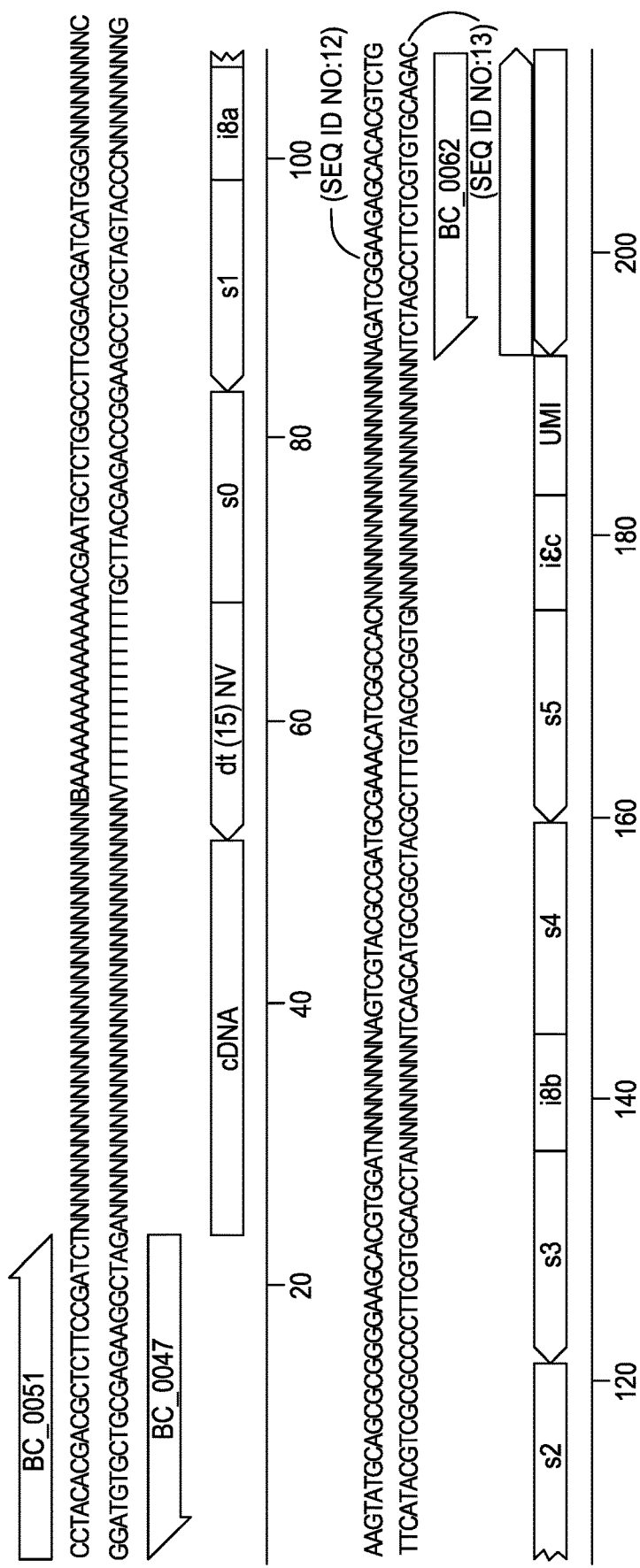
FIG. 16 depicts a PCR product formed using primers BC_0051 and BC_0062 and the 3' adapter oligo (BC_0047) after it has been ligated to barcoded cDNA.

Ligation reactions from both PCR tubes can be combined into a single 1.7 ml microcentrifuge tube (EPPENDORF®). 750 µl of $H_2O$-T can be added to each sample. Each of the tubes can be placed on a magnetic tube rack (EPPENDORF®) for 2 minutes, the liquid can be aspirated, and the samples can be resuspended in 40 µl water. The samples can be transferred to PCR tubes. 60 µl of PCR mix can be added to each tube (50 µl 2× PHUSION® DNA Polymerase Master Mix (THERMO FISHER™ Scientific), 5 µl BC_0051 (10 µM), and 5 µl BC_0062 (SEQ ID NO. 17) (10 µM)). 10 cycles of PCR can be run (98° C. for 3 minutes, repeat 10 times (98° C. for 10 seconds, 65° C. for 15 seconds, and 72° C. for 60 seconds), and 72° C. for 5 minutes). FIG. 16 depicts the PCR product. After the 3' adapter oligo (BC_0047) has been ligated to barcoded cDNA, the cDNA can be amplified using PCR. As shown in FIG. 16, the primers BC_0051 and BC_0062 (SEQ ID NO. 17) were used.

The PCR samples from the previous step can be procured and the magnetic beads can be displaced to the bottom of each tube with a magnet. 90 µl of PCR reaction can be transferred to a new 1.7 ml without transferring any of the magnetic beads. 10 µl of nuclease-free water can be added to each of the 1.7 ml tubes to a total volume of 100 µl. 60 µl of AMPURE™ beads can be added to the 100 µl of PCR reaction (0.6×SPRI) and bound for 5 minutes. The tubes can be placed against a magnet for 2 minutes and the samples can be washed with 200 µl of 70% ethanol (30 second wait) without resuspending the beads. The samples can be washed again with 200 µl of 70% ethanol (30 second wait) without resuspending the beads and then the samples can be air dried for 5-10 minutes until the ethanol has evaporated.

Each of the samples can be resuspended in 40 µl of nuclease-free water. The tubes can be placed against a magnetic rack for 2 minutes. While the microcentrifuge tubes (EPPENDORF®) are still disposed against the magnetic rack, 38 µl of solution can be transferred to a new 1.7 ml tube, without transferring beads. 62 µl of nuclease-free water can be added to the samples to a total volume of 100 µl. 60 µl of AMPURE™ beads can then be added to 100 µl of the PCR reaction (0.6×SPRI) and bound for 5 minutes. The tubes can be placed against a magnet for 2 minutes and then the samples can be washed with 200 µl of 70% ethanol (30 second wait) without resuspending the beads. The samples can be washed again with 200 µl 70% ethanol (30 second wait) without resuspending the beads and then the samples can be air dried for 5-10 minutes until the ethanol has evaporated.

Figure 17:
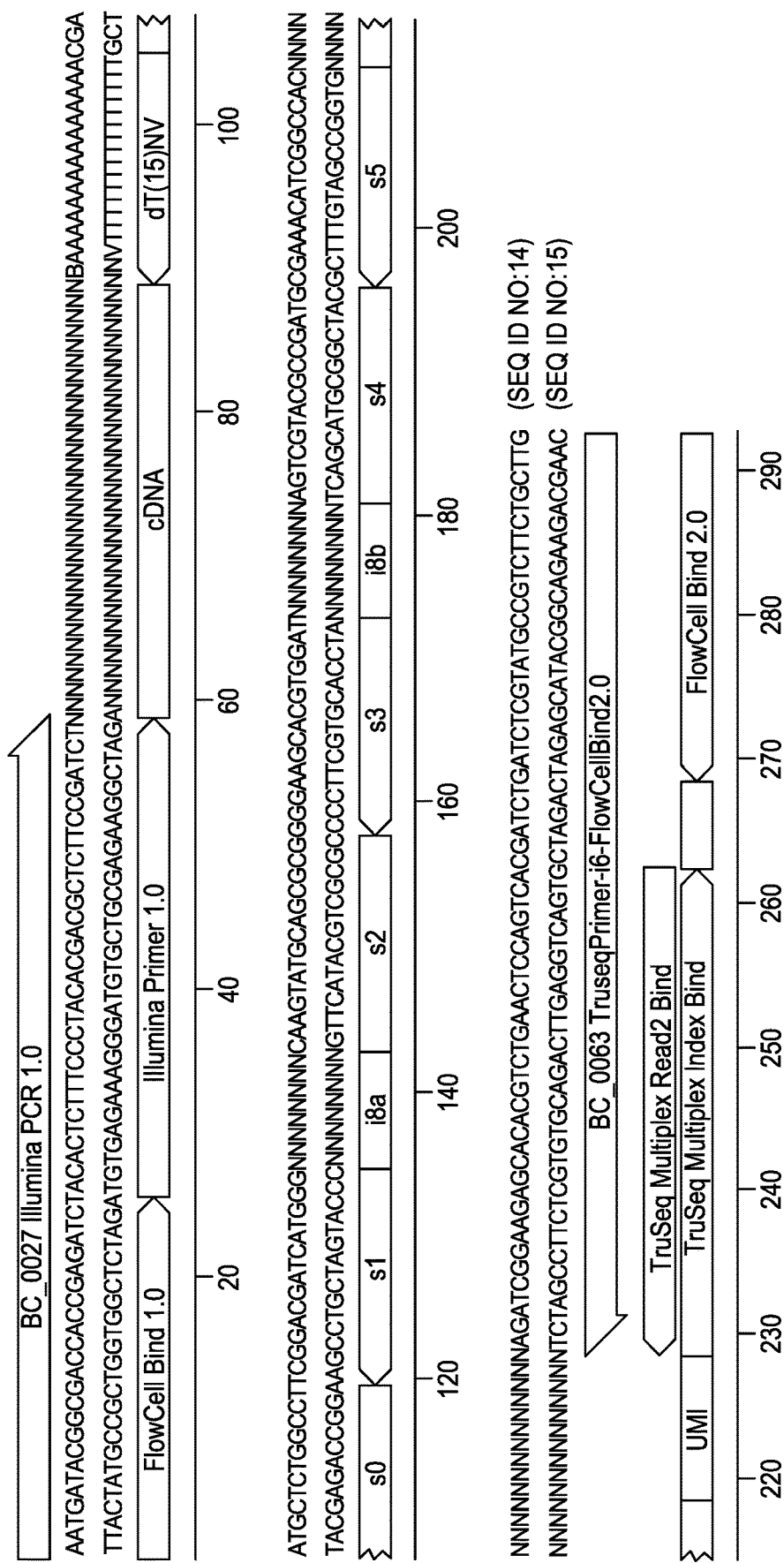
FIG. 17 depicts BC_0027, which includes the flow cell binding sequence and the binding site for the TRUSEQ™ read 1 primer and BC_0063, which includes the flow cell binding sequence and the TruSeq multiplex read 2 and index binding sequence.

The samples can be resuspended in 40 µl of nuclease-free water and each tube can be placed against a magnetic rack for 2 minutes. While the tube is still disposed against the magnetic rack, 38 µl of solution to a new 1.7 ml tube, without transferring any beads. 20 µl of the 38 µl elution can be added to an optical PCR tube. Furthermore, a PCR mix can be added to the tube (25 µl PHUSION® DNA Polymerase Master Mix (THERMO FISHER™ Scientific), 2.5 µl BC_0027 (10 µM), 2.5 µl BC_0063 (10 µM), and 2.5 µl 20× EVAGREEN® (BIOTIUM™)). Following the PCR depicted in FIG. 16, the full ILLUMINA® adapter sequences can be introduced through another round of PCR. As depicted in FIG. 17, BC_0027 includes the flow cell binding sequence and the binding site for the TRUSEQ™ read 1 primer. BC_0063 includes the flow cell binding sequence and the TruSeq multiplex read 2 and index binding sequence. There is also a region for the sample index, which is GATCTG in this example.

The above samples can be run on a qPCR machine with the following cycling conditions: 1) 98° C. for 3 minutes, 2) 98° C. for 10 seconds, 3) 65° C. for 15 seconds, 4) 72° C. for 60 seconds, and 5) repeat steps 2-4 (e.g., 10-40 times, depending on when fluorescence stops increasing exponentially). The tube can be transferred to a thermocycler set to 72° C. for 5 minutes. The qPCR reaction can be run on a 1.5% agarose gel for 40 minutes and a 450-550 bp band can be removed and gel extracted (QIAQUICK® Gel Extraction Kit). The products can be sequenced on an ILLUMINA® MISEQ™ using paired end sequencing. The sequencing primers can be the standard TRUSEQ™ multiplex primers. Read 1 can sequence the cDNA sequence, while read 2 can cover the unique molecular identifier as well as the 3 barcode sequences (8 nucleotides each). Index read 1 can be used to sequence sample barcodes, so multiple samples may be sequenced together.

Example 9—Data Analysis

Figure 18:
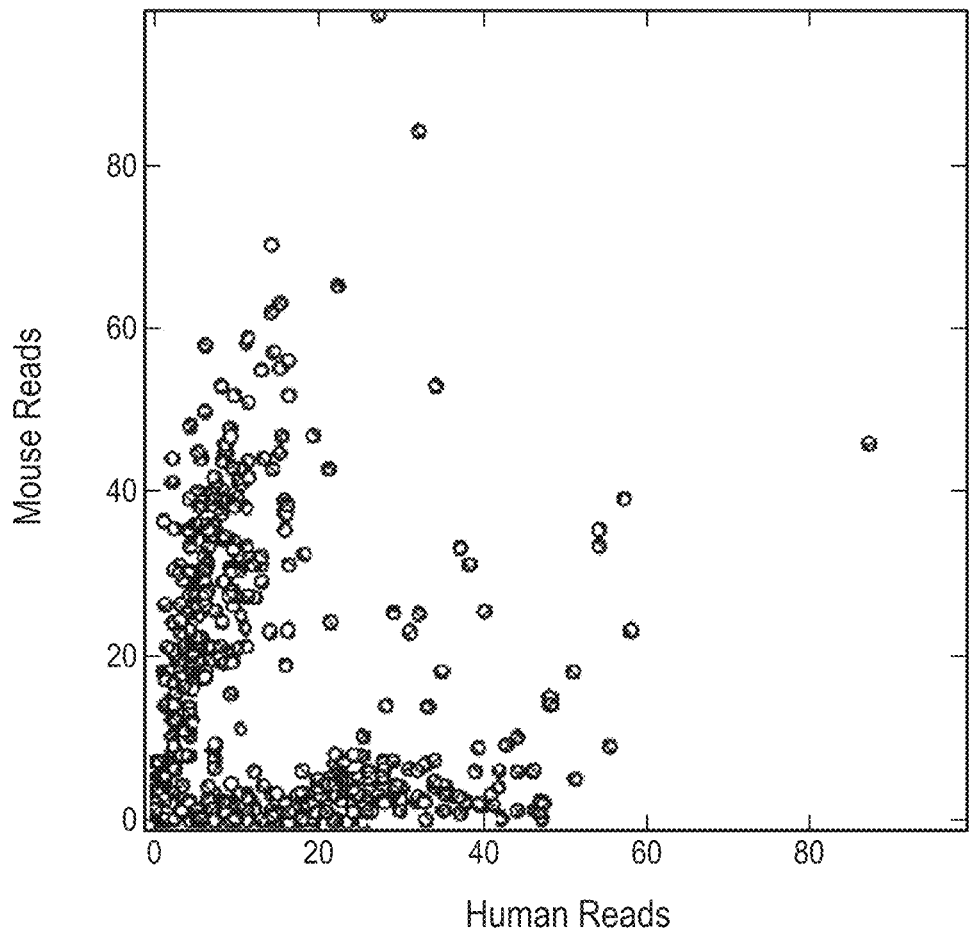
FIG. 18 is a scatter plot, wherein for each unique barcode combination the number of reads aligning to the human genome (x-axis) and the mouse genome (y-axis) are plotted.
Figure 20:
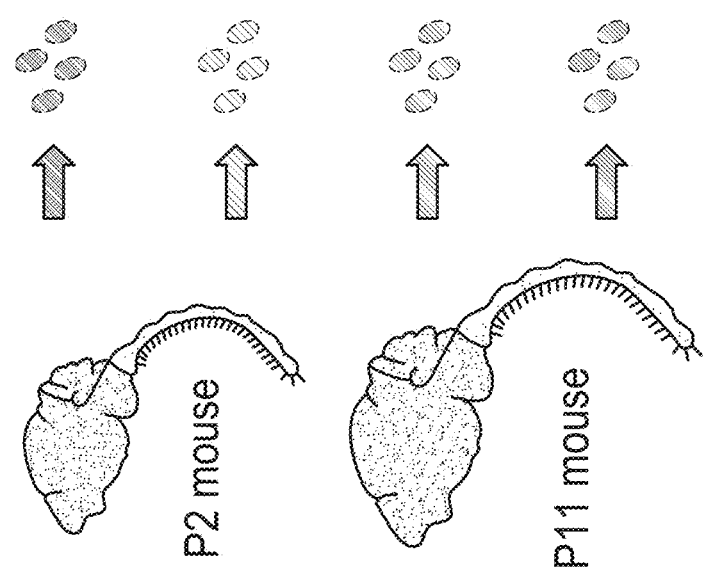
FIG. 20 illustrates an experiment wherein over 150,000 nuclei from P2 and P11 mouse brains and spinal cords were profiled in a single experiment employing over six million barcode combinations. By recording which of the four starting samples (P2 spine, P2 brain, P11 spine, or P11 spine) were added to each well, the first-round barcode sequences can be used to identify which cell/nuclei originated from which sample.
Figure 21A:
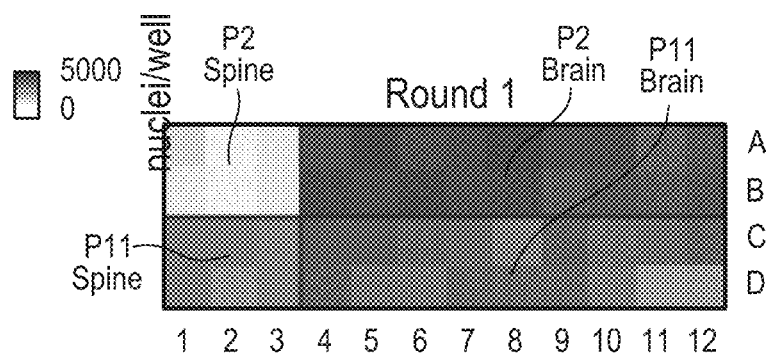
FIGS. 21A-21C show the number of nuclei in each well during three rounds of barcoding. Despite pipetting cells by hand, most wells contain approximately equal numbers of nuclei. Dissociation of the P2 spinal cord resulted in fewer cells than the other samples, explaining the lower number of nuclei in the corresponding first round wells.
Figure 21B:
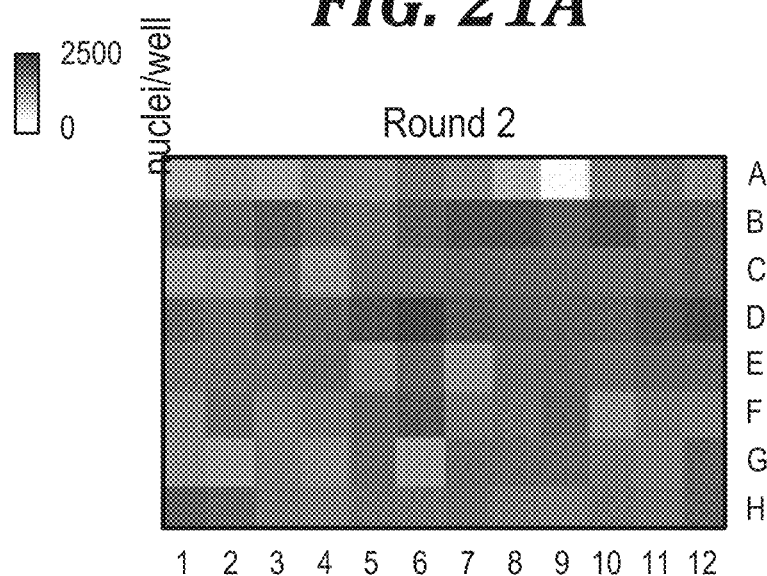
Figure 21C:
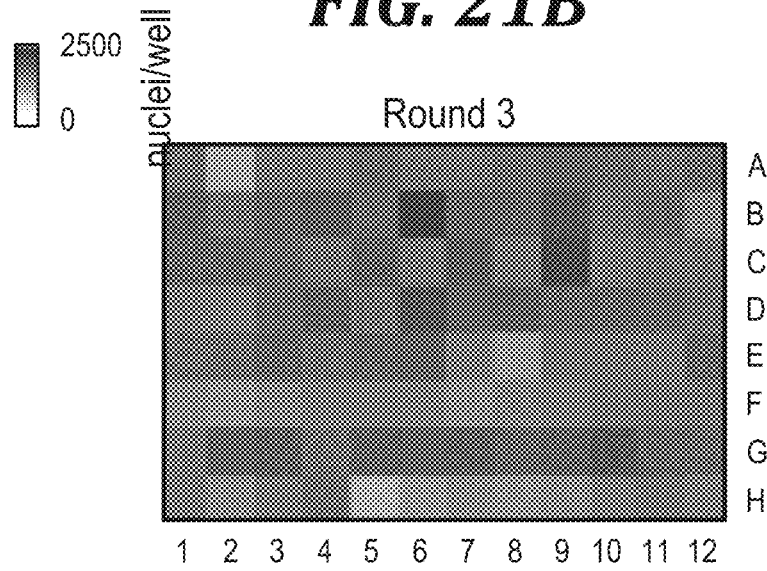

Sequencing reads were grouped by cell barcodes (three barcodes of eight nucleotides each, 96×96×96=884,736 total combinations). Each barcode combination should correspond to the cDNA from a single cell. Only reads with valid barcodes were retained. The sequencing reads with each barcode combination were aligned to both the human genome and the mouse genome. Reads aligning to both genomes were discarded. Multiple reads with the same unique molecular identifier were counted as a single read. Reads with unique molecular identifiers with two or less mismatches were assumed to be generated by sequencing errors and were counted as a single read. For each unique barcode combination the number of reads aligning to the human genome (x-axis) and the mouse genome (y-axis) were plotted (see FIG. 18). As each cell is either mouse or human, it should ideally include only one type of RNA. So an ideal plot would have every point along the x- or y-axis. The fact that most points in the plot of FIG. 18 are near an axis indicates that the method is viable.

Each point in the plot corresponds to cDNA with the same combination of barcodes and should represent the cDNA from a single cell. For each point, the number of reads that map uniquely to the mouse genome are plotted on the y-axis, while the number of reads that map uniquely to the human genome are plotted on the x-axis. If cDNAs with a specific combination of barcodes came from a single cell, all of the cDNA with the specific combination of barcodes should map completely to the human genome or completely to the mouse genome. As stated above, the fact that most barcode combinations map close to either the x-axis (human cells) or the y-axis (mouse cells) indicates that the method can indeed produce single-cell RNA sequencing data.

Example 10—Methods of Uniquely Labeling Molecules of a Plurality of Cells

For the following disclosed protocol the projected experimental time is two (2) days. As indicated below, RNase inhibitor may be added to the buffers. Accordingly, when any buffer includes the term "+RI", this indicates that ENZYMATICS® RNase inhibitor should be added to a final concentration of 0.1 U/µL. The centrifugation steps may be performed with a swinging bucket rotor. In some embodiments, using a fixed angle centrifuge may lead to more cell loss. Depending on the tissue type, centrifugation speeds may need to be changed to optimize cell retention (e.g., smaller cells=higher speeds).

For DNA barcoding plate generation the following may be needed: i) three 96-well plates from IDT®, reverse transcription barcode primers, ligation round 1, and ligation round 2 stock DNA oligo plates (100 µM); ii) two linker oligos, BC_0215 (SEQ ID NO. 30) and BC_0060 (SEQ ID NO. 16) (Note: these are assumed to be in stock concentration of 1 mM, thus, correct for volume if another stock concentration is to be used (e.g., 100 µM stocks)); and iii) Six 96-well PCR plates (e.g., three (3) stock plates that will last at least 10 experiments, and three (3) plates for first experiment). Note that this can generate 100 µL of DNA barcodes for each well. Each experiment generally requires only 4 µL/well of the reverse transcription primer solution which can last for 25 experiments. Each experiment generally requires only 10 µL/well of the barcode/linker solutions, so these plates can last for a total of 10 experiments.

Round 1 Reverse Transcription Barcoded Primers (final concentrations of 12.5 µM random hexamer and 12.5 µM 15 dT primers in each of 48 wells): 1) using a multichannel pipette, add 12.5 µL of rows A-D in the IDT® reverse transcription barcode primers to rows A-D of the BC stock 96-well PCR plate; 2) using a multichannel pipette, add 12.5 µL of rows E-H in the IDT® reverse transcription barcode primers to rows A-D of the BC stock 96-well PCR plate (mixing poly dT with random hexamer primer here); 3) add 75 μl of water to rows A-D of the BC stock 96-well PCR plate.

Round 2 Ligation Round (final concentrations of 12 μM barcodes, 11 μM linker-BC_0215 (SEQ ID NO. 28)): 1) using a multichannel pipette, add 12 μL of IDT® round 2 barcodes to R1 stock 96-well PCR plate; 2) add 138.6 μl of BC_0215 (SEQ ID NO. 28) (1 mM) to 10.9494 mL water in a basin (BC_0215_dil); and 3) using a multichannel pipette, add 88 μL BC_0215_dil to each well of R2 stock 96 well PCR plate.

Ligation Round 3 (final concentrations of 14 μM barcodes, 13 μM linker-BC_0060, SEQ ID NO. 16): 1) using a multichannel pipette, add 14 μL of round 3 barcodes to R3 stock 96-well PCR plate; 2) add 163.8 μl of BC_0060 (SEQ ID NO. 16) (1 mM) to 10.6722 mL water in a basin (BC_0060_dil); and 3) using a multichannel pipette, add 86 μL BC_0060 (SEQ ID NO. 16) to each well R3 stock 96 well PCR plate.

For each ligation plate (R2 and R3, not including reverse transcription barcodes), anneal the barcode and linker oligos with the following thermocycling protocol: 1) heat to 95° C. for two (2) minutes and 2) ramp down to 20° C. for at a rate of 0.1° C./s; and 3) 4° C.

Aliquot out 10 μL of each barcode/linker stock plate into three (3) new 96-well PCR plates. These are the plates that should be used for DNA barcoding in the split-pool ligation steps in the protocol.

I. Nuclei Extraction (Optional): 1) prepare the following items, a) keep Dounce homogenizer at 4° C. until use, b) 15 ml of 1×PBS+37.5 SUPERASE-IN™+19 μl ENZYMATICS® RNase inhibitor (kept on ice), and c) precool centrifuge to 4° C.

2) Make NIM1 buffer (Table 1):

TABLE 1

NIM1 Buffer

| Reagent | Stock Concentration | Final Concentration | Volume (μL) |
| --- | --- | --- | --- |
| Sucrose | 1.5M | 250 mM | 2,500 |
| KCl | 1M | 25 mM | 375 |
| MgCl$_2$ | 1M | 5 mM | 75 |
| Tris buffer, pH 8 | 1M | 10 mM | 150 |
| Water | NA | NA | 11,900 |
| Final Volume | | | 15,000 |

3) Make the homogenization buffer (Table 2):

TABLE 2

Homogenization Buffer

| Reagent | Stock Concentration | Final Concentration | Volume (μL) |
| --- | --- | --- | --- |
| NIM1 Buffer | 1.5M | | 4,845 |
| 1 mM DTT | 1 mM | 1 μM | 5 |
| ENZYMATICS ® RNase-In (40 U/μl) | 40 U/μL | 0.4 U/μl | 50 |
| SUPERASE-IN ™ (20 U/μL) | 20 U/μL | 0.2 U/μl | 50 |
| 10% TRITON ™ X-100 | 10% | NA | 50 |
| Final Volume | | | 5,000 |

4) Dounce homogenizer: a) add tissue/cells sample to Dounce homogenizer; if cells, resuspend in 700 μl of homogenization buffer; b) add homogenization buffer to ~700 μl; c) perform 5 strokes of loose pestle; d) perform 10-15 of tight pestle; e) add homogenization buffer up to 1 ml; and f) check cell lysis with 5 μl trypan blue and 5 μl cells on hemocytometer to see if nuclei have been released.

5) Filter homogenates with a 40 μm strainer into 5 ml EPPENDORF™ tubes (or 15 mL FALCON™ tubes). Tilting the filter 45° while straining over the tube can ensure that the lysate passes through as intended. Note: this straining process is different from the straining processes below.

6) Spin for 4 minutes at 600×g (4° C.) and remove supernatant (can leave about 20 μL to avoid aspirating pellet). 7) Resuspend in 1 ml of 1×PBS+RI. 8) Add 10 μl of BSA. 9) Centrifuge at 600×g for 4 minutes. 10) Resuspend in 200 μl 1×PBS+RI.

11) Take 50 μl of the resuspended cells from step 4 and add 150 μl of 1×PBS+RI. Count sample on hemocytometer and/or flow-cytometer. The volume of resuspended cells from the step 4 can be changed based on the considerations of the user. 12) Pass cells through a 40 μm strainer into a fresh 15 mL FALCON™ tube and place on ice (see note below on step 4 of II. Fixation and Permeabilization). 13) Resuspend the desired number of nuclei (typically 2M) in 1 mL 1×PBS+RI and proceed with step 5 in the following Fixation and Permeabilization protocol.

II. Fixation and Permeabilization: 1) prepare the following buffers (calculated for two experiments): a) a 1.33% formalin (360 μL of 37% formaldehyde solution (SIGMA®)+9.66 ml PBS) solution and store at 4° C.; b) 6 mL of 1×PBS+RI (15 μL of SUPERASE-IN™ and 7.5 μL of ENZYMATICS® RNase inhibitor); c) 2 mL of 0.5×PBS+RI (5 μL of SUPERASE-IN™ and 2.5 μl of ENZYMATICS®) RNase inhibitor); d) 500 μL of 5% TRITON™ X-100+RI (2 μL of SUPERASE-IN™); e) 500 μL of 100 mM Tris pH 8.0+2 μL SUPERASE-IN™; and f) set the centrifuge to 4° C.

2) Pellet cells by centrifuging at 500×g for 3 minutes at 4° C. (some cells may require faster centrifugation). 3) Resuspend cells in 1 mL of cold PBS+RI. Keep cells on ice between these steps. 4) Pass cells through a 40 μm strainer into a fresh 15 mL FALCON™ tube and place on ice. Note: the cell resuspension is not likely to passively go through the strainer, which can cause cell loss. Instead, with a 1 ml pipette filled with the resuspension, press the end of the tip directly onto the strainer and actively push the liquid through. The motion should take about one (1) second. 5) Add 3 mL of cold 1.33% formaldehyde (final concentration of 1% formaldehyde). Fix cells on ice for 10 minutes. 6) Add 160 μL of 5% TRITON™ X-100+RI to fixed cells and mix by gently pipetting up and down 5 times with a 1 mL pipette. Permeabilize cells for 3 minutes on ice. 7) Centrifuge cells at 500×g for 3 minutes at 4° C. 8) Aspirate carefully and resuspend cells in 500 μL of cold PBS+RI. 9) Add 500 μL of cold 100 mM Tris-HCl, pH 8.0. 10) Add 20 μL of 5% TRITON™ X-100. 11) Centrifuge cells at 500×g for 3 minutes at 4° C. 12) Aspirate and resuspend cells in 300 μl of cold 0.5×PBS+RI.

13) Run cells through a 40 μM strainer into a new 1.7 mL tube (see note above on step 4 of II. Fixation and Permeabilization). 14) Count cells using a hemocytometer or a flow-cytometer and dilute the cell suspension to 1,000,000 cells/mL. While counting cells, keep cell suspension on ice. Note: this step will dictate how many cells enter the split-pool rounds. It will be possible to sequence only a subset of the cells that enter the split-pool rounds (can be done during sub-library generation at lysis step). The total number of barcode combinations that will be used should be calculated to determine the maximum number of cells that can be sequenced with minimal barcode collisions. Without being bound by any one particular theory, the number of cells that will be processed should not exceed more than 5% of total barcode combinations. Generally, a dilution between 500 k to 1M cells/mL can be used here (equates to 4-8 k cells going into each well for reverse transcription barcoding rounds).

III. Reverse Transcription: 1) aliquot out 4 µL of the RT barcodes stock plate into the top four (4) rows (48 wells) of a new 96-well plate. Cover this plate with an adhesive plate seal until ready for use.

2) Create the following reverse transcription (RT) mix on ice (Table 3):

TABLE 3

RT Mix

| Reagent | Stock Concentration | Desired Concentration | Per Reaction | Volume in Mix (48 wells + 10%) |
| --- | --- | --- | --- | --- |
| 5 × RT Buffer | 5× | 1× | 4 | 211.2 |
| ENZYMATICS® RNase Inhibitor | 40 u/µL | 0.25 u/µL | 0.125 | 6.6 |
| SUPERASE-IN™ RNase Inhibitor | 20 U/µL | 0.25 U/µL | 0.25 | 13.2 |
| dNTPs | 10 mM (per base) | 500 µM | 1 | 52.8 |
| Maxima H Minus Reverse Transcriptase | 200 u/µL | 20 u/µl | 2 | 105.6 |
| H₂O | NA | NA | 0.625 | 33 |
| Total Volume | | | 8 | 422.4 |

3) Add 8 µL of the RT mix to each of the top 48 wells. Each well should now contain a volume of 12 µL. 4) Add 8 µL of cells in 0.5×PBS+RI to each of the top 48 wells. Each well should now contain a volume of 20 µL. 5) Add the plate into a thermocycler with the following protocol: a) 50° C. for 10 minutes; b) cycle three (3) times, i) 8° C. for 12 seconds, ii) 15° C. for 45 seconds, iii) 20° C. for 45 seconds, and iv) 30° C. for 30 seconds, v) 42° C. for 2 minutes, vi) 50° C. for 3 minutes; c) 50° C. for 5 minutes; and d) 4° C. forever.

6) Place the RT plate on ice. 7) Prepare 2 mL of 1×NEB buffer 3.1 with 20 µL of ENZYMATICS® RNase Inhibitor. 8) Transfer each RT reaction to a 15 ml FALCON™ tube (also on ice). 9) Add 9.6 µL of 10% TRITON™ X-100 to get a final concentration of 0.1%. 10) Centrifuge pooled RT reaction for 3 minutes at 500×g. 11) Aspirate supernatant and resuspend into 2 mL of 1×NEB buffer 3.1+20 µL ENZYMATICS® RNase Inhibitor.

IV. Ligation Barcoding: 1) make the following ligation master mix on ice (Table 4):

TABLE 4

Ligation Master Mix

| Reagent | Stock Concentration | Final Concentration | Volume (µL) |
| --- | --- | --- | --- |
| Water | NA | NA | 1337.5 |
| T4 Ligase Buffer 10× | 10× | 1× | 500 |
| ENZYMATICS® RNase Inhibitor | 40 U/µL | 0.32 U/µL | 40 |

TABLE 4-continued

Ligation Master Mix

| Reagent | Stock Concentration | Final Concentration | Volume (µL) |
| --- | --- | --- | --- |
| SUPERASE-IN™ | 20 U/µL | 0.05 U/µL | 12.5 |
| BSA | 20 mg/mL | 0.2 mg/mL | 50 |
| T4 DNA Ligase | 400 U/µL | 8 U/µL | 100 |
| Total Volume | | | 2040 |

Note: final concentration takes added volume of DNA barcodes into account. Concentration of this mix is not the final concentration at time of barcoding.

2) Add the 2 mL of cells in NEB buffer 3.1 into the ligation mix. The mix should now have a volume of 4.04 mL. 3) Add the mix into a basin. 4) Using a multichannel pipet, add 40 µL of ligation mix (with cells) into each well of the round 1 DNA barcode plate. 5) Cover the round 1 DNA barcode plate with an adhesive plate seal and incubate for 30 minutes at 37° C. with gentle rotation (50 rpm). 6) Make the round 1 blocking solution and add it to a new basin (Table 5).

TABLE 5

Round 1 Blocking Solution

| Reagent | Stock Concentration | Final Concentration | Volume (µL) |
| --- | --- | --- | --- |
| BC_0216 | 100 µM | 26.4 µM | 316.8 |
| 10 × Ligase Buffer | 10× | 2.5× | 300 |
| Water | NA | NA | 583.2 |
| Final Volume | | | 1200 µL |

7) Remove the round 1 DNA barcoding plate from the incubator and remove the cover. 8) Using a multichannel pipet, add 10 µL of the round 1 blocking solution to each of the 96 wells in the round 1 DNA barcoding plate. 9) Cover the round 1 DNA barcode plate with an adhesive plate seal and incubate for 30 minutes at 37° C. with gentle rotation (50 rpm). 10) Remove round 1 DNA barcoding plate from the incubator, remove cover, and pool all cells into a new basin. 11) Pass all the cells from this basin through a 40 µm strainer into another basin (see note above on step 4 of Fixation and Permeabilization). 12) Add 100 µL of T4 DNA ligase to the basin and mix by pipetting about 20 times. 13)

Using a multichannel pipette, add 50 µL of cell/ligase solution into each well of the round 2 DNA barcode plate. 14) Cover the round 2 DNA barcode plate with an adhesive plate seal and incubate for 30 minutes at 37° C. with gentle rotation (50 rpm).

15) Make the round 2 blocking solution and add it to a new basin (Table 6).

TABLE 6

Round 2 Blocking Solution

| Reagent | Stock Concentration | Final Concentration | Volume (µL) |
|---|---|---|---|
| BC_0066 | 100 µM | 11.5 µM | 369 |
| EDTA | 0.5M | 125 mM | 800 |
| Water | NA | NA | 2031 |
| Final Volume | | | 3200 µL |

16) Remove the round 2 DNA barcoding plate from the incubator and remove the cover. 17) Using a multichannel pipet, add 20 µL of the round 2 blocking and termination solution to each of the 96 wells in the round 2 DNA barcoding plate. 18) Pool all cells into a new basin (no incubation for the final blocking step). 19) Pass all the cells from this basin through a 40 µm strainer into a 15 mL FALCON™ tube (see note above on step 4 of Fixation and Permeabilization). 19) Count cells on a flow cytometer. Make sure cells are well mixed before aliquoting sample for counting.

V. Lysis: 1) make the 2× lysis buffer (Table 7).

TABLE 7

2 × Lysis Buffer

| Reagent | Stock Concentration | Final Concentration (2×) | Volume (mL) |
|---|---|---|---|
| Tris, pH 8.0 | 1M | 20 mM | 0.5 |
| NaCl | 5M | 400 mM | 2 |
| EDTA, pH 8.0 | 0.5M | 100 mM | 5 |
| SDS | 10% | 4.4% | 11 |
| Water | NA | NA | 6.5 |
| Final Volume | | | 25 |

2) If white precipitate appears, warm at 37° C. until precipitate is back in solution (about 10-15 minutes).

3) Make the following wash buffer (Table 8).

TABLE 8

Wash Buffer

| Reagent | Volume (µL) |
|---|---|
| 1 × PBS | 4000 |
| 10% TRITON ™ X-100 | 40 |
| SUPERASE-IN ™ RNase Inhibitor | 10 |
| Final Volume | 4050 |

4) Add 70 µl of 10% TRITON™ X-100 to the cells (~0.1% final concentration). 5) Centrifuge for 5 minutes at 1000×g in 15 ml tube. Note: the pellet for the steps below can be very small and it may not be visible. 6) Aspirate supernatant, leave about 30 µl to avoid removing pellet, a) if possible, remove as much supernatant as possible with a 20 µL pipet. 7) Resuspend with 4 mL of wash buffer. 8) Centrifuge for 5 minutes at 1000×g. 9) Aspirate supernatant and resuspend in 50 µl 1×PBS+RI.

10) Dilute 5 µl into 195 µL of 1×PBS and count via flow cytometry. Or take 5 µl into 5 µl of 1×PBS and count on hemocytometer (it can be hard to distinguish debris from cells). 11) Determine how many sub-libraries to generate (# of sub-libraries=# of tubes needed), and how many cells to have for each of these sub-libraries. 12) Aliquot the desired number of cells for each sub-library into new 1.7 mL tubes. Add 1×PBS to each tube to a final volume of 50 µL.

13) Add 50 µL of 2× Lysis buffer to each tube. 14) Add 10 µL of Proteinase K (20 mg/mL) to each lysate. 15) Incubate at 55° C. for 2 hours with shaking at 200 rpm. 16) Stopping point (optional): freeze lysate(s) at −80° C.

VI. Prepare Buffers. First make the following stock solutions (Tables 9-11).

TABLE 9

Phenylmethanesulfonyl Fluoride (PMSF)

100 mM PMSF

TABLE 10

2 × B&W
2 × B&W

| Reagents | Volume |
|---|---|
| 1M Tris-HCl pH 8.0 | 500 µL |
| 5M NaCl | 20 ml |
| EDTA, 0.5M | 100 µl |
| Nuclease Free Water | 29.4 ml |
| Total | 50 mL |

TABLE 11

1 × B&W-T
1 × B&W-T

| Reagents | Volume |
|---|---|
| 1M Tris-HCl pH 8.0 | 100 µL |
| 5M NaCl | 4 ml |
| EDTA, 0.5M | 20 µl |
| Tween 20 10% | 100 µl |
| Nuclease Free Water | 15.78 ml |
| Total | 20 mL |

Then make the following smaller aliquots (with added RNase inhibitor; Tables 12-14):

TABLE 12

1X B&W-T +RI

| | Volume per Number of Samples (μL) | | | | | | | |
|---|---|---|---|---|---|---|---|---|
| Reagent | 1 | 2 | 3 | 4 | 5 | 6 | 7 | 8 |
| 1X B&W-T | 3600.0 | 4200.0 | 4800.0 | 5400.0 | 6000.0 | 6600.0 | 7200.0 | 7800.0 |
| SUPERASE-IN™ | 1.5 | 3.0 | 4.5 | 6.0 | 7.5 | 9.0 | 10.5 | 12.0 |
| Final Volume | 3601.5 | 4203.0 | 4804.5 | 5406.0 | 6007.5 | 6609.0 | 7210.5 | 7812.0 |

TABLE 13

2X B&W +RI

| | Volume per Number of Samples (μL) | | | | | | | |
|---|---|---|---|---|---|---|---|---|
| Reagent | 1 | 2 | 3 | 4 | 5 | 6 | 7 | 8 |
| 2X B&W | 110.0 | 220.0 | 330.0 | 440.0 | 550.0 | 660.0 | 770.0 | 880.0 |
| SUPERASE-IN™ | 2.0 | 4.0 | 6.0 | 8.0 | 10.0 | 12.0 | 14.0 | 16.0 |
| Final Volume | 112.0 | 224.0 | 336.0 | 448.0 | 560.0 | 672.0 | 784.0 | 896.0 |

TABLE 14

Tris-T +RI

| | Volume per Number of Samples (μL) | | | | | | | |
|---|---|---|---|---|---|---|---|---|
| Reagent | 1 | 2 | 3 | 4 | 5 | 6 | 7 | 8 |
| Tris-HCl pH 8.0 | 600.0 | 1200.0 | 1800.0 | 2400.0 | 3000.0 | 3600.0 | 4200.0 | 4800.0 |
| Tween-20 (10%) | 6.0 | 12.0 | 18.0 | 24.0 | 30.0 | 36.0 | 42.0 | 48.0 |
| SUPERASE-IN™ | 1.5 | 3.0 | 4.5 | 6.0 | 7.5 | 9.0 | 10.5 | 12.0 |
| Final Volume | 607.5 | 1215.0 | 1822.5 | 2430.0 | 3037.5 | 3645.0 | 4252.5 | 4860.0 |

VII. Purification of cDNA. Note: agitation steps have been performed on a vortexer with a foam 1.7 mL tube holder on a low setting (2/10).

Wash MYONE™ C1 DYNABEADS®: 1) for each lysate to be processed, add 44 μL of MYONE™ C1 DYNABEADS® to a 1.5 ml tube (e.g., 1 lysate=44 μL, 2 lysates=88 μL, 3 lysates=132 μL, etc.). 2) Add 800 μL of 1× B&W-T buffer. 3) Place sample against a magnetic rack and wait until liquid becomes clear (1-2 minutes). 4) Remove supernatant and resuspend beads in 800 μL of 1× B&W-T buffer. 5) Repeat steps 3-4 two more times for a total of 3 washes. 6) Place sample against a magnetic rack and wait until liquid becomes clear. 7) Resuspend beads in 100 μL (per sample) 2× B&W buffer+RI.

Sample Binding to Streptavidin: 1) add 5 μL of 100 μM PMSF to each sample and leave at room temperature for 10 minutes. 2) Add 100 μl of resuspended C1 beads to each tube. 3) To bind cDNA to C1 beads, agitate at room temperature for 60 minutes. 4) Place sample against a magnetic rack and wait until liquid becomes clear (1-2 minutes). 5) Remove supernatant and resuspend beads in 250 μL of 1× B&W. 6) Agitate beads for 5 minutes at room temperature. 7) Repeat steps 5 and 6. 8) Remove supernatant and resuspend beads in 250 μL of 10 mM Tris+T. 9) Agitate beads for 5 minutes at room temperature. 10) Leave beads in final wash solution on ice.

Template Switch. Prepare the following mix depending on the number of samples (Table 15).

TABLE 15

Mix

| Reagent | Volume per Number of Samples (μL) | | | | | | | |
|---|---|---|---|---|---|---|---|---|
| | 1 | 2 | 3 | 4 | 5 | 6 | 7 | 8 |
| Water | 88.0 | 176.0 | 264.0 | 352.0 | 440.0 | 528.0 | 616.0 | 704.0 |
| Maxima RT Buffer | 44.0 | 88.0 | 132.0 | 176.0 | 220.0 | 264.0 | 308.0 | 352.0 |
| FICOLL ® PM-400 (20%) | 44.0 | 88.0 | 132.0 | 176.0 | 220.0 | 264.0 | 308.0 | 352.0 |
| 10 mM dNTPs (each, total is 40 mM) | 22.0 | 44.0 | 66.0 | 88.0 | 110.0 | 132.0 | 154.0 | 176.0 |
| RNase Inhibitor | 5.5 | 11.0 | 16.5 | 22.0 | 27.5 | 33.0 | 38.5 | 44.0 |
| TSO (BC_0127) | 5.5 | 11.0 | 16.5 | 22.0 | 27.5 | 33.0 | 38.5 | 44.0 |
| Maxima RT RNaseH Minus Enzyme | 11.0 | 22.0 | 33.0 | 44.0 | 55.0 | 66.0 | 77.0 | 88.0 |
| Total | 220.0 | 440.0 | 660.0 | 880.0 | 1100.0 | 1320.0 | 1540.0 | 1760.0 |

1) Place sample against a magnetic rack and wait until liquid becomes clear. 2) With sample still on magnetic rack, remove supernatant and wash with 250 μL of water (do not resuspend beads this time). 3) Resuspend sample in 200 μl of Template Switch Mix. 4) Incubate at room temp for 30 minutes with agitation or rolling. 5) Incubate at 42° C. for 90 minutes with agitation or rolling (the incubator has been shaken at 100 rpm).

6) Potential Stopping Point. If stopping, perform the following (otherwise skip to next section): a) place sample against a magnetic rack and wait until liquid becomes clear and b) resuspend in 250 μL Tris-T.

VIII. cDNA Amplification. Prepare the following PCR mix depending on the number of samples (Table 16).

TABLE 16

PCR Mix

| Reagent | Volume per Number of Samples (μL) | | | | | | | |
|---|---|---|---|---|---|---|---|---|
| | 1 | 2 | 3 | 4 | 5 | 6 | 7 | 8 |
| KAPA ™ HIFI 2X Master Mix | 121.00 | 242.00 | 363.00 | 484.00 | 605.00 | 726.00 | 847.00 | 968.00 |
| BC_0108 (10 μM) | 9.68 | 19.36 | 29.04 | 38.72 | 48.40 | 58.08 | 67.76 | 77.44 |
| BC_0062 (10 μM) | 9.68 | 19.36 | 29.04 | 38.72 | 48.40 | 58.08 | 67.76 | 77.44 |
| Water | 101.64 | 203.28 | 304.92 | 406.56 | 508.20 | 609.84 | 711.48 | 813.12 |
| Total | 242.0 | 484.0 | 726.0 | 968.0 | 1210.0 | 1452.0 | 1694.0 | 1936.0 |

1) Place sample against a magnetic rack and wait until liquid becomes clear. 2) With sample against magnet wash with 250 μL nuclease-free water (do not resuspend). 3) Resuspend sample with 220 μL PCR mix and split equally into four (4) different PCR tubes.

4) Run the following thermocycling program: a) 95° C., 3 minutes; b) 98° C., 20 seconds; c) 65° C., 45 seconds; d) 72° C., 3 minutes; e) repeat (b-d) four times (5 total cycles); and f) 4° C., hold.

5) Combine all four (4) reactions into a single 1.7 mL tube. Make sure to resuspend any beads that may be stuck to the bottom or sides of the PCR tubes before combining reactions. 6) Place sample against a magnetic rack and wait until liquid becomes clear. 7) Transfer 200 μL of supernatant to four (4) optical grade qPCR tubes (50 μL in each tube).

8) Add 2.5 μL of 20× EVAGREEN® to each qPCR tube. 9) Run the following qPCR program (make sure to remove samples, once signal starts to leave exponential phase to prevent over-amplification): a) 95° C., 3 minutes; b) 98° C., 20 seconds; c) 67° C., 20 seconds; d) 72° C., 3 minutes; e) repeat (b-d) until signal plateaus out of exponential amplification; f) 72° C., 5 minutes; and g) 4° C., hold.

10) Optional: run an agarose gel or bioanalyze resulting qPCR. There will likely be a combination of cDNA and dimer present.

SPRI Size Selection (0.8×). 1) Combine qPCR reactions into a single tube. 2) Take out 180 μL of the pooled qPCR reaction and place in new 1.7 mL tube. 3) Add 144 μL of KAPA™ Pure Beads to tube and vortex briefly to mix. Wait five (5) minutes to bind DNA. 4) Place tube against magnetic rack and wait until liquid becomes clear. 5) Remove the supernatant. 6) With tubes still on magnetic rack, wash with 750 μL 85% ethanol. Do not resuspend beads. 7) Repeat step 6.

8) Remove ethanol and air dry bead (~5 minutes). Do not let beads overdry and crack. 9) Resuspend beads from each tube in 20 μL of water. Once beads are fully resuspended in the water, incubate the tube at 37° C. for 10 minutes. 10) Bind tubes against magnetic rack and wait until liquid becomes clear. 11) Transfer 18.5 μL of elutant into a new optical grade PCR tube. 12) Run a bioanalyzer trace on 10 μL of the elutant.

13) If no dimer is present after size selection, jump directly to "Tagmentation and ILLUMINA® Amplicon Generation" section below. If dimer is still present, proceed to step 14 to perform a second amplification and size selection step. This may be necessary for cells with low RNA content, but should not be necessary for cells with high RNA content (e.g., HeLa-S3, NIH/3T3, etc.).

Second qPCR (Optional). 14) Make the following qPCR mix depending on the number of samples (Table 17).

TABLE 17 qPCR Mix

| Reagent | Volume per Number of Samples (µL) | | | | | | | |
|---|---|---|---|---|---|---|---|---|
| | 1 | 2 | 3 | 4 | 5 | 6 | 7 | 8 |
| KAPA ™ HIFI 2X Master Mix | 27.50 | 55.00 | 82.50 | 110.00 | 137.50 | 165.00 | 192.50 | 220.00 |
| BC_0062 (10 µM) | 2.20 | 4.40 | 6.60 | 8.80 | 11.00 | 13.20 | 15.40 | 17.60 |
| BC_0108 (10 µM) | 2.20 | 4.40 | 6.60 | 8.80 | 11.00 | 13.20 | 15.40 | 17.60 |
| EVAGREEN ® 20X | 2.75 | 5.50 | 8.25 | 11.00 | 13.75 | 16.50 | 19.25 | 22.00 |
| Sample | 20.35 | 40.70 | 61.05 | 81.40 | 101.75 | 122.10 | 142.45 | 162.80 |
| Total | 55.00 | 110.00 | 165.00 | 220.00 | 275.00 | 330.00 | 385.00 | 440.00 |

15) Add 31.5 µL of the qPCR master mix to each optical PCR tube with the previous PCR sample. Gently mix by flicking and spin tubes briefly in a table centrifuge to remove air bubbles. 16) Run the following qPCR program (make sure to remove samples, once signal starts to leave exponential phase to prevent over-amplification): a) 95° C., 3 minutes; b) 98° C., 20 seconds; c) 67° C., 20 seconds; d) 72° C., 3 minutes; e) repeat (b-d) until signal plateaus out of exponential amplification; f) 72° C., 5 minutes; and g) 4° C., hold.

17) Run an agarose gel or bioanalyze resulting qPCR. While there may still be dimer, amplified cDNA should be clearly visible between 500 bp to 2500 bp (see FIG. 19, left side for expected size distribution).

Second SPRI Size Selection (0.8×). 18) Combine qPCR reactions into a single tube. 19) Take out 40 µL of the qPCR reaction and place in new 1.7 mL tube. 20) Add 32 µL of KAPA™ Pure Beads to each tube and vortex briefly to mix. Wait 5 minutes to bind DNA.

21) Place tubes against magnetic rack and wait until liquid becomes clear. 22) Remove the supernatant. 23) With tubes still on magnetic rack, wash with 750 µL 85% ethanol. 24) Repeat step 5. 25) Remove ethanol and air dry bead (~5 minutes). Do not let beads overdry and crack. 26) Resuspend beads from each tube in 20 µL of water and wait 5 minutes. 27) Bind tubes against magnetic rack and wait until liquid becomes clear. 28) Transfer 18.5 µL of elutant into a 1.7 mL tube. 29) Run an agarose gel or bioanalyze resulting qPCR. There should be almost no dimer at this point. If dimer remains, perform another round of qPCR followed by another 0.8×SPRI size selection.

IX. Tagmentation and ILLUMINA® Amplicon Generation. 1) Quibit amplified cDNA and dilute to 0.12 ng/µL. 2) Preheat a thermocycler to 55° C. 3) For each sample, combine 600 pg of purified cDNA with H₂O in a total volume of 5 µl. 4) To each tube, add 10 µl of Nextera TD buffer and 5 µl of Amplicon Tagment enzyme (the total volume of the reaction is now 20 µl). Mix by pipetting about 5 times and spin down. 5) Incubate at 55° C. for 5 minutes. 6) Add 5 µl of Neutralization Buffer. Mix by pipetting about 5 times and spin down (bubbles are normal). 7) Incubate at room temperature for 5 minutes.

8) Add to each PCR tube in the following order: i) 15 µl of Nextera PCR mix; ii). 8 µl H₂O; iii) 1 µl of 10 µM (N7 indexed primer, one of BC_0076-BC_0083 (SEQ ID NOS. 19-26)); and iv) 1 µl of 10 µM Nextera (BC_0118, SEQ ID NO. 28) N501 oligo. 9) Run the following thermocycling program: i) 95° C., 30 seconds; ii) 12 cycles of: a) 95° C., 10 seconds; b) 55° C., 30 seconds; and c) 72° C., 30 seconds; and iii) then, 72° C., 5 minutes and 4° C. forever.

10) Transfer 40 µl out of the 50 µL reaction to a 1.7 mL tube. 11) Add 28 µL of KAPA™ Pure Beads to do a 0.7× cleanup. Elute in 20 µl. 12) Bioanalyze resulting sample and quibit before sequencing (see FIG. 19, right side, for expected size distribution).

X. ILLUMINA® Sequencing. 1) Use a paired-end sequencing run with a 150 bp kit. 2) Set read1 to 66 nt (transcript sequence). 3) Set read2 to 94 nt (cell-specific barcodes and UMI). 4) Include a 6 nt read 1 index to ready sub-library indices.

Example 11—Fixing Cells on Ice and Keeping Cells on Ice for Permeabilization

Unique molecular indices (UMIs) are random molecular barcodes that are added to each transcript/cDNA prior to amplification. They allow the computational removal of PCR duplicates, since these duplicates have the same UMI sequence. Thus, each original transcript will only be counted once, even if multiple PCR duplicates are sequenced.

The measure of UMIs per cell indicates how many unique RNA molecules can be detected per cell, which is directly related to how efficiently the molecules can be barcoded and processed to enable detection by next generation sequencing. This measure is generally the gold standard in the field and most researchers in the single cell RNA-sequencing space determine how well their experiment worked based on how many UMIs per cell are detected with a given amount of raw sequencing reads (e.g., 10,000 UMIs per cell with 50,000 sequencing reads per cell).

For each of Examples 11-16, all conditions within the same table (i.e., Table 18, Table 19, Table 20, Table 21, and Table 22) were sequenced to the same saturation level, allowing for an accurate comparison across conditions. Each condition had the same number of raw sequencing reads compared to another condition, indicating that differences in UMIs detected per cell detected were due to change in conditions rather than sequencing depth.

In other protocols (see, e.g., Rosenberg, A B, et al. BioRxiv (2017): 105163) formaldehyde fixation is performed at room temperature. Herein, experiments were performed showing a substantial improvement when cells were kept on ice (e.g., at 4° C.) during fixation and permeabilization (see Table 18).

TABLE 18

Room Temperature vs. 4° C.

| Approach | Unique RNA Molecules Detected Per Cell (UMIs per cell) |
|---|---|
| Cells kept at room temperature during fixation and permeabilization | 1002.72 |
| Cells kept at 4° C. during fixation and permeabilization | 1524.59 |

Example 12—Adding a Protease Inhibitor (PMSF) and Binding Directly to Streptavidin Beads In other protocols (see, e.g., Rosenberg, A B, et al. BioRxiv (2017): 105163) nucleic acids are first isolated from the lysis solution with an SPRI bead cleanup before binding desired nucleic acids (containing 5' biotin) to streptavidin beads. Herein, it was found that adding PMSF to lysates and then directly adding streptavidin beads (thereby skipping the first SPRI isolation of nucleic acids) improved the number of unique molecules that were detected per cell (see Table 19).

TABLE 19

Streptavidin Selection and PMSF

| Approach | Unique RNA Molecules Detected Per Cell (UMIs per cell) |
|---|---|
| SPRI cleanup, followed by streptavidin selection | 1562.32 |
| Streptavidin selection directly in lysis buffer (with protease inhibitor PMSF) | 1894.85 |

Example 13—0.6× vs. 0.8×SPRI Cleanup

In other protocols (see, e.g., Rosenberg, A B, et al. BioRxiv (2017): 105163), after cDNA amplification, a 0.6× SPRI cleanup was performed. After cDNA amplification short products (i.e., products under about 200 base pairs) can be removed using a SPRI cleanup. Herein, it was found that adding a 0.8:1 ratio of SPRI beads to PCR product resulted in more detected unique RNA molecules per cell than the previous 0.6:1 ratio of SPRI to PCR products (see Table 20).

TABLE 20

0.6× vs. 0.8 × SPRI Cleanup

| Approach | Unique RNA Molecules Detected Per Cell (UMIs per cell) |
|---|---|
| 0.6 × SPRI cleanup after cDNA amplification | 1562.32 |
| 0.8 × SPRI cleanup after cDNA amplification | 2553.36 |

Example 14—Concentrations of Random Hexamer and polydT RT Primers

In other protocols (see, e.g., Rosenberg, A B, et al. BioRxiv (2017): 105163) reverse transcription using solely polydT primers for reverse transcription is performed. Herein, it was found that by combining barcoded random hexamer primers and altering the concentrations led to a significant increase in UMIs/cell. With reference to Table 21, Protocol, Version 2.1 uses condition number 4 (729 UMIs/cell). With continued reference to Table 21, herein, condition number 10 was used (1263 UMIs/cell). Accordingly, combining random hexamer and polydT reverse transcription primers together at specific concentrations increases efficiency of in situ reverse transcription.

TABLE 21

| Condition Number | PolydT_15 micromolar (uM) concentration | PolydT_30 micromolar (uM) concentration | Random Hexamer micromolar (uM) concentration | PotydT_15 UMIs/cell | PolydT_30 UMIs/cell | Random Hexamer UMIs/cell | Total UMIs/cell from condition |
|---|---|---|---|---|---|---|---|
| 1 | 0.5 | 0 | 0 | 245.47 | — | — | 245.47 |
| 2 | 2.5 | 0 | 0 | 355.71 | — | — | 355.71 |
| 3 | 5 | 0 | 0 | 549.06 | — | — | 549.06 |
| 4 | 10 | 0 | 0 | 729.03 | — | — | 729.03 |
| 5 | 0 | 0.5 | 0 | — | 452.23 | — | 452.23 |
| 6 | 0 | 2.5 | 0 | — | 344.73 | — | 344.73 |
| 7 | 0 | 5 | 0 | — | 318.44 | — | 318.44 |
| 8 | 0 | 10 | 0 | — | 437.13 | — | 437.13 |
| 9 | 0.5 | 0 | 0.5 | 621.77 | — | 206.27 | 828.04 |
| 10 | 2.5 | 0 | 2.5 | 618.31 | — | 644.81 | 1263.12 |
| 11 | 5 | 0 | 5 | 625.43 | — | 445.9 | 1071.33 |
| 12 | 10 | 0 | 10 | 390.94 | — | 383.22 | 774.16 |

Example 15—Using the First Round of Barcodes as a Sample Identifier

Barcoded reverse transcription primers were used to generate first round barcodes in cDNA molecules. These cDNA molecules are then barcoded further by appending barcodes to the 5' end with ligation as described above.

A proof of concept is described in Rosenberg, A B, et al. (2018) Science, 360(6385); 176-182, which is hereby incorporated by reference in its entirety. As described therein, an experiment included four (4) unique samples and which cell belonged to which sample was essentially tracked by observing the first barcode (incorporated through RT). This sample identification can require knowing the corresponding barcode sequence to each well and which samples were placed into which well. With this information, a lookup table from first round barcode sequences to sample IDs can be created.

FIGS. 20 and 21A-21C show an experimental setup for multiplexing samples. In this specific case, 4 samples were multiplexed over 48 wells in a 96-well plate. One can see how this same logic can be expanded to multiplex up to 96 samples in a single experiment.

Figure 22:
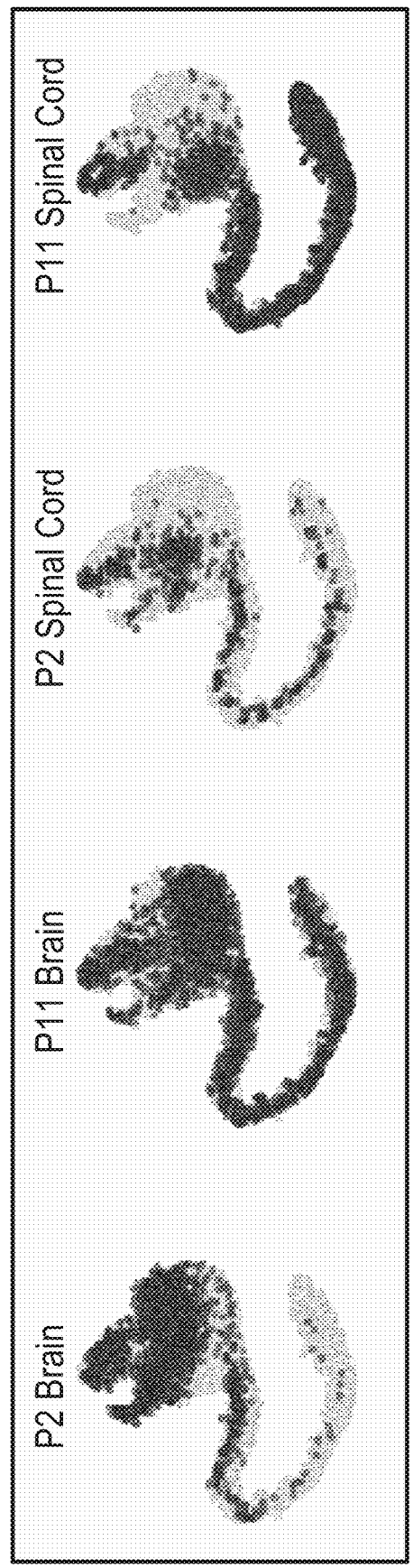
FIG. 22 depicts the distribution of P2/P11 brain and spinal cord single-nucleus transcriptomes within the oligodendrocyte lineage. Each nuclei's sample (P2 spine, P2 brain, P11 spine, or P11 spine) can be determined by examining the first-round barcode from each cell/nuclei barcode combination.

With reference to FIG. 22, analysis of transcriptomes using T-distributed Stochastic Neighbor Embedding (t-SNE) in an experiment with four different biological samples is shown. Each point represents the transcriptome from one individual cell. Using the identity of the barcodes incorporated during RT (with barcoded RT primers), the sample identity of each transcriptome can be determined.

Example 16—Incorporating PEG for Template Switching of DNA/RNA Bound to Magnetic Beads A biotinylated oligo attached to reverse transcribed RNA (cDNA/RNA duplex) is bound to a streptavidin coated magnetic bead. Then, template switching is performed on this cDNA/RNA duplex so that a single common adapter sequence can incorporated to the 3' end of cDNA. Incorporating up to 10% w/v PEG (molecular weight 7000-9000) into the template switch reaction, which includes cDNA/RNA duplex bound to streptavidin coated magnetic beads, can improve the efficiency of this step as measured by transcript detection per cell (Table 22).

TABLE 22

Template Switch with or without PEG 8000

| Approach | Unique RNA Molecules Detected Per Cell (UMIs per cell) |
|---|---|
| Template Switch without PEG 8000 | 2645.0 |
| Template Switch with 7.5% PEG 8000 | 5759.0 |

Example 18—Exemplary Methods of Uniquely Labeling RNA Molecules

Figure 23A:
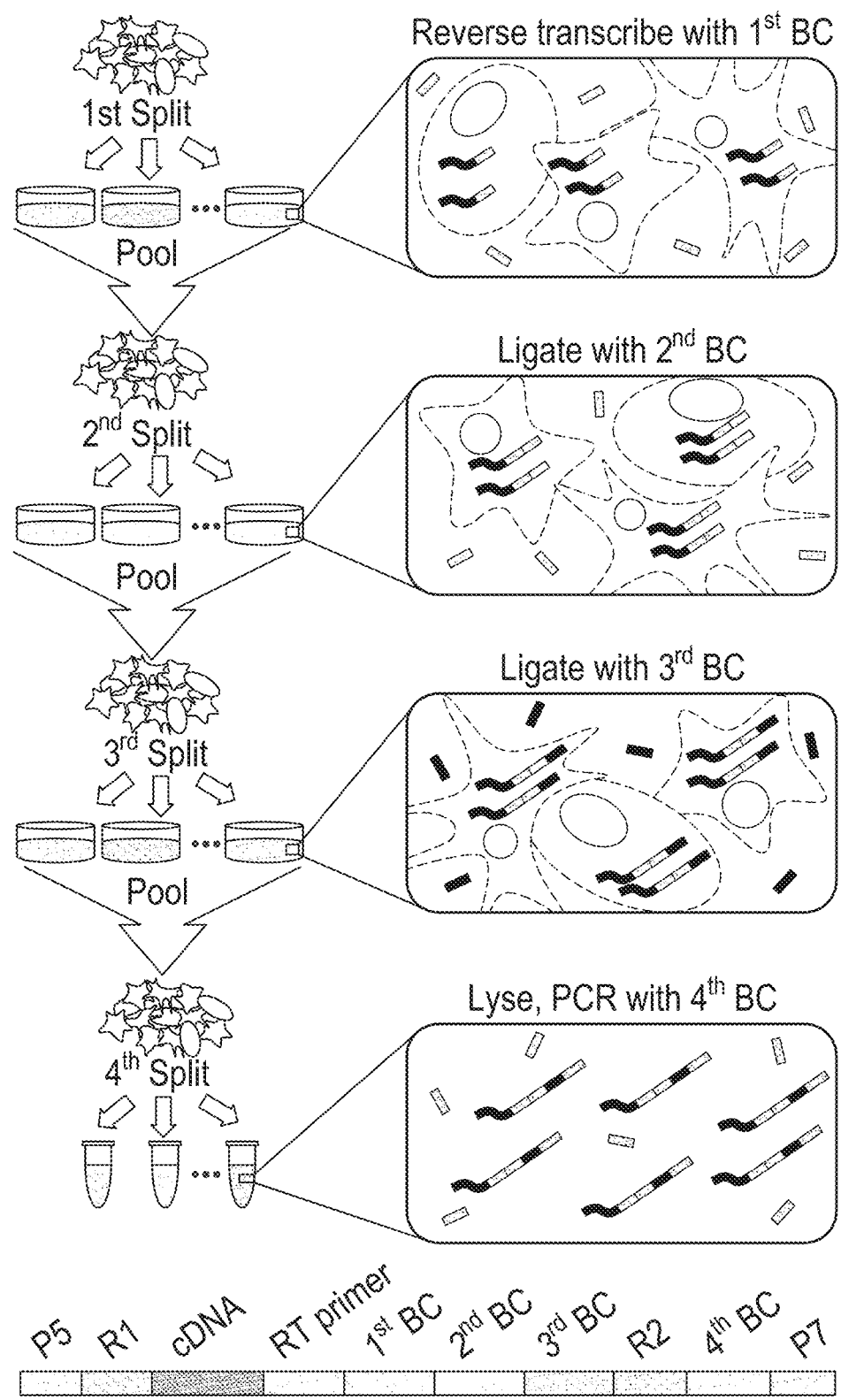
FIGS. 23A-23D depict an overview of a protocol as provided herein.

FIG. 23A depicts labeling transcriptomes with split-pool barcoding. In each split-pool round, fixed cells or nuclei can be randomly distributed into wells and transcripts can be labeled with well-specific barcodes. Barcoded RT primers can be used in the first round. Second and third round barcodes can be appended to cDNA through ligation. A fourth barcode can be added to cDNA molecules by PCR during sequencing library preparation. The bottom scheme shows the final barcoded cDNA molecule.

Figure 23B:
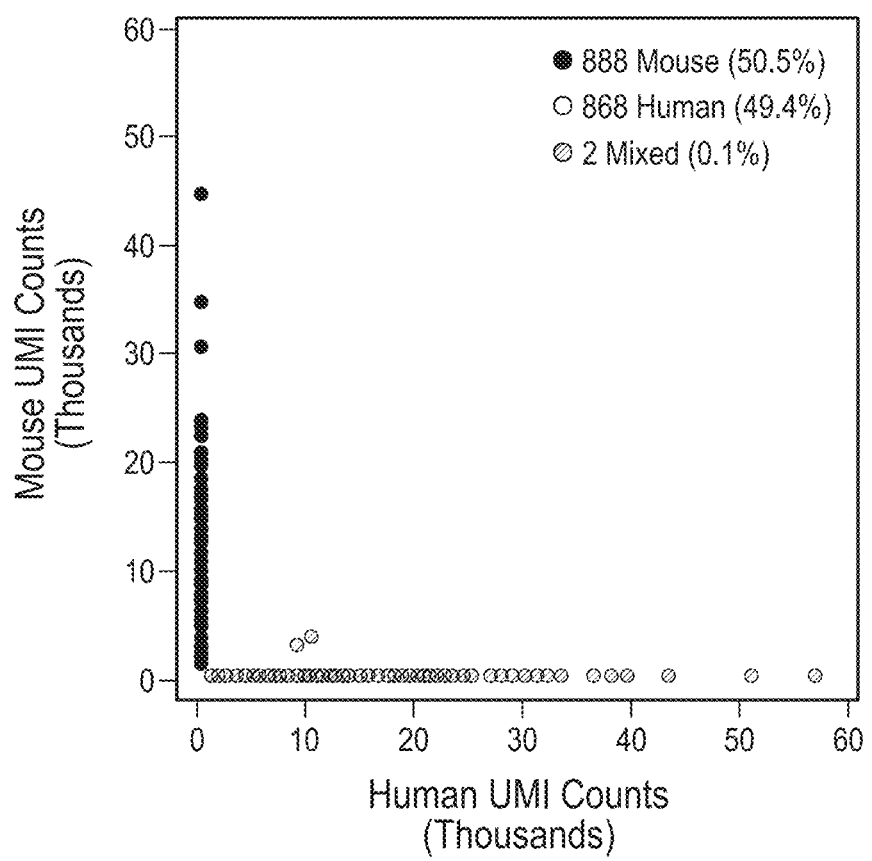

FIG. 23B shows a species mixing experiment with a library prepared from 1,758 whole cells. Human UBCs extend horizontally along the x-axis, mouse UBCs are extend vertically along the y-axis, and mixed-species UBCs are disposed between the human and mouse UBCs. The estimated barcode collision rate is 0.2%, whereas species purity is >99%.

Figure 23C:
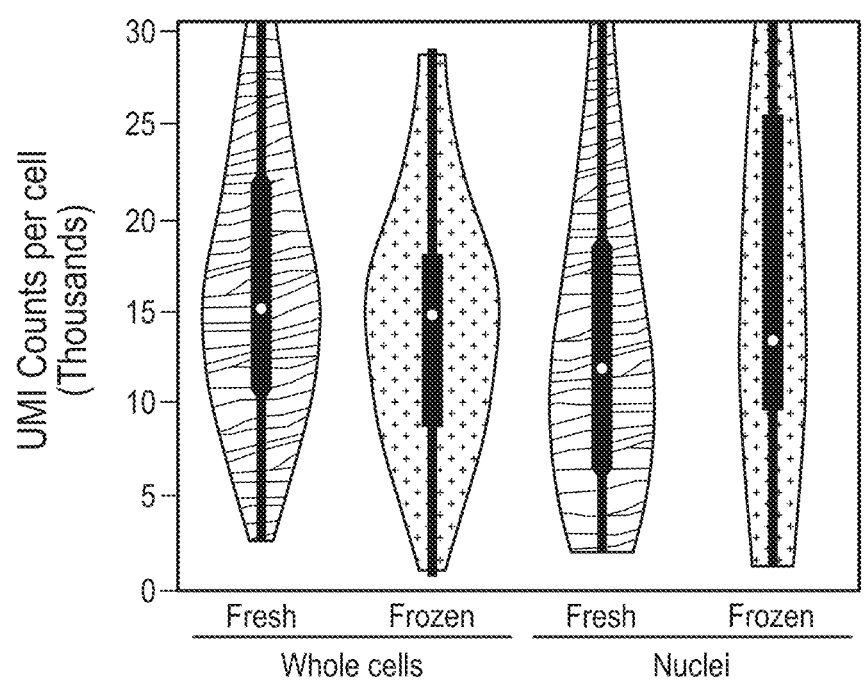

FIG. 23C shows UMI counts from mixing experiments performed with fresh and frozen (stored at −80° C. for 2 weeks) cells and nuclei. Median human UMI counts for fresh cells: 15,365; frozen cells: 15,078; nuclei: 12,113; frozen nuclei: 13,636.

Figure 23D:
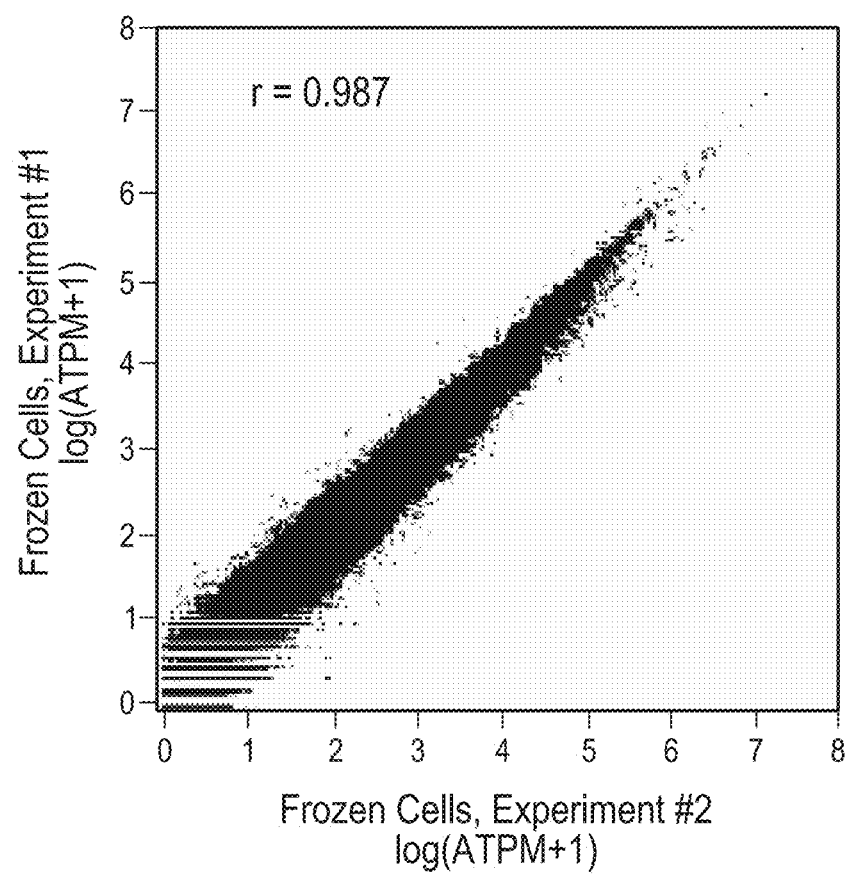

FIG. 23D shows measured gene expression by the methods provided here is highly correlated between frozen cells and cells processed immediately (Pearson-r: 0.987). Frozen and fresh cells were processed in two different SPLIT-seq experiments.

Figure 24:
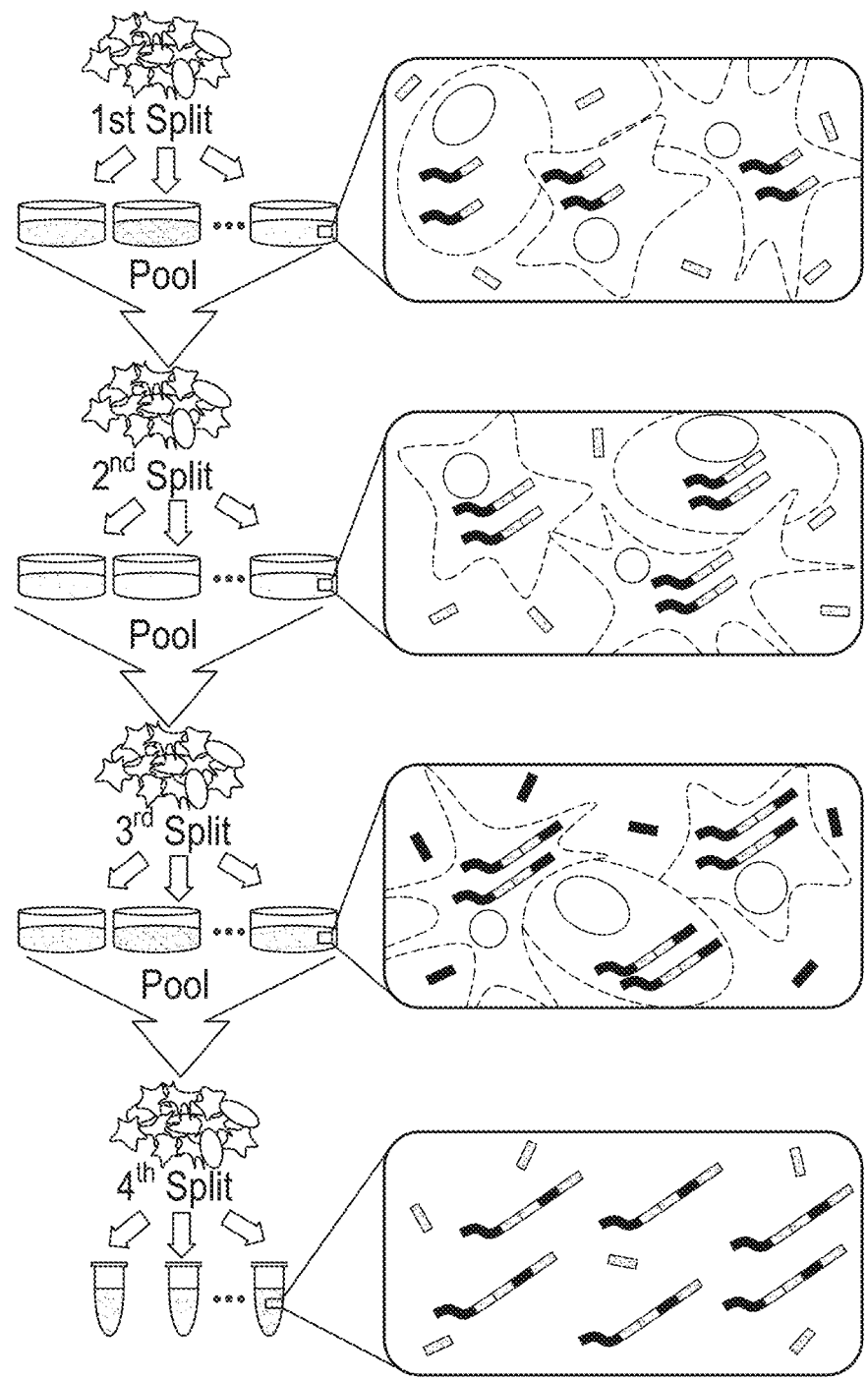
FIG. 24 depicts a molecular diagram of a protocol as provided herein.
Figure 24:
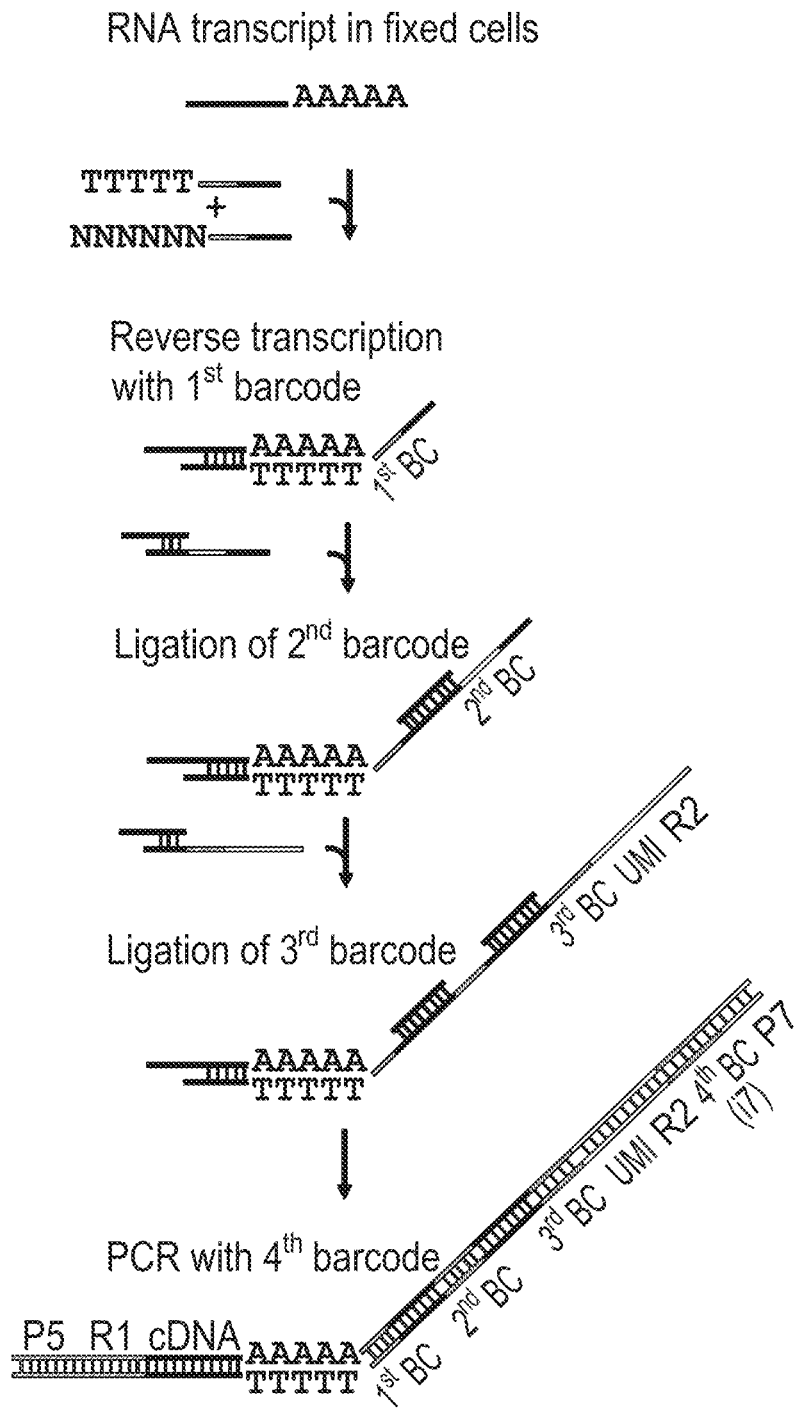

As illustrated in FIG. 24, fixed and permeabilized cells can be randomly split into wells that each contain reverse transcription primers with a well-specific barcode. In situ reverse transcription converts RNA to cDNA while appending the well-specific barcode. Cells can then be pooled and again randomly split into a second set of wells, each containing a unique well-specific barcode. These barcodes can be hybridized and ligated to the 5'-end of the barcoded reverse transcription primer to add a second round of barcoding. The cells can be pooled back together and a subsequent split-ligate-pool round can be performed. After the last round of ligation, cDNA molecules contain a cell-specific combination of barcodes, a unique molecular identifier, and a universal PCR handle on the 5'-end. A fourth barcoding round can be performed during the PCR step of library preparation.

The oligonucleotides listed in Table 23 were used in the Examples above. "rG" is an RNA base and "+G" is a locked nucleic acid base.

TABLE 23

Oligonucleotides

| Oligonucleotide Number | Description | Sequence | SEQ ID NO. |
|---|---|---|---|
| BC_0060 | Round 3 barcode linker | AGTCGTACGCCGATG CGAAACATCGGCCAC | SEQ ID NO. 16 |
| BC_0062 | PCR primer, used after template switching (used with BC_0108) | CAGACGTGTGCTCTTC CGATCT | SEQ ID NO. 17 |

TABLE 23-continued

Oligonucleotides

| Oligonucleotide Number | Description | Sequence | SEQ ID NO. |
|---|---|---|---|
| BC_0066 | Round 3 blocking strand | GTGGCCGATGTTTCGCATCGGCGTACGACT | SEQ ID NO. 18 |
| BC_0076 | Nextera Tagmentation PCR primer (TSBC07), sublibrary index #1 (used with BC_0118) | CAAGCAGAAGACGGCATACGAGATGATCTGGTGACTGGAGTTCAGACGTGTGCTCTTCCGATCT | SEQ ID NO. 19 |
| BC_0077 | Nextera Tagmentation PCR primer (TSBC08), sublibrary index #2 (used with BC_0118) | CAAGCAGAAGACGGCATACGAGATTCAAGTGTGACTGGAGTTCAGACGTGTGCTCTTCCGATCT | SEQ ID NO. 20 |
| BC_0078 | Nextera Tagmentation PCR primer (TSBC09), sublibrary index #3 (used with BC_0118) | CAAGCAGAAGACGGCATACGAGATCTGATCGTGACTGGAGTTCAGACGTGTGCTCTTCCGATCT | SEQ ID NO. 21 |
| BC_0079 | Nextera Tagmentation PCR primer (TSBC10), sublibrary index #4 (used with BC_0118) | CAAGCAGAAGACGGCATACGAGATAAGCTAGTGACTGGAGTTCAGACGTGTGCTCTTCCGATCT | SEQ ID NO. 22 |
| BC_0080 | Nextera Tagmentation PCR primer (TSBC11), sublibrary index #5 (used with BC_0118) | CAAGCAGAAGACGGCATACGAGATGTAGCCGTGACTGGAGTTCAGACGTGTGCTCTTCCGATCT | SEQ ID NO. 23 |
| BC_0081 | Nextera Tagmentation PCR primer (TSBC12), sublibrary index #6 (used with BC_0118) | CAAGCAGAAGACGGCATACGAGATTACAAGGTGACTGGAGTTCAGACGTGTGCTCTTCCGATCT | SEQ ID NO. 24 |
| BC_0082 | Nextera Tagmentation PCR primer (TSBC13), sublibrary index #7 (used with BC_0118) | CAAGCAGAAGACGGCATACGAGATTTGACTGTGACTGGAGTTCAGACGTGTGCTCTTCCGATCT | SEQ ID NO. 25 |
| BC_0083 | Nextera Tagmentation PCR primer (TSBC14), sublibrary index #8 (used with BC_0118) | CAAGCAGAAGACGGCATACGAGATGGAACTGTGACTGGAGTTCAGACGTGTGCTCTTCCGATCT | SEQ ID NO. 26 |
| BC_0108 | PCR primer, used after template switching (used with BC_0062) | AAGCAGTGGTATCAACGCAGAGT | SEQ ID NO. 27 |
| BC_0118 | Nextera Tagmentation PCR primer N501 (used with BC_0076 through BC_0083) | AATGATACGGCGACCACCGAGATCTACACTAGATCGCTCGTCGGCAGCGTCAGATGTGTATAAGAGACAG | SEQ ID NO. 28 |
| BC_0127 | Template switching primer, HPLC purified (purchased from Exiqon) | AAGCAGTGGTATCAACGCAGAGTGAATrGrG+G | SEQ ID NO. 29 |
| BC_0215 | Round 2 barcode linker | CGAATGCTCTGGCCTCTCAAGCACGTGGAT | SEQ ID NO. 30 |
| BC_0216 | Round 2 blocking strand | ATCCACGTGCTTGAGAGGCCAGAGCATTCG | SEQ ID NO. 31 |

Certain embodiments of this disclosure are described herein, including the best mode known to the inventors for carrying out the disclosure. Of course, variations on these described embodiments will become apparent to those of ordinary skill in the art upon reading the foregoing description. The applicants expect skilled artisans to employ such variations as appropriate, and the applicants intend for the various embodiments of the disclosure to be practiced otherwise than specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

Furthermore, numerous references have been made to patents and printed publications throughout this specification. Each of the above-cited references and printed publications are individually incorporated herein by reference in their entirety.

It is to be understood that the embodiments of the present disclosure are illustrative of the principles of the present disclosure. Other modifications that may be employed are within the scope of the disclosure. Thus, by way of example, but not of limitation, alternative configurations of the present disclosure may be utilized in accordance with the teachings herein. Accordingly, the present disclosure is not limited to that precisely as shown and described.

The particulars shown herein are by way of example and for purposes of illustrative discussion of the preferred embodiments of the present disclosure only and are presented in the cause of providing what is believed to be the most useful and readily understood description of the principles and conceptual aspects of various embodiments of the disclosure.

It will be apparent to those having skill in the art that many changes may be made to the details of the above-described embodiments without departing from the underlying principles of the disclosure. The scope of the present invention should, therefore, be determined only by the following claims.

The invention claimed is:

1. A method of labeling RNA molecules with nucleus-specific tags, the method comprising:
   (a) fixing and permeabilizing a plurality of nuclei, wherein each of the plurality of fixed, permeabilized nuclei comprises RNA, and wherein the plurality of nuclei is fixed and permeabilized at a temperature below about 8° C.;
   (b) dividing the plurality of nuclei into a first plurality of aliquots, wherein each aliquot of the first plurality of aliquots comprises more than one nucleus;
   (c) reverse transcribing RNA molecules within the nuclei of the first plurality of aliquots to generate complementary DNA (cDNA) molecules, wherein the RNA molecules are reverse transcribed using reverse transcription (RT) primers each comprising:
   (i) a poly(T) sequence or a random nucleotide sequence,
   (ii) an RT primer barcode sequence,
   wherein multiple distinct RT primer barcode sequences are present among the RT primers used in the first plurality of aliquots; and
   wherein the RT primer barcode sequences present in each individual aliquot of the first plurality of aliquots are specific to the individual aliquot; and
   (iii) a 5' overhang comprising a 5' overhang sequence located 5' of the poly(T) or the random nucleotide sequence,
   wherein the 5' overhang sequence is the same in all of the RT primers used in the first plurality of aliquots, and
   wherein following reverse transcription of the RNA, the 5' overhang sequence is present at the 5' end of each of the cDNA molecules;
   (d) combining the nuclei from the first plurality of aliquots;
   (e) dividing the combined nuclei from the first plurality of aliquots into a second plurality of aliquots, wherein each of the second plurality of aliquots comprises more than one nucleus;
   (f) coupling nucleic acid tags to the cDNA molecules within nuclei of the second plurality of aliquots, thereby generating tagged cDNA molecules, wherein each of the nucleic acid tags comprises:
   i) a tag barcode sequence, and
   ii) a 3' hybridization sequence located 3' of the barcode sequence and/or a 5' hybridization sequence located 5' of the barcode sequence, wherein multiple distinct tag barcode sequences are present among the nucleic acid tags used in the second plurality of aliquots, and wherein the tag barcode sequences present in each individual aliquot of the second plurality of aliquots are specific to the individual aliquot; and (g) combining the nuclei from the second plurality of aliquots;

(h) dividing the combined nuclei from the second plurality of aliquots into a plurality of samples, wherein each sample of the plurality of samples comprises more than one nucleus; and (i) lysing the nuclei in the plurality of samples, thereby releasing the tagged cDNA molecules and forming a lysate in each sample of the plurality of samples.

2. The method of claim 1, further comprising: (j) isolating the tagged cDNA molecules released during step (i) using a binding agent, such that the isolated tagged cDNA molecules are bound to the binding agent.

3. The method of claim 2, wherein the binding agent comprises streptavidin-coated magnetic beads.

4. The method of claim 2, wherein the lysing of step (i) is performed in the presence of a protease, and wherein a protease inhibitor is added to the lysate prior to or together with the binding agent.

5. The method of claim 4, wherein the protease is proteinase K.

6. The method of claim 4, wherein the protease inhibitor is phenylmethanesulfonyl fluoride (PMSF) or 4-(2-aminoethyl)benzenesulfonyl fluoride hydrochloride (AEBSF).

7. The method of claim 2, further comprising:
(k) conducting a template switch of the tagged cDNA molecules bound to the binding agent.

8. The method of claim 1, further comprising:
(l) amplifying the tagged cDNA molecules released in step (h) using amplification primers,
wherein at least a portion of the amplification primers used in each of the plurality of samples comprise an index sequence,
wherein multiple distinct index sequences are present among the amplification primers used in the plurality of samples, and
wherein the index sequences present in each individual sample of the plurality of samples are specific to the individual sample.

9. The method of claim 8, wherein the tagged cDNA molecules amplified in step (l) are present in an amplified cDNA solution, and further comprising:
(m) size selecting the tagged cDNA molecules amplified in step (l) by introducing a solid phase reversible immobilization (SPRI) bead solution to the amplified cDNA solution, wherein the ratio of SPRI bead solution to amplified cDNA solution is between about 0.9:1 and about 0:7:1.

10. The method of claim 9, wherein the ratio of SPRI bead solution to amplified cDNA solution is about 0.8:1.

11. The method of claim 1, wherein the plurality of nuclei is fixed and permeabilized at about 4° C. or below about 4° C.

12. The method of claim 1, wherein steps (e) through (g) are repeated one or more times, thereby generating repeatedly tagged cDNA molecules.

13. The method of claim 12, wherein steps (e) through (g) are repeated a number of times sufficient to generate at least as many distinct combinations of barcode sequences within the repeatedly tagged cDNA molecules as the number of cells in the plurality of nuclei.

14. The method of claim 1, wherein the coupling in step (f) comprises ligating a 3' end of a nucleic acid tag to a 5' end of a cDNA molecule.

15. The method of claim 14, wherein the 3' end of the nucleic acid tag is present within the 3' hybridization sequence, and wherein the 3' end of the nucleic acid tag is brought into proximity of the 5' end of the cDNA molecule by being preannealed to a linker nucleic acid strand that is complementary to the 3' hybridization sequence of the nucleic acid tag and to the 5' overhang sequence of the RT primer.

16. The method of claim 15, wherein the coupling is stopped by introducing a plurality of ligation stop oligos that are complementary to all or part of the linker nucleic acid strand.

17. The method of claim 12, wherein the coupling in step (f) during the one or more times that steps (e) to (g) are repeated comprises ligating a 3' end of a nucleic acid tag to the 5' end of a tagged or repeatedly tagged cDNA molecule.

18. The method of claim 1, wherein the RT primers and/or nucleic acid tags are DNA molecules.

19. The method of claim 12, wherein the nucleic acid tags that are coupled to the tagged or repeatedly tagged cDNA molecules during the last of the one or more times that steps (e) to (g) are repeated comprise one or more elements selected from the group consisting of a random nucleotide sequence to prevent counting of PCR duplicates, a capture agent, and a next-generation sequencing (NGS) adapter sequence.

20. The method of claim 19, wherein the capture agent comprises biotin.

21. The method of claim 1, wherein the RT primer barcode sequences and/or the tag barcode sequences each comprise at least 8 nucleotides.

22. The method of claim 8, wherein at least a portion of the amplification primers further comprise one or more elements selected from the group consisting of a flow-cell binding sequence, an NGS primer binding sequence, and an NGS adapter sequence.

23. The method of claim 1, wherein the plurality of nuclei comprise mammalian nuclei.

24. The method of claim 1, wherein a portion of the RT primers comprise a poly(T) sequence and a portion of the RT primers comprise a random nucleotide sequence, and wherein during step (c) the concentrations of the RT primers comprising a poly(T) sequence and the RT primers comprising a random nucleotide sequence are each between about 2.5 and 5 micromolar (uM).

25. The method of claim 8, further comprising:
(n) sequencing the tagged cDNA molecules amplified in step (l).

26. The method of claim 25, wherein the cDNA molecules have been amplified using one or more amplification primers comprising an index sequence, and wherein the method further comprises:
(o) grouping the sequencing reads obtained in step (n) by any combination of two or more sequences selected from the group consisting of RT primer barcode sequence, tag barcode sequence, and index sequence.

27. The method of claim 26, wherein steps (e) to (g) have been repeated one or more times, thereby producing repeatedly tagged cDNA molecules each comprising multiple tag barcode sequences, and wherein the sequencing reads are grouped by any combination of two or more sequences selected from the group consisting of RT primer sequence, any one or more of the multiple tag barcode sequences, and index sequence.

28. The method of claim 1, wherein the nucleic acid tags used in the plurality of aliquots comprise 96 distinct barcode sequences.

29. The method of claim 28, wherein the plurality of aliquots comprises 96 aliquots distributed in a 96-well plate.

30. The method of claim 29, wherein each of the 96 distinct barcode sequences is present in only one of the 96 aliquots.

\* \* \* \* \*

```
                              SEQUENCE LISTING

Sequence total quantity: 31
SEQ ID NO: 1            moltype = DNA  length = 32
FEATURE                 Location/Qualifiers
misc_feature            1..32
                        note = Reverse transcription primer, top strand
misc_difference         1
                        note = misc_feature - n is a, c, g, or t
source                  1..32
                        mol_type = other DNA
                        organism = synthetic construct
SEQUENCE: 1
nbaaaaaaaa aaaaaaacga atgctctggc ct                                    32

SEQ ID NO: 2            moltype = DNA  length = 32
FEATURE                 Location/Qualifiers
misc_feature            1..32
                        note = Reverse transcription primer, bottom strand
misc_difference         32
                        note = misc_feature - n is a, c, g, or t
source                  1..32
                        mol_type = other DNA
                        organism = synthetic construct
SEQUENCE: 2
aggccagagc attcgttttt tttttttttt vn                                    32

SEQ ID NO: 3            moltype = DNA  length = 30
FEATURE                 Location/Qualifiers
misc_feature            1..30
                        note = BC_0056_S0-S1
source                  1..30
                        mol_type = other DNA
                        organism = synthetic construct
SEQUENCE: 3
cgaatgctct ggccttcgga cgatcatggg                                       30

SEQ ID NO: 4            moltype = DNA  length = 38
FEATURE                 Location/Qualifiers
misc_feature            1..38
                        note = Round 1 barcodes
misc_difference         16..23
                        note = misc_feature - n is a, c, g, or t
source                  1..38
                        mol_type = other DNA
                        organism = synthetic construct
SEQUENCE: 4
cgcgctgcat acttgnnnnn nnncccatga tcgtccga                              38

SEQ ID NO: 5            moltype = DNA  length = 30
FEATURE                 Location/Qualifiers
misc_feature            1..30
                        note = BC_0058_S2-S3
```

```
source                          1..30
                                mol_type = other DNA
                                organism = synthetic construct
SEQUENCE: 5
caagtatgca gcgcggggaa gcacgtggat                                              30

SEQ ID NO: 6                    moltype = DNA   length = 38
FEATURE                         Location/Qualifiers
misc_feature                    1..38
                                note = Round 2 barcodes
misc_difference                 16..23
                                note = misc_feature - n is a, c, g, or t
source                          1..38
                                mol_type = other DNA
                                organism = synthetic construct
SEQUENCE: 6
catcggcgta cgactnnnnn nnnatccacg tgcttccc                                     38

SEQ ID NO: 7                    moltype = DNA   length = 30
FEATURE                         Location/Qualifiers
misc_feature                    1..30
                                note = BC_0060_S4-S5
source                          1..30
                                mol_type = other DNA
                                organism = synthetic construct
SEQUENCE: 7
agtcgtacgc cgatgcgaaa catcggccac                                              30

SEQ ID NO: 8                    moltype = DNA   length = 55
FEATURE                         Location/Qualifiers
misc_feature                    1..55
                                note = Round 3 barcodes
misc_difference                 23..40
                                note = misc_feature - n is a, c, g, or t
source                          1..55
                                mol_type = other DNA
                                organism = synthetic construct
SEQUENCE: 8
cagacgtgtg ctcttccgat ctnnnnnnnn nnnnnnnnnn gtggccgatg tttcg                  55

SEQ ID NO: 9                    moltype = DNA   length = 191
FEATURE                         Location/Qualifiers
misc_feature                    1..191
                                note = Stop ligation oligos, top strand
misc_difference                 1..29
                                note = misc_feature - n is a, c, g, or t
misc_difference                 76..83
                                note = misc_feature - n is a, c, g, or t
misc_difference                 114..121
                                note = misc_feature - n is a, c, g, or t
misc_difference                 152..169
                                note = misc_feature - n is a, c, g, or t
source                          1..191
                                mol_type = other DNA
                                organism = synthetic construct
SEQUENCE: 9
nnnnnnnnnn nnnnnnnnnn nnnnnnnnnb aaaaaaaaaa aaaaacgaat gctctggcct             60
tcggacgatc atgggnnnnn nnncaagtat gcagcgcggg gaagcacgtg gatnnnnnnn            120
nagtcgtacg ccgatgcgaa acatcggcca cnnnnnnnnn nnnnnnnnna gatcggaaga            180
gcacacgtct g                                                                191

SEQ ID NO: 10                   moltype = DNA   length = 191
FEATURE                         Location/Qualifiers
misc_feature                    1..191
                                note = Stop ligation oligos, bottom strand
misc_difference                 23..40
                                note = misc_feature - n is a, c, g, or t
misc_difference                 71..78
                                note = misc_feature - n is a, c, g, or t
misc_difference                 109..116
                                note = misc_feature - n is a, c, g, or t
misc_difference                 163..191
                                note = misc_feature - n is a, c, g, or t
source                          1..191
                                mol_type = other DNA
                                organism = synthetic construct
SEQUENCE: 10
cagacgtgtg ctcttccgat ctnnnnnnnn nnnnnnnnnn gtggccgatg tttcgcatcg             60
gcgtacgact nnnnnnnnat ccacgtgctt ccccgcgctg catacttgnn nnnnncccca            120
```

```
tgatcgtccg aaggccagag cattcgtttt tttttttttt tvnnnnnnnn nnnnnnnnnn    180
nnnnnnnnnn n                                                        191

SEQ ID NO: 11            moltype = DNA  length = 214
FEATURE                  Location/Qualifiers
misc_feature             1..214
                         note = 3' adapter ligation
misc_difference          24..52
                         note = misc_feature - n is a, c, g, or t
misc_difference          99..106
                         note = misc_feature - n is a, c, g, or t
misc_difference          137..144
                         note = misc_feature - n is a, c, g, or t
misc_difference          175..192
                         note = misc_feature - n is a, c, g, or t
source                   1..214
                         mol_type = other DNA
                         organism = synthetic construct
SEQUENCE: 11
ggatgtgctg cgagaaggct agannnnnnn nnnnnnnnnn nnnnnnnnnn nnvtttttt     60
tttttttgc ttacgagacc ggaagcctgc tagtacccnn nnnnnngttc atacgtcgcg    120
ccccttcgtg caccta nnnn nnnntcagca tgcggctacg ctttgtagcc ggtgnnnnnn  180
nnnnnnnnnn nntctagcct tctcgtgtgc agac                               214

SEQ ID NO: 12            moltype = DNA  length = 214
FEATURE                  Location/Qualifiers
misc_feature             1..214
                         note = PCR #1, top strand
misc_difference          24..52
                         note = misc_feature - n is a, c, g, or t
misc_difference          99..106
                         note = misc_feature - n is a, c, g, or t
misc_difference          137..144
                         note = misc_feature - n is a, c, g, or t
misc_difference          175..192
                         note = misc_feature - n is a, c, g, or t
source                   1..214
                         mol_type = other DNA
                         organism = synthetic construct
SEQUENCE: 12
cctacacgac gctcttccga tctnnnnnnnn nnnnnnnnnn nnnnnnnnnn nnbaaaaaaa    60
aaaaaaaacg aatgctctgg ccttcggacg atcatgggnn nnnnnncaag tatgcagcgc   120
ggggaagcac gtggatnnnn nnnnagtcgt acgccgatgc gaaacatcgg ccacnnnnnn   180
nnnnnnnn nnagatcgga agagcacacg tctg                                 214

SEQ ID NO: 13            moltype = DNA  length = 214
FEATURE                  Location/Qualifiers
misc_feature             1..214
                         note = PCR #1, bottom strand
misc_difference          23..40
                         note = misc_feature - n is a, c, g, or t
misc_difference          71..78
                         note = misc_feature - n is a, c, g, or t
misc_difference          109..116
                         note = misc_feature - n is a, c, g, or t
misc_difference          163..191
                         note = misc_feature - n is a, c, g, or t
source                   1..214
                         mol_type = other DNA
                         organism = synthetic construct
SEQUENCE: 13
cagacgtgtg ctcttccgat ctnnnnnnnn nnnnnnnnnn gtggccgatg tttcgcatcg    60
gcgtacgact nnnnnnnnat ccacgtgctt ccccgcgctg catacttgnn nnnnnnccca   120
tgatcgtccg aaggccagag cattcgtttt tttttttttt tvnnnnnnnn nnnnnnnnnn   180
nnnnnnnnnn nagatcggaa gagcgtcgtg tagg                               214

SEQ ID NO: 14            moltype = DNA  length = 292
FEATURE                  Location/Qualifiers
misc_feature             1..292
                         note = PCR #1, top strand
misc_difference          59..88
                         note = misc_feature - n is a, c, g, or t
misc_difference          135..142
                         note = misc_feature - n is a, c, g, or t
misc_difference          173..180
                         note = misc_feature - n is a, c, g, or t
misc_difference          211..228
                         note = misc_feature - n is a, c, g, or t
source                   1..292
```

```
                        mol_type = other DNA
                        organism = synthetic construct
SEQUENCE: 14
aatgatacgg cgaccaccga gatctacact ctttccctac acgacgctct tccgatctnn    60
nnnnnnnnnn nnnnnnnnnn nnnnnnnnba aaaaaaaaaa aaaacgaatg ctctggcctt   120
cggacgatca tgggnnnnnn nncaagtatg cagcgcgggg aagcacgtgg atnnnnnnnn   180
agtcgtacgc cgatgcgaaa catcggccac nnnnnnnnnn nnnnnnnnag atcggaagag   240
cacacgtctg aactccagtc acgatctgat ctcgtatgcc gtcttctgct tg          292

SEQ ID NO: 15           moltype = DNA   length = 292
FEATURE                 Location/Qualifiers
misc_feature            1..292
                        note = PCR #2, bottom strand
misc_difference         65..82
                        note = misc_feature - n is a, c, g, or t
misc_difference         113..120
                        note = misc_feature - n is a, c, g, or t
misc_difference         151..158
                        note = misc_feature - n is a, c, g, or t
misc_difference         205..234
                        note = misc_feature - n is a, c, g, or t
source                  1..292
                        mol_type = other DNA
                        organism = synthetic construct
SEQUENCE: 15
caagcagaag acggcatacg agatcagatc gtgactggag ttcagacgtg tgctcttccg    60
atctnnnnnn nnnnnnnnnn nngtggccga tgtttcgcat cggcgtacga ctnnnnnnnn   120
atccacgtgc ttccccgcgc tgcatacttg nnnnnnnncc catgatcgtc cgaaggccag   180
agcattcgtt tttttttttt tttvnnnnnn nnnnnnnnnn nnnnnnnnnn nnnnagatcg   240
gaagagcgtc gtgtagggaa agagtgtaga tctcggtggt cgccgtatca tt           292

SEQ ID NO: 16           moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 16
agtcgtacgc cgatgcgaaa catcggccac                                     30

SEQ ID NO: 17           moltype = DNA   length = 22
FEATURE                 Location/Qualifiers
misc_feature            1..22
                        note = Synthetic
source                  1..22
                        mol_type = other DNA
                        organism = synthetic construct
SEQUENCE: 17
cagacgtgtg ctcttccgat ct                                             22

SEQ ID NO: 18           moltype = DNA   length = 30
FEATURE                 Location/Qualifiers
misc_feature            1..30
                        note = Synthetic
source                  1..30
                        mol_type = other DNA
                        organism = synthetic construct
SEQUENCE: 18
gtggccgatg tttcgcatcg gcgtacgact                                     30

SEQ ID NO: 19           moltype = DNA   length = 64
FEATURE                 Location/Qualifiers
misc_feature            1..64
                        note = Synthetic
source                  1..64
                        mol_type = other DNA
                        organism = synthetic construct
SEQUENCE: 19
caagcagaag acggcatacg agatgatctg gtgactggag ttcagacgtg tgctcttccg    60
atct                                                                 64

SEQ ID NO: 20           moltype = DNA   length = 64
FEATURE                 Location/Qualifiers
misc_feature            1..64
                        note = Synthetic
source                  1..64
                        mol_type = other DNA
                        organism = synthetic construct
```

-continued

```
SEQUENCE: 20
caagcagaag acggcatacg agattcaagt gtgactggag ttcagacgtg tgctcttccg    60
atct                                                                64

SEQ ID NO: 21           moltype = DNA  length = 64
FEATURE                 Location/Qualifiers
misc_feature            1..64
                        note = Synthetic
source                  1..64
                        mol_type = other DNA
                        organism = synthetic construct
SEQUENCE: 21
caagcagaag acggcatacg agatctgatc gtgactggag ttcagacgtg tgctcttccg    60
atct                                                                64

SEQ ID NO: 22           moltype = DNA  length = 64
FEATURE                 Location/Qualifiers
misc_feature            1..64
                        note = Synthetic
source                  1..64
                        mol_type = other DNA
                        organism = synthetic construct
SEQUENCE: 22
caagcagaag acggcatacg agataagcta gtgactggag ttcagacgtg tgctcttccg    60
atct                                                                64

SEQ ID NO: 23           moltype = DNA  length = 64
FEATURE                 Location/Qualifiers
misc_feature            1..64
                        note = Synthetic
source                  1..64
                        mol_type = other DNA
                        organism = synthetic construct
SEQUENCE: 23
caagcagaag acggcatacg agatgtagcc gtgactggag ttcagacgtg tgctcttccg    60
atct                                                                64

SEQ ID NO: 24           moltype = DNA  length = 64
FEATURE                 Location/Qualifiers
misc_feature            1..64
                        note = Synthetic
source                  1..64
                        mol_type = other DNA
                        organism = synthetic construct
SEQUENCE: 24
caagcagaag acggcatacg agattacaag gtgactggag ttcagacgtg tgctcttccg    60
atct                                                                64

SEQ ID NO: 25           moltype = DNA  length = 64
FEATURE                 Location/Qualifiers
misc_feature            1..64
                        note = Synthetic
source                  1..64
                        mol_type = other DNA
                        organism = synthetic construct
SEQUENCE: 25
caagcagaag acggcatacg agatttgact gtgactggag ttcagacgtg tgctcttccg    60
atct                                                                64

SEQ ID NO: 26           moltype = DNA  length = 64
FEATURE                 Location/Qualifiers
misc_feature            1..64
                        note = Synthetic
source                  1..64
                        mol_type = other DNA
                        organism = synthetic construct
SEQUENCE: 26
caagcagaag acggcatacg agatggaact gtgactggag ttcagacgtg tgctcttccg    60
atct                                                                64

SEQ ID NO: 27           moltype = DNA  length = 23
FEATURE                 Location/Qualifiers
misc_feature            1..23
                        note = Synthetic
source                  1..23
                        mol_type = other DNA
                        organism = synthetic construct
SEQUENCE: 27
aagcagtggt atcaacgcag agt                                           23
```

```
SEQ ID NO: 28          moltype = DNA  length = 70
FEATURE                Location/Qualifiers
misc_feature           1..70
                       note = Synthetic
source                 1..70
                       mol_type = other DNA
                       organism = synthetic construct
SEQUENCE: 28
aatgatacgg cgaccaccga gatctacact agatcgctcg tcggcagcgt cagatgtgta    60
taagagacag                                                          70

SEQ ID NO: 29          moltype = DNA  length = 30
FEATURE                Location/Qualifiers
misc_feature           1..30
                       note = Synthetic
misc_feature           1..27
                       note = DNA
misc_feature           28..30
                       note = RNA
modified_base          30
                       mod_base = OTHER
                       note = Locked nucleic acid (LNA)
source                 1..30
                       mol_type = other DNA
                       organism = synthetic construct
SEQUENCE: 29
aagcagtggt atcaacgcag agtgaatggg                                    30

SEQ ID NO: 30          moltype = DNA  length = 30
FEATURE                Location/Qualifiers
misc_feature           1..30
                       note = Synthetic
source                 1..30
                       mol_type = other DNA
                       organism = synthetic construct
SEQUENCE: 30
cgaatgctct ggcctctcaa gcacgtggat                                    30

SEQ ID NO: 31          moltype = DNA  length = 30
FEATURE                Location/Qualifiers
misc_feature           1..30
                       note = Synthetic
source                 1..30
                       mol_type = other DNA
                       organism = synthetic construct
SEQUENCE: 31
atccacgtgc ttgagaggcc agagcattcg                                    30
```